(12) United States Patent
Stein et al.

(10) Patent No.: US 6,544,981 B2
(45) Date of Patent: Apr. 8, 2003

(54) LACTAM INHIBITORS OF FACTOR XA AND METHOD

(75) Inventors: Philip D. Stein, Pennington, NJ (US); Stephen P. O'Connor, Newtown, PA (US); Yan Shi, Flourtown, PA (US); Chi Li, Randolph, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/874,739

(22) Filed: Jun. 5, 2001

(65) Prior Publication Data
US 2002/0025957 A1 Feb. 28, 2002

Related U.S. Application Data

(60) Provisional application No. 60/210,384, filed on Jun. 9, 2000.

(51) Int. Cl.[7] .................... C07D 405/12; C07D 405/14; C07D 223/10; C07D 401/12; C07D 403/12
(52) U.S. Cl. ............................ 514/212.08; 514/212.08; 540/526; 540/527
(58) Field of Search ................................ 540/527, 526; 514/212.03, 212.08

(56) References Cited

FOREIGN PATENT DOCUMENTS

| WO | WO 98/24784 | 6/1988 |
|---|---|---|
| WO | WO 93 01208 | 1/1993 |
| WO | WO 96/40679 | 12/1996 |
| WO | WO 98/56365 | 12/1998 |
| WO | WO 00/47207 | 8/2000 |
| WO | WO 00/47563 | 8/2000 |

OTHER PUBLICATIONS

JP 09 165370A—Jun. 24, 1997 (Abstract).
Wittman, Helga et al., Chemical Abstract Service, Database Accession No. 90:121339, XP002178595.
Koomen, G. et al., JCS Perkin I, vol. 18, pp. 1934–1940 (1973) XP002111927.

Primary Examiner—Bruck Kifle
(74) Attorney, Agent, or Firm—Ronald S. Hermenau

(57) ABSTRACT

Lactam inhibitors are provided which have the structure

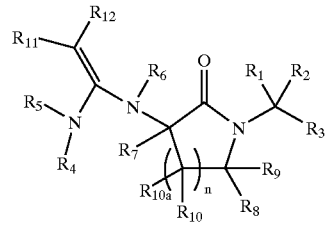

including pharmaceutically acceptable salts thereof and all stereoisomers thereof, and prodrug esters thereof, wherein n is 1 to 5; and
and $R_1$, $R_2$, $R_3$, $R_4$, $R_5$, $R_6$, $R_7$, $R_8$, $R_9$, $R_{10}$, $R_{10a}$, $R_{11}$ and $R_{12}$ are as defined herein. These compounds are inhibitors of Factor Xa and thus are useful as anticoagulants. A method for treating cardiovascular diseases associated with thromboses is also provided.

18 Claims, No Drawings

LACTAM INHIBITORS OF FACTOR XA AND METHOD

This application claims priority to provisional U.S. Application Serial No. 60/210,384 filed Jun. 9, 2000, the entirety of which is incorportated herein by reference.

FIELD OF THE INVENTION

The present invention relates to lactam inhibitors of the enzyme Factor Xa which are useful as anticoagulants in the treatment of cardiovascular diseases associated with thromboses.

BRIEF DESCRIPTION OF THE INVENTION

In accordance with the present invention, novel lactam derivatives are provided which are inhibitors of the enzyme Factor Xa and have the structure I

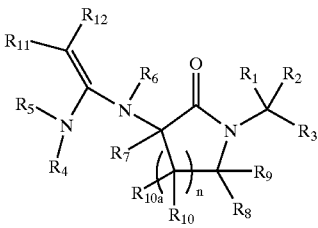

I including pharmaceutically acceptable salts thereof and all stereoisomers thereof, and prodrugs thereof, wherein n is an integer from 1 to 5;

$R_1$, $R_2$ and $R_3$ are the same or different and are independently selected from hydrogen, alkyl, alkenyl, alkynyl, aryl, heteroaryl, arylalkyl, arylalkenyl, arylalkynyl, alkoxy, cyano, nitro, heteroarylalkyl, cycloalkyl, cycloalkylalkyl, polycycloalkyl, polycycloalkylalkyl, cycloalkenyl, cycloalkynyl, alkylcarbonyl, arylcarbonyl, cycloheteroalkyl, cycloheteroalkylalkyl, cycloalkenylalkyl, polycycloalkenyl, polycycloalkenylalkyl, polycycloalkynyl, polycycloalkynylalkyl,

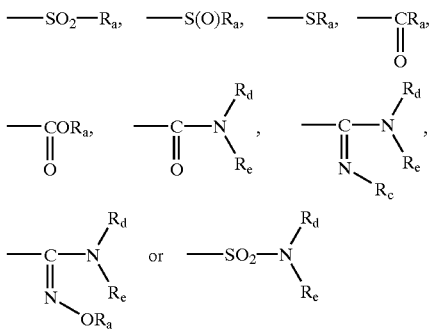

all optionally substituted through available atoms with 1, 2, 3, 4 or 5 groups selected from $Z_1$, $Z_2$, $Z_3$, $Z_4$, and $Z_5$;

or $R_1$, $R_2$ and $R_3$ can in pairs of two join together to form a saturated carbocylic or heterocyclic ring optionally substituted through available atoms with 1, 2, 3, 4 or 5 groups selected from $Z_1$, $Z_2$, $Z_3$, $Z_4$, and $Z_5$;

or $R_1$ and $R_2$ can join together to form an unsaturated carbocylic or heterocyclic ring optionally substituted through available atoms with 1, 2, 3, 4 or 5 groups selected from $Z_1$, $Z_2$, $Z_3$, $Z_4$, and $Z_5$ wherein $R^3$ is optionally a bond participating in the unsaturation of said ring;

$R_4$, $R_6$, $R_8$, $R_9$, $R_a$, $R_b$, are the same or different and are independently selected from hydrogen, alkyl, alkenyl, alkynyl, aryl, heteroaryl, arylalkyl, arylalkenyl, arylalkynyl, heteroarylalkyl, cycloalkyl, cycloalkylalkyl, polycycloalkyl, polycycloalkylalkyl, cycloalkenyl, cycloalkynyl, alkylcarbonyl, arylcarbonyl, cycloheteroalkyl, cycloheteroalkylalkyl, cycloalkenylalkyl, polycycloalkenyl, polycycloalkenylalkyl, polycycloalkynyl or polycycloalkynylalkyl; all optionally substituted through available atoms with 1, 2, 3, 4 or 5 groups selected from $Z_1$, $Z_2$, $Z_3$, $Z_4$, and $Z_5$;

$R_5$ is hydrogen, alkyl, alkenyl, alkynyl, aryl, heteroaryl, alkoxyalkyl, arylalkyl, heteroarylalkyl, arylalkenyl, arylalkynyl, cycloalkyl, cycloalkylalkyl, polycycloalkyl, polycycloalkylalkyl, cycloalkenyl, cycloalkynyl, alkylcarbonyl, aminocarbonyl, substituted aminocarbonyl, arylcarbonyl, cycloheteroalkyl, cycloheteroalkylalkyl, cycloalkenylalkyl, polycycloalkenyl, polycycloalkenylalkyl, polycycloalkynyl, polycycloalkynyl-alkyl, cyano, nitro, hydroxy, amino, —$OR_a$, —$SR_a$, —$S(O)R_a$,

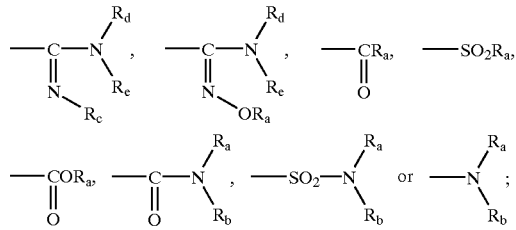

all optionally substituted through available atoms with 1, 2, 3, 4 or 5 groups selected from $Z_1$, $Z_2$, $Z_3$, $Z_4$, and $Z_5$;

$R_7$ is independently selected from hydrogen, alkyl, alkenyl, alkynyl, aryl, heteroaryl, arylalkyl, arylalkenyl, arylalkynyl, heteroarylalkyl, cycloalkyl, cycloalkylalkyl, polycycloalkyl, polycycloalkylalkyl, cycloalkenyl, cycloalkynyl, alkylcarbonyl, arylcarbonyl, cycloheteroalkyl, cycloheteroalkylalkyl, cycloalkenylalkyl, polycycloalkenyl, polycycloalkenylalkyl, polycycloalkynyl, polycycloalkynylalkyl,

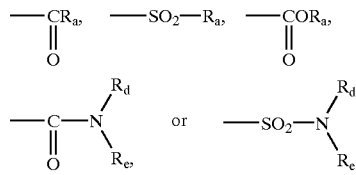

all optionally substituted through available atoms with 1, 2, 3, 4 or 5 groups selected from $Z_1$, $Z_2$, $Z_3$, $Z_4$, and $Z_5$;

$R_{10}$ and $R_{10a}$ are the same or different are independently selected from hydrogen, halogen, alkyl, alkenyl, alkynyl, aryl, heteroaryl, arylalkyl, arylalkenyl, arylalkynyl, heteroarylalkyl, cycloalkyl, cycloalkylalkyl, polycycloalkyl, polycycloalkylalkyl, cycloalkenyl, cycloalkynyl, alkylcarbonyl, arylcarbonyl, cycloheteroalkyl, cycloheteroalkylalkyl, cycloalkenylalkyl, polycycloalkenyl, polycycloalkenylalkyl, polycycloalkynyl polycycloalkynylalkyl,

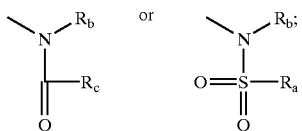

all optionally substituted through available atoms with 1, 2, 3, 4 or 5 groups selected from $Z_1$, $Z_2$, $Z_3$, $Z_4$, and $Z_5$;

$R_{11}$ and $R_{12}$ are the same or different and are independently selected from hydrogen, alkyl, aryl, cyano, nitro, heteroaryl, sulfonyl, acyl, amido, sufonamido, sulfamoyl, alkoxycarbonyl, carboxy, —C(O)$_z$R$_a$, —S(O)$_z$R$_a$, —P(O)(OR$_a$)$_z$ where Z is 1 or 2,

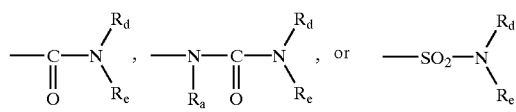

all optionally substituted through available atoms with 1, 2, 3, 4 or 5 groups selected from $Z_1$, $Z_2$, $Z_3$, $Z_4$, and $Z_5$;

$R_c$ is hydrogen, alkyl, alkenyl, alkynyl, aryl, heteroaryl, arylalkyl, arylalkenyl, arylalkynyl, heteroarylalkyl, cycloalkyl, cycloalkylalkyl, polycycloalkyl, polycycloalkylalkyl, cycloalkenyl, cycloalkynyl, cycloheteroalkyl, cycloheteroalkylalkyl, cycloalkenylalkyl, polycycloalkenyl, polycycloalkenylalkyl, polycycloalkynyl, polycycloalkynylalkyl,

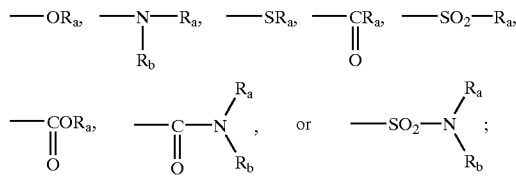

all optionally substituted through available atoms with 1, 2, 3, 4 or 5 groups selected from $Z_1$, $Z_2$, $Z_3$, $Z_4$, and $Z_5$;

$R_d$ and $R_e$ are the same or different and are independently selected from hydrogen, alkyl, alkenyl, alkynyl, aryl, heteroaryl, arylalkyl, alkoxyalkyl, arylalkenyl, arylalkynyl, heteroarylalkyl, cycloalkyl, cycloalkylalkyl, polycycloalkyl, polycycloalkylalkyl, cycloalkenyl, cycloalkynyl, alkylcarbonyl, arylcarbonyl, cycloheteroalkyl, cycloheteroalkylalkyl, cycloalkenylalkyl, polycycloalkenyl, polycycloalkenylalkyl, polycycloalkynyl, polycycloalkynylalkyl, hydroxyalkyl, alkoxycarbonyl, or aminocarbonyl; all optionally substituted through available atoms with 1, 2, 3, 4 or 5 groups selected from $Z_1$, $Z_2$, $Z_3$, $Z_4$, and $Z_5$;

or $R_d$ and $R_e$ can be taken together with the nitrogen to which they are attached to form a cycloheteroalkyl ring or a heteroaryl ring optionally substituted through available atoms with 1, 2, 3, 4 or 5 groups selected from $Z_1$, $Z_2$, $Z_3$, $Z_4$, and $Z_5$;

$Z_1$, $Z_2$, $Z_3$, $Z_4$ and $Z_5$ are the same or different and are independently selected from hydrogen, halo, alkyl, haloalkyl, polyhaloalkyl, alkoxy, alkoxyalkyl, carboxy, carboxyalkyl, haloalkoxy, polyhaloalkoxy, alkoxycarbonyl, alkoxycarbonylalkyl, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, oxo, hydroxyalkyl, nitro, cyano, amino, substituted amino, alkylamino, dialkylamino, thiol, alkylthio, arylthio, heteroarylthio, arylthioalkyl, C(O)H, alkylcarbonyl, arylcarbonyl, amido, arylaminocarbonyl, alkoxycarbonyl, aminocarbonyl, substituted aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, alkoxycarbonylamino, arylsulfinyl, arylsulfinylalkyl, arylsulfonyl, alkylsulfonyl, aminosulfinyl, aminosulfonyl, arylsulfonylamino, heteroarylcarbonylamino, heteroarylsulfinyl, heteroarylsulfonyl, alkylsulfinyl, sulfonamido, sulfonyl, amidino, guanidino,

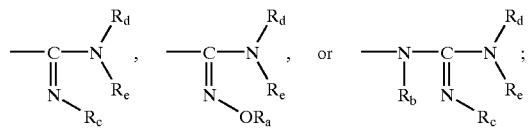

and wherein $R_4$ and $R_5$ can be taken together with the nitrogen to which they are attached to form a cycloheteroalkyl ring or a heteroaryl ring optionally substituted through available atoms with 1, 2, 3, 4 or 5 groups selected from $Z_1$, $Z_2$, $Z_3$, $Z_4$, and $Z_5$;

$R_5$ and $R_{11}$ can be taken together to form a heteroaryl ring optionally substituted through available atoms with 1, 2, 3, 4 or 5 groups selected from $Z_1$, $Z_2$, $Z_3$, $Z_4$, and $Z_5$;

$R_5$ or $R_4$ or $R_{11}$ or $R_{12}$ can form a ring with $R^6$ which can be a cycloheteroalkyl or a heteroaryl ring optionally substituted through available atoms with 1, 2, 3, 4 or 5 groups selected from $Z_1$, $Z_2$, $Z_3$, $Z_4$, and $Z_5$;

$R_{10}$ or $R_{10a}$ can combine with $R_8$ or $R_9$ on an adjacent carbon atom to form a saturated or unsaturated carbocyclic or heterocyclic ring optionally substituted through available atoms with 1, 2, 3, 4 or 5 groups selected from $Z_1$, $Z_2$, $Z_3$, $Z_4$, and $Z_5$;

$R_{10}$ and $R_{10a}$ groups on adjacent carbon atoms can combine to form a saturated or unsaturated carbocyclic or heterocyclic ring optionally substituted through available atoms with 1, 2, 3, 4 or 5 groups selected from $Z_1$, $Z_2$, $Z_3$, $Z_4$, and $Z_5$;

$R_{11}$ and $R_{12}$ can combine to form a saturated or unsaturated carbocyclic or heterocyclic ring optionally substituted through available atoms with 1, 2, 3, 4 or 5 groups selected from $Z_1$, $Z_2$, $Z_3$, $Z_4$, and $Z_5$.

Where one or more of $R_5$, $R_4$ or $R_6$ are H, then double bond isomers are possible which are included in the present invention.

Preferred are compounds of formula I wherein n is 1 to 4, more preferably 3 or 4;

$R_1$ and $R_2$ are each independently hydrogen, halogen or alkyl.

$R_3$ is selected from aryl (optionally substituted),

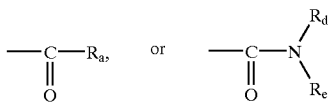

where $R_d$ and $R_e$ taken with the nitrogen to which they are attached form a 3 to 6-membered saturated ring (optionally substituted);

$R_6$ and $R_7$ are each H;

$R_8$, $R_9$, $R_{10}$ and $R_{10a}$ are each hydrogen;

or $R_{10}$ combines with one of $R_8$, or $R_9$ on an adjacent carbon atom, or combines with another $R_{10}$ on an adjacent carbon atom to form an unsaturated carbocylic ring.

$R_4$ is H or alkyl;

$R_5$ is H, alkyl, aryl, arylalkyl, heteroaryl, cycloheteroalkyl,

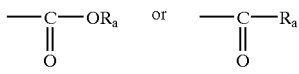

(any of which may be optionally substituted);

$R_{11}$ and $R_{12}$ are the same or different and are independently selected from hydrogen, carboxy, aryl, cyano, nitro, heteroaryl, —P(O)(OR$_a$)$_2$, —S(O)$_2$R$_a$, —C(O)R$_a$, —C(O)OR$_a$,

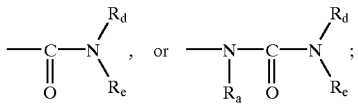

or $R_{11}$ and $R_{12}$ combine to form a saturated or unstaturated carbocyclic or heterocyclic ring (optionally substituted);

$R_a$ is hydrogen, aryl, alkyl, heteroaryl or cycloheteroalkyl (all optionally substituted);

$R_b$ is hydrogen or alkyl; and configuration at the chiral center is (S)— (as judged where $R^7$ is H).

More preferred are compounds wherein $R^3$ is selected from phenyl (optionally substituted),

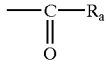

where $R_a$ is phenyl, phenylalkoxy, furyl, or thienyl (optionally substituted), and

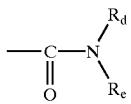

where $R_d$ and $R_e$ taken with the nitrogen to which they are attached form a 5-membered saturated ring (optionally substituted);

$R_5$ is (a) aryl, arylalkyl, or heteroaryl (each optionally independently substituted, especially with one or more groups selected from halogen, alkyl, haloalkyl, hydroxyalkyl, acyl, alkoxy, haloalkoxy, cyano, amino, aryl, oxo, —C(NH)NH$_2$, or —C(O)NH$_2$);

(b)

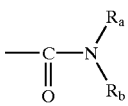

(especially where $R_a$ is hydrogen or alkyl, and $R_b$ is alkyl, aminocarbonyl, alkoxycarbonyl, aminocarbonylalkyl, carboxyalkyl, or hydroxyalkyl); and (c) C(O)R$_a$, or C(O)OR$_a$ (especially where $R_a$ is alkyl, alkenyl, hydroxyalkyl, cycloalkyl, cycloheteroalkyl, aryl or heteroaryl, any of which may be optionally substituted);

$R_{11}$ and $R_{12}$ are the same or different and are independently selected from hydrogen, nitro, carboxy, cyano, aryl, heteroaryl, —CO$_2$R$_{a1}$, —SO$_2$R$_{a1}$, —CONR$_{d1}$R$_{e1}$, and —C(O)R$_{a2}$ where $R_{a2}$ is alkyl, aryl or heteroaryl (each optionally substituted, preferrably with one or more alkoxy, alkyl or halogen), and $R_{a1}$ $R_{d1}$ and $R_{e1}$ are independently selected from hydrogen, alkyl, alkoxyalkyl, aryl and heteroaryl);

or $R_{11}$ and $R_{12}$ combine to form an optionally substituted ring of formula

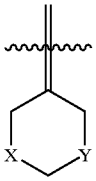

where X and Y are independently selected from NR$_a$ and O (especially where the ring is substituted with one or more alkyl or oxo groups).

In addition, in accordance with the present invention, a method for preventing, inhibiting or treating cardiovascular diseases associated with thromboses is provided, wherein a compound of formula I is administered in a therapeutically effective amount which inhibits Factor Xa.

DETAILED DESCRIPTION OF THE INVENTION

The following definitions apply to the terms as used throughout this specification, unless otherwise limited in specific instances.

Unless otherwise indicated, the term "lower alkyl", "alkyl" or "alk" as employed herein alone or as part of another group includes both straight and branched chain hydrocarbons, containing 1 to 40 carbons (in the case of alkyl or alk), preferably 1 to 20 carbons, more preferably 1 to 12 carbons (in the case of lower alkyl), in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various additional branched chain isomers thereof, and the like as well as such groups including 1 to 5 substituents independently selected from $Z_1$ through $Z_5$.

Unless otherwise indicated, the term "cycloalkyl" as employed herein alone or as part of another group includes saturated or partially unsaturated (containing 1 or 2 double bonds and/or 1 or 2 triple bonds) cyclic hydrocarbon groups containing 1 to 3 rings, including monocyclicalkyl, bicyclicalkyl and tricyclicalkyl, containing a total of 3 to 20 carbons forming the rings, preferably 4 to 12 carbons, forming the ring and which may be fused to one aromatic ring as described for aryl, which include cyclopropyl, cyclobutyl, cyclopentyl, cyclohexyl, cycloheptyl, cyclooctyl, cyclodecyl and cyclododecyl, cyclohexenyl,

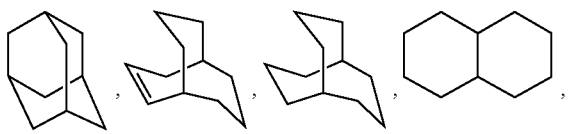

cyclopentenyl, cyclohexenyl, cycloheptenyl, cyclooctenyl, cyclohexadienyl, cycloheptadienyl, cyclopentynyl, cyclohexynyl, cycloheptynyl, cyclooctynyl, any of which groups may be optionally substituted with such groups including 1 to 5 substituents independently selected from $Z_1$ through $Z_5$.

The term "cycloalkenyl" and "cycloalkynyl" as employed herein alone or as part of another group refers to cyclic hydrocarbons containing 5 to 20 carbons, preferably 6 to 12 carbons and 1 or 2 double bonds or 1 or 2 triple bonds, respectively. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "polycycloalkyl" as employed herein alone or as part of another group refers to a bridged multicyclic group containing 5 to 20 carbons and containing 0 to 3 bridges, preferably 6 to 12 carbons and 1 or 2 bridges. Exemplary polycycloalkyl groups include [3.3.0]-bicyclooctanyl, adamantanyl, [2.2.1]-bicycloheptanyl, [2.2.2]-bicyclooctanyl and the like and may be optionally substituted as defined for cycloalkyl.

The term "polycycloalkenyl" and "polycycloalkynyl" as employed herein alone or as part of another group refers to a bridged multicyclic group containing 5 to 20 carbons and containing 0 to 3 bridges and containing 1 or 2 double bonds, and/or 1 or 2 triple bonds, preferably 6 to 12 carbons and 1 or 2 bridges. Exemplary polycycloalkyl groups include [3.3.0]-bicyclooctenyl, [2.2.1]-bicycloheptenyl, [2.2.2]-bicyclooctenyl, [3.2.1]-bicyclooctenyl, and the like and may be optionally substituted as defined for cycloalkyl.

The term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example

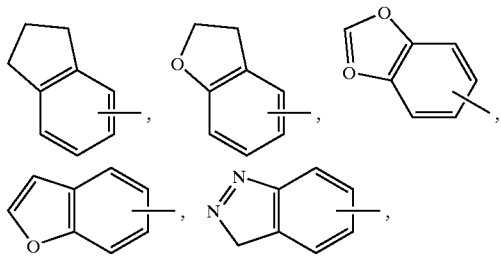

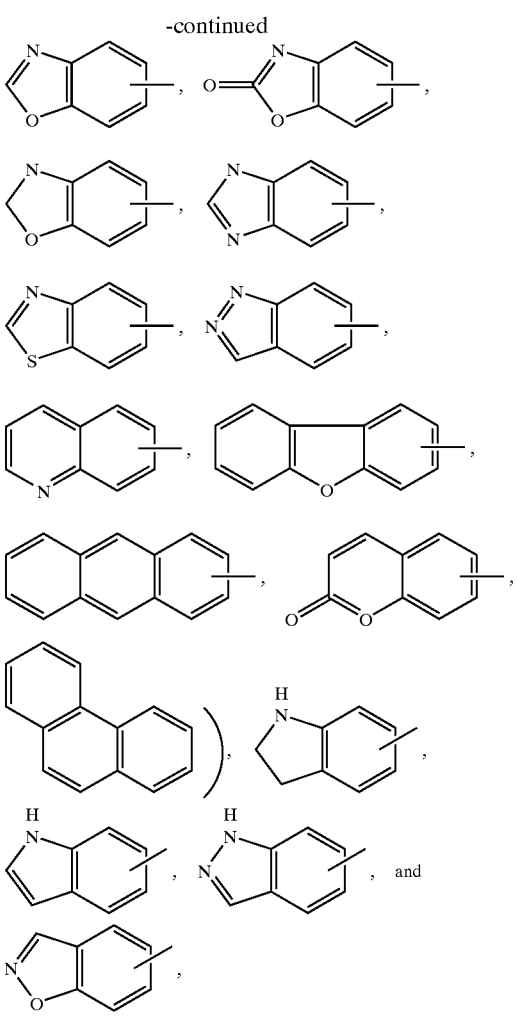

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonyl-aminocarbonyl or such groups including 1 to 5 substituents independently selected from $Z_1$ through $Z_5$.

The term "aralkyl", "aryl-alkyl" or "aryllower alkyl" as used herein alone or as part of another group refers to alkyl groups as discussed above having an aryl substituent, such as benzyl or phenethyl, or naphthylpropyl, or an aryl as defined above.

The term "lower alkoxy", "alkoxy", "aryloxy" or "aralkoxy" as employed herein alone or as part of another group includes any of the above alkyl, aralkyl or aryl groups linked to an oxygen atom.

The term "substituted amino" as employed herein alone or as part of another group refers to amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. These substituents may be further substituted with a carboxylic acid or such groups including 1 to 5 substituents independently selected from $Z_1$ through $Z_5$. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

The term "lower alkylthio", alkylthio", "arylthio" or "aralkylthio" as employed herein alone or as part of another group includes any of the above alkyl, aralkyl or aryl groups linked to a sulfur atom.

The term "lower alkylamino", "alkylamino", "arylamino", or "arylalkylamino" as employed herein alone or as part of another group includes any of the above alkyl, aryl or arylalkyl groups linked to a nitrogen atom.

The term "acyl" as employed herein by itself or part of another group, as defined herein, refers to an organic radical linked to a carbonyl

group; examples of acyl groups include any of the $R^1$ groups attached to a carbonyl, such as alkanoyl, alkenoyl, aroyl, aralkanoyl, heteroaroyl, cycloalkanoyl, cycloheteroalkanoyl and the like.

The term "alkanoyl" as used herein alone or as part of another group refers to alkyl linked to a carbonyl group.

Unless otherwise indicated, the term "lower alkenyl", or "alkenyl" as used herein by itself or as part of another group refers to straight or branched chain radicals of 2 to 20 carbons, preferably 3 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, alkylthio or such groups including 1 to 5 substituents independently selected from $Z_1$ through $Z_5$.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, or any of the $R^1$ groups, or such groups including 1 to 5 substituents independently selected from $Z_1$ through $Z_5$.

The terms "arylalkenyl" and "arylalkynyl" as used alone or as part of another group refer to alkenyl and alkynyl groups as described above having an aryl substituent.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

Suitable alkylene, alkenylene or alkynylene groups $(CH_2)_p$ (where, p is 1 to 8, preferably 1 to 5 which may include alkylene, alkenylene or alkynylene groups) as defined herein, may optionally include 1 to 5 substituents independently selected from $Z_1$ through $Z_5$.

Examples of alkylene, alkenylene and alkynylene include

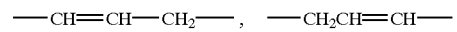

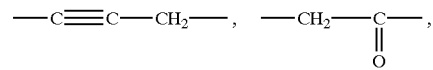

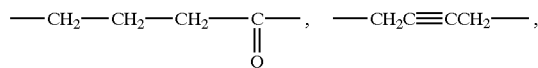

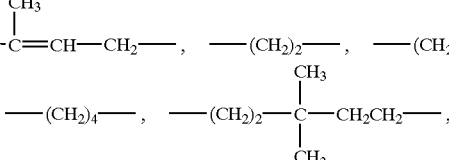

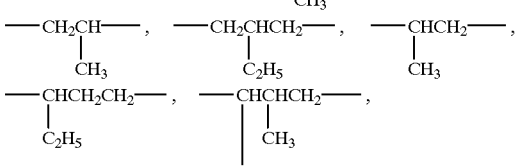

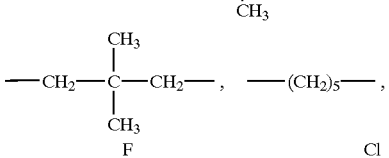

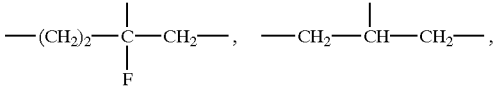

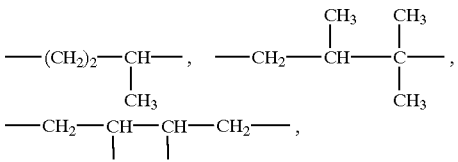

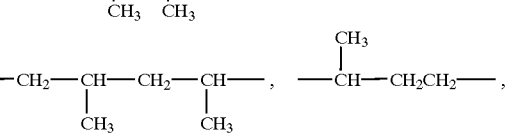

-continued

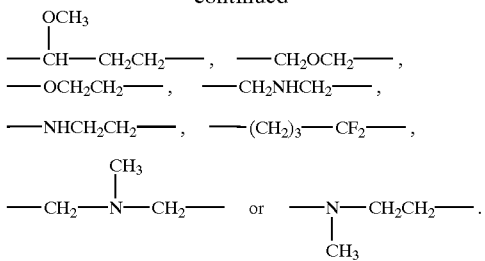

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

The term "heterocyclo" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (which is defined above), such as

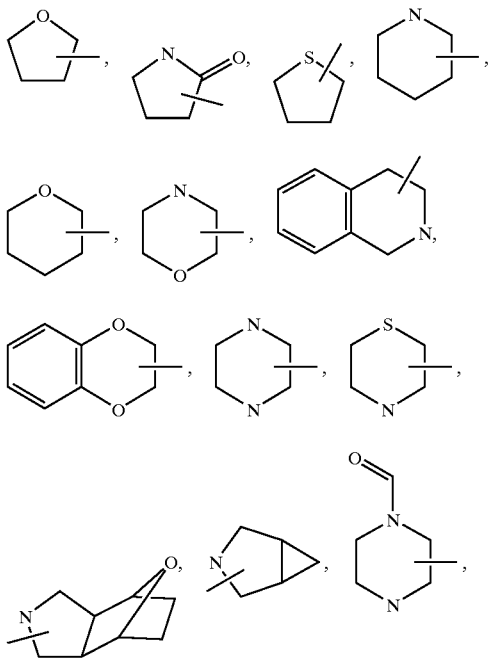

and the like. The above groups may include 1 to 4 substituents such as alkyl, halo, oxo and/or any of of the $R^1$ groups, or such groups including 1 to 5 substituents independently selected from $Z_1$, through $Z_5$. In addition, any of the above rings can be fused to a cycloalkyl, aryl, heteroaryl or heterocyclo ring.

The term "heteroaryl" as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides. The heteroaryl group may optionally include 1 to 5 substituents such as groups including 1 to 5 substituents independently selected from $Z_1$ through $Z_5$. Examples of heteroaryl groups include the following:

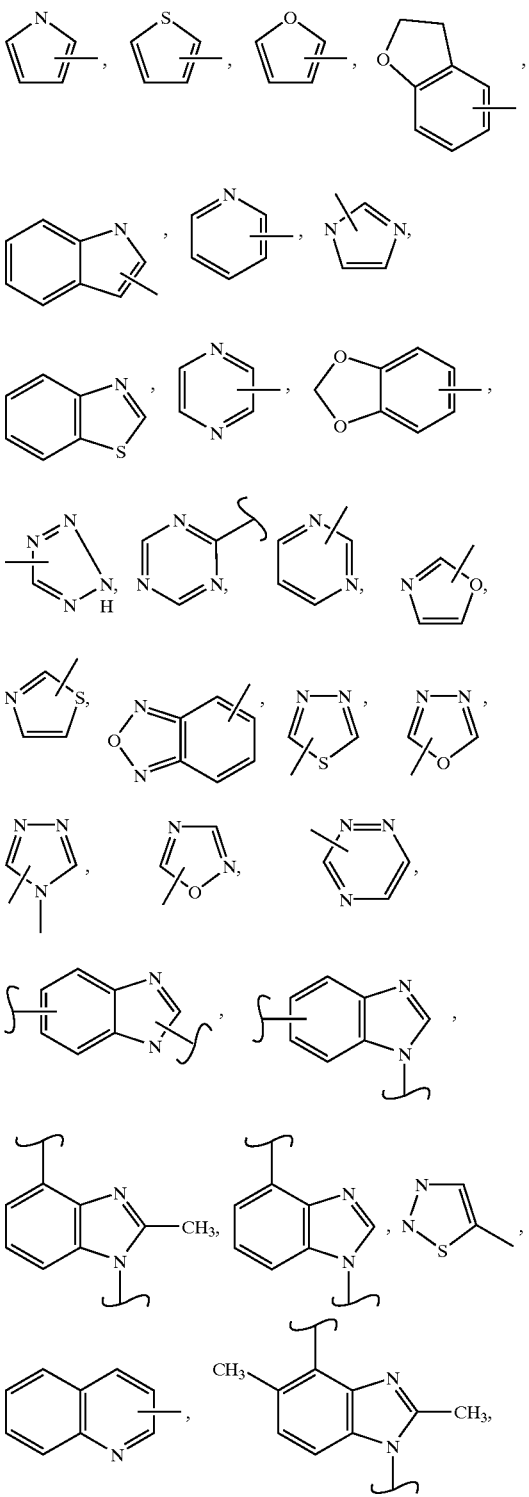

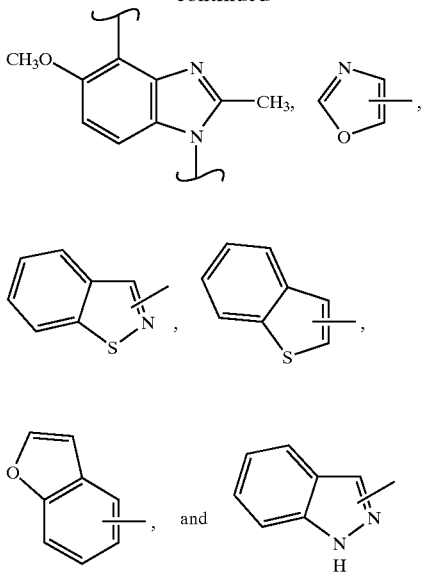

The term "heterocycloalkyl", "polycycloalkylalkyl", "polycycloalkenylalkyl" or "polycycloalkynylalkyl" as used herein alone or as part of another group refers to heterocyclo groups, polycycloalkyl groups, polycycloalkenyl groups or polycycloalkynyl groups as defined above linked through a C atom or heteroatom to a $(CH_2)_p$ chain, alkylene, alkenylene or alkynylene as defined above.

The term "heteroarylalkyl" as used herein alone or as part of another group refers to a heteroaryl group as defined above linked through a C atom or heteroatom to a —$(CH_2)_p$— chain, alkylene or alkenylene or alkynylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The term "amido" as used herein refers to the group

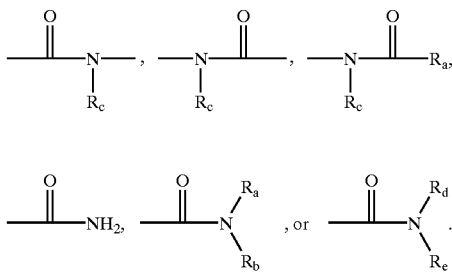

The term "sulfonamido" as used herein refers to the group

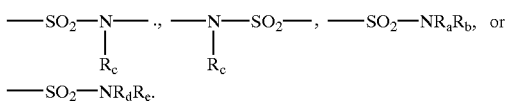

The compounds of formula I can be present as salts, in particular pharmaceutically acceptable salts. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$–$C_4$)-alkyl- or aryl-sulfonic acids which are unsubstituted or substituted, for example by halogen, for example methane- or p-toluene-sulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylamine, or a mono-, di- or trihydroxy lower alkylamine, for example mono-, di- or triethanolamine. Corresponding internal salts may furthermore be formed. Salts which are unsuitable for pharmaceutical uses but which can be employed, for example, for the isolation or purification of free compounds I or their pharmaceutically acceptable salts, are also included.

Preferred salts of the compounds of formula I include monohydrochloride, hydrogensulfate, methanesulfonate, phosphate or nitrate.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When enantiomeric or diastereomeric products are prepared, they can be separated by conventional methods for example, chromatographic or fractional crystallization.

It should be understood that the present invention includes prodrug forms of the compounds of formula I such as alkylesters of acids or any known prodrugs for lactam derivatives.

The compounds of the instant invention may, for example, be in the free or hydrate form, and may be obtained by methods exemplified by the following descriptions.

The compounds of formula I may be prepared by the exemplary processes described in the following reaction schemes. Exemplary reagents and procedures for these reactions appear hereinafter and in the working Examples.

Compounds of Formula I of the invention can be prepared from compounds of formula II as shown in the following schemes 1–7.

Scheme 1

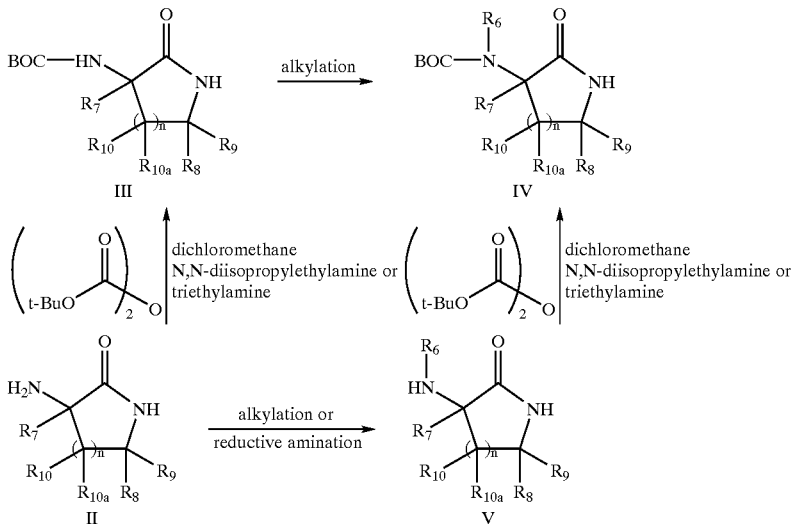

Compound II is converted to III by protection and then III is converted to IV by substitution. Alternatively, compound II may be converted to compound V and then compound V may be protected to provide IV. The BOC protecting group is shown, however other groups such as CBZ or trifluoroacetyl may be used in place of the BOC-group.

Scheme 2

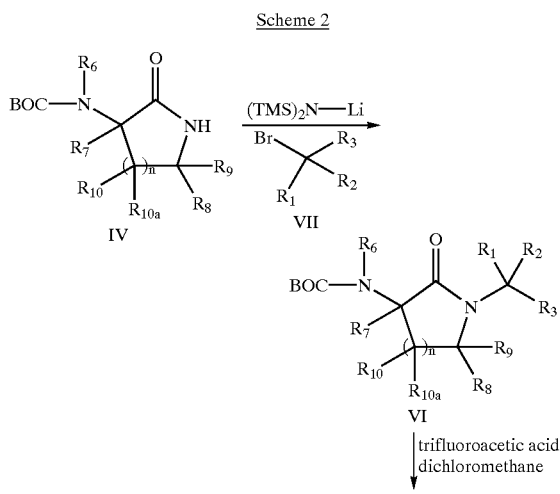

-continued

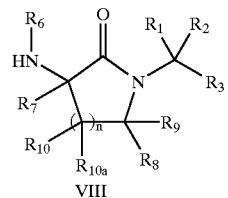

Compound IV is then converted to compound VI by alkylation with an appropriate halide VII. The protecting group is then removed from VI to provide VIII. Compounds of type VIII can then be converted to compounds of type I as shown in scheme 5 or scheme 6.

Compounds of formula VIII wherein $R_3$ is the group

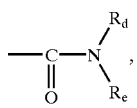

can be prepared according to the procedures outlined in schemes 3 and 4.

Scheme 3

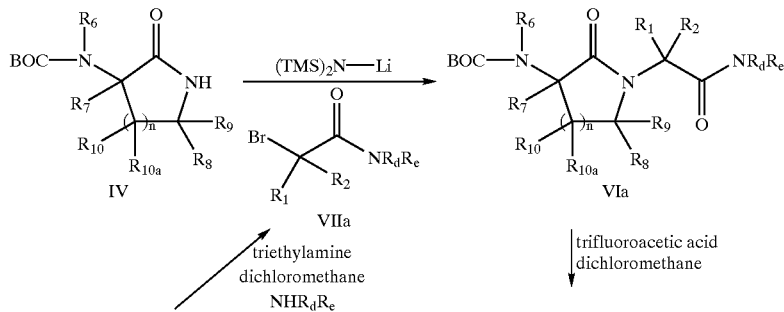

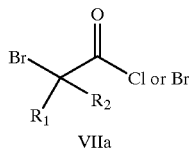
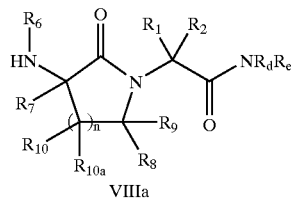

Compound IV is converted to compound VIa by alkylation with haloamide VIIa. Haloamide VIIa is obtained from bromoacetyl bromide or bromoacetyl chloride by acylation under standard conditions.

an intermediate which is reacted with compound VIII in the presence of mercuric chloride (or a similar salt) to provide compounds of type I. Other agents to promote the coupling reaction such as WSC may also be used. Other Scheme 4

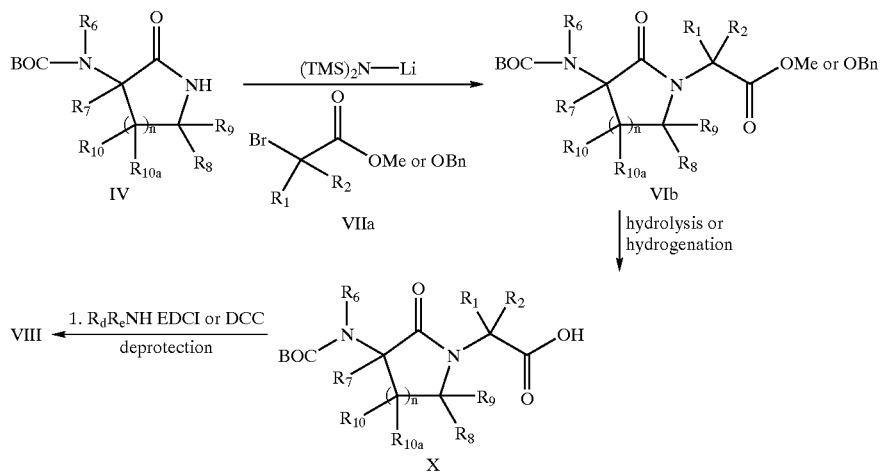

Alkylation of compound IV with a halo ester provides compound VIb. Compound VIb is then converted to compound X by hydrolysis or hydrogenation. Compound X is then converted to VIII by any number of methods, such as reaction with an amine and a coupling agent such as DCC or WSC (vide infra for list of abbreviations) followed by BOC (or other protecting group) removal.

bases such as N,N-diisopropylethylamine can be used in place of NaH.

Scheme 6

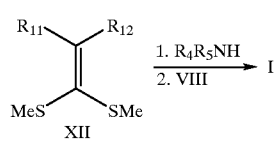

An alternative route involves the reaction of a compound of type XII sequentially with an appropriate amine and compound VIII A final route to compounds of type I, shown in scheme 7 involves the conversion of a compound of type VIII (wherein $R_6$=H) to a compound of type XIII and conversion of this compound to compounds of type I as previously described.

Scheme 5

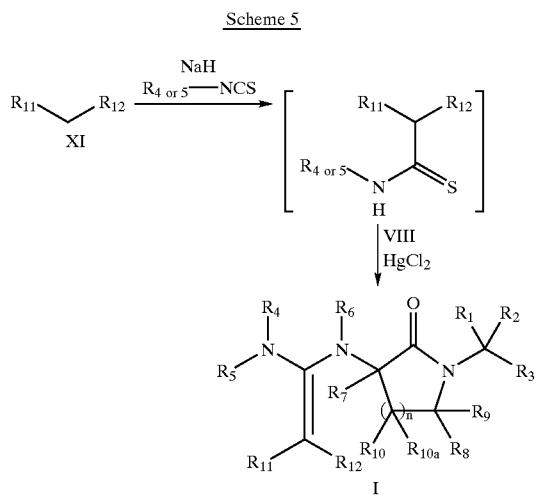

Reaction of a compound of type XI with a base such as sodium hydride and then with an isothiocyanate provides Scheme 7

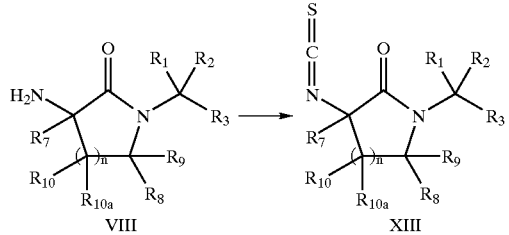

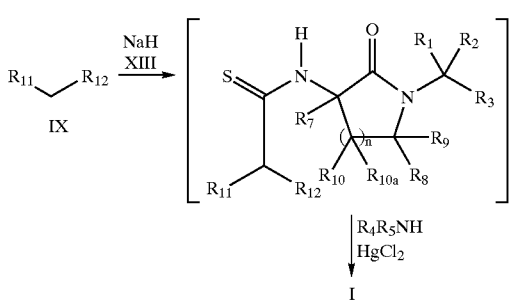

Other methods used in the preparation of compounds of the invention are known to those skilled in the art and are not further described.

The compounds of the present invention are inhibitors of the activated coagulation serine protease known as Factor Xa and thus are useful to maintain the fluidity of blood. Addtionally, compounds of the present invention are useful for the treatment or prophylaxis of Factor Xa-associated disorders. As used herein, the term "Factor Xa-associated disorder" refers to any disorder which may be prevented, partially alleviated or cured by the administration of a Factor Xa inhibitor. Thus, the compounds of the present invention are useful in the treatment or prevention of various Factor Xa-associated disorders including: Thrombotic or thromboembolic conditions; acute coronary syndromes (such as coronary artery disease, myocardial infarction (MI), unstable angina and non-Q Wave MI); thromboembolic stroke (such as that resulting from atrial fibrillation or from ventricular mural thrombus (low ejection fraction)); venous thrombosis (including deep vein thrombosis); arterial thrombosis; cerebral thrombosis; pulmonary embolism; cerebral embolism; peripheral occlusive arterial disease (e.g., peripheral arterial disease, intermittent claudication, critical leg ischemia, prevention of amputation, prevention of cardiovascular morbidity such as MI, stroke or death); thromboembolic consequenses of surgery, interventional cardiology or immobility; thromboembolic consequenses of medication (such as oral contraceptives, horomme replacement and heparin); thrombotic consequenses of atherosclerotic vascular disease and atherosclerotic plaque rupture leading to tissue ischemia; prevention of atherosclerotic plaque formation; transplant atherosclerosis; thromboembolic complications of pregancy including fetal loss; thromboembolic consequences of thrombophilia (e.g., Factor V Leiden, and homocystinenimia); prothrombotic consequences and/or complications of cancer; prevention of thrombosis on artificial surfaces (such as stents, blood oxygenators, shunts, vascular access ports, vascular grafts, artificial valves, etc.); coagulopathies (e.g., disseminated intravascular coagulation (DIC)); coagulation syndromes; vascular remodeling atherosclerosis, restenosis and systemic infection; prevention of metastesis and tumor implantation; diabetic complications including retinopathy, nephropathy and neuropathy; inflammation; ischemia (such as that resulting from vascular occlusion, cerebral infarction, stroke and related cerebral vascular diseases); Kasabach-Merritt syndrome; atrial fibrillation; ventricular enlargement (including dilated cardiac myopathy and heart failure); restenosis (e.g., following arterial injury-induced either endogenously or exogenously).

Compounds of the present invention may additionally be useful as diagnostic agents and adjuncts. For example, the present compounds may be useful in maintaining whole and fractionated blood in the fluid phase such as required for analytical and biological testing. In addition, the compounds of the present invention may be useful for maintaining blood vessel patency in conjunction with vascular surgery including bypass grafting, arterial reconstruction, atherectomy, vascular graft and stent patency, organ, tissue and cell implantation and transplantation. In addition, the compounds of the present invention may be useful for maintaining blood vessel patency in conjunction with interventional cardiology or vascular surgery including bypass grafting, arterial reconstruction, atherectomy, vascular graft and stent patency, organ, tissue and cell implantation and transplantation.

The compounds of the present invention may be used in combination with each other, or with other Factor Xa inhibitors. Additionally, the present compounds may be used in combination with one or more of various other therapeutic agents, including: anti-arrythmic agents; anti-hypertensive agents; anti-platelet agents, anti-thrombotic and/or anti-thrombolytic agents; calcium channel blockers (L-type and T-type); cardiac glycosides; diruetics, mineralocorticoid receptor antagonists; phospodiesterase inhibitors; cholesterol/lipid lowering agents and lipid profile therapies; anti-diabetic agents; anti-depressants; anti-inflammatory agents (steroidal and non-steroidal); anti-osteoporosis agents; hormone replacement therapies; oral contraceptives; anti-coagulants; anti-obesity agents; anti-anxiety agents; anti-proliferative agents; anti-tumor agents; anti-ulcer and gastroesophageal reflux disease agents; growth hormone and/or growth hormone secretagogues; thyroid mimetics (including thyroid receptor antagonist); anti-infective agents; anti-viral agents; anti-bacterial agents; and anti-fungal agents.

Examples of suitable anti-arryhtmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil) ; K$^+$ channel openers such as $I_{Ach}$ inhibitors, and $I_{Kur}$ inhibitors (e.g., compounds such as those disclosed in U.S. application Ser. No. 09/729,731, filed Dec. 5, 2000 (attorney docket HA 726)).

Examples of suitable anti-hypertensive agents for use in combination with the compounds of the present invention include: alpha adrenergic blockers; beta adrenergic blockers; calcium channel blockers (e.g. diltiazem, verapamil, nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., omapatrilat, gemopatrilat and nitrates).

Examples of suitable anti-platelet agents for use in combination with the compounds of the present invention include: GPIIb/IIIa blockers (e.g., abciximab, eptifibatide, tirofiban); P2Y$_{12}$ antagonists (e.g., clopidogrel, ticlopidine, CS-747); thromboxane receptor antagonists (e.g., ifetroban);

aspirin; and PDE-III inhibitors (e.g., dipyridamole) with or without aspirin.

Examples of suitable anti-thrombotic and/or anti-thrombolytic agents for use in combination with the compounds of the present invention include: tissue plasminogen activator (natural or recombinant), tenecteplase (TNK), and lanoteplase (nPA); factor VIIa inhibitors; factor Xa inhibitors; thrombin inhibitors (such as hirudin and argatroban); PAI-1 inhibitors (i.e., inactivators of tissue plasminogen activator inhibitors); alpha2-antiplasmin inhibitors; streptokinase, urokinase and prourokinase; and anisoylated plasminogen streptokinase activator complex.

Examples of suitable calcium channel blockers (L-type or T-type) for use in combination with the compounds of the present invention include diltiazem, verapamil, nifedipine, amlodipine and mybefradil.

Examples of suitable cardiac glycosides for use in combination with the compounds of the present invention include digitalis and ouabain.

Examples of suitable diruetics for use in combination with the compounds of the present invention include: chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone.

Examples of suitable mineralocorticoid receptor antagonists for use in combination with the compounds of the present invention include sprionolactone and eplirinone.

Examples of suitable phospodiesterase inhibitors for use in combination with the compounds of the present invention include: PDE III inhibitors (such as cilostazol); and PDE V inhibitors (such as sildenafil).

Examples of suitable cholesterol/lipid lowering agents and lipid profile therapies for use in combination with the compounds of the present invention include: HMG-CoA reductase inhibitors (e.g., pravastatin lovastatin, atorvastatin, simvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; choesterol absorption inhibitors; and cholesterol ester transfer protein inhibitors (e.g., CP-529414).

Examples of suitable anti-diabetic agents for use in combination with the compounds of the present invention include: biguanides (e.g. metformin); glucosidase inhibitors (e.g. acarbose); insulins (including insulin secretagogues or insulin sensitizers); meglitinides (e.g. repaglinide); sulfonylureas (e.g., glimepiride, glyburide and glipizide); biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000 (attorney docket LA27), glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protien tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congugated estrogens) and estradiol.

Examples of suitable anti-coagulants for use in combination with the compounds of the present invention include heparins (e.g., unfractioned and low molecular weight heparins such as enoxaparin and dalteparin).

Examples of suitable anti-obesity agents for use in combination with the compounds of the present invention include orlistat and aP2 inhibitors (such as those disclosed in U.S. Ser. No. 09/519,079 filed Mar. 6, 2000 (attorney docket LA27)).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, FK 506, and adriamycin.

Examples of suitable anti-tumor agents for use in combination with the compounds of the present invention include paclitaxel, adriamycin, epithilones, cisplatin, and carboplatin.

Examples of suitable anti-ulcer and gastroesophageal reflux disease agents for use in combination with the compounds of the present invention include famotidine, ranitidine, and omeprazole.

The various other therapeutic agents described above may be employed in the same dosage form with the compound of formula I or in different dosage forms, in dosages and regimens as generally known in the art or in the PDR.

The compounds of the present invention may act in a synergistic fashion with one or more of the above agents to prevent reocclusion following a successful thrombolytic therapy and/or reduce the time to reperfusion. The compounds of the present invention may also allow for reduced doses of the thrombolytic agent to be used and therefore minimize potential hemorrhagic side-effects.

The compounds of the present invention may also inhibit other serine proteases, for example, thrombin, Factor VIIa, urokinase-type plasminogen activator (urokinase), tryptase and/or trypsin. As a result, these compounds may additionally be useful as angiogenesis inhibitors in the treatment of cancer, as antiinflammatory agents particularly in the treatment of chronic asthma and in the treatment or prevention of allergic rhinitis, rheumatoid arthritis, inflammatory bowel disease, psoriasis, and conjunctivitis and in the treatment or prevention of pancreatitis.

The compounds of the invention can be administered orally or parenterally such as subcutaneously or intravenously, as well as by nasal application, rectally or sublingually to various mammalian species known to be subject to such maladies, e.g., humans, cats, dogs and the like in an effective amount within the dosage range of about 0.1 to about 500 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

The active substance can be utilized in a composition such as tablet, capsule, solution or suspension or in other type carrier materials such as transdermal devices, iontophoretic devices, rectal suppositories, inhalant devices and the like. The composition or carrier will contain about 5 to about 500 mg per unit of dosage of a compound or mixture of compounds of formulas I. They may be compounded in conventional matter with a physiologically acceptable vehicle or carrier, excipient, binder, preservative, stabilizer, flavor, etc., as called for by accepted pharmaceutical practice.

The following working Examples represent preferred embodiments of the present invention.

General Experimental Information: HPLC was carried out using one of the following methods:

method A: column—YMC-pack ODS-A C-18, 4.6×50 mm S-5, 120 A; flow-4.0 mL/min; detection at 220 nm; solvent-A=90:10 water:methanol (+0.2% phosphoric acid), B 10:90 water:methanol (+0.2% phosphoric acid); gradient-linear, 0% B to 100% B over 4 min and hold at 100 % B for 1 min.

method B: column—Phenomenex-LUNA C-18, 4.6×50 mm, S-5; flow-4.0 mL/min; detection at 220 nm; solvent-A=90:10 water:methanol (+0.2% phosphoric acid), B=10:90 water:methanol (+0.2% phosphoric acid); gradient-linear, 0% B to 100% B over 4 min and hold at 100 % B for 1 min.

method C: column—YMC ODS-A, C-18, 4.6×50 mm, S-5, 120 A; flow-4 mL/min; detection at 220 nm; gradient-linear; 0% B to 100% B over 4 minutes; solvent-A= methanol:water:TFA; 10:90:0.1, B=methanol:water:TFA; 90:10:0.1.

For preparative (RP) HPLC chromatography, the following were used as solvents: A=90:10 water:methanol (with 0.1% TFA); B=10:90 water:methanol (with 0.1% TFA)

List of Abbreviations used:
 DMAP=N,N-dimethyl-4-pyridinamine
 SCX=strong cation exchange
 TFA=trifluoroacetic acid
 TFFH=N-[(dimethylamino)fluoromethylene]-N-methylmethanaminium hexafluorophosphate
 TMEDA=N,N,N',N'-tetramethylethylenediamine
 WSC=1-(3-(dimethylamino)propyl)-3-ethylcarbodiimide hydrochloride

EXAMPLE 1

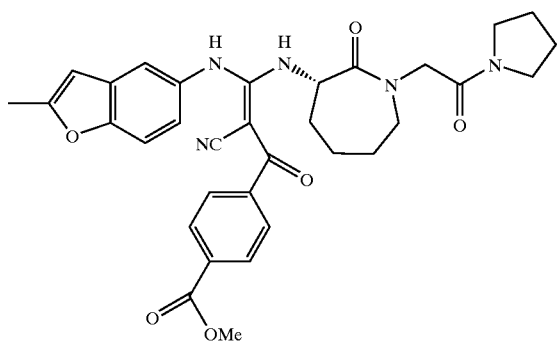

4-[2-Cyano-3-[[(3S)-hexahydro-2-oxo-1-[2-oxo-2-(1-pyrrolidinyl)ethyl]-1H-azepin-3-yl]amino]-3-[(2-methyl-5-benzofuranyl)amino]-1-oxo-2-propenyl]benzoic Acid Methyl Ester To a solution of methyl 4-(cyanoacetyl)benzoate (0.304 g, 1.50 mmol) in DMF (2 mL) was added sodium hydride (68.0 mg, 2.25 mmol). The reaction mixture was stirred at room temperature for 30 min. To the solution was then added 5-isothiocyanato-2-methylbenzofuran (0.284 g, 1.50 mmol). The reaction mixture was stirred at room temperature for 3 h at which time 1-[[(3S)-3-aminohexahydro-2-oxo-1H-azepin-1-yl]acetyl]pyrrolidine (0.358, 1.50 mmol) and mercury (II) chloride (0.407 g, 1.50 mmol) were added. The reaction mixture was stirred for another 30 min. The reaction mixture was passed through CELITE and diluted with 50 mL of ethyl acetate. The organic solution was washed 2×25 mL with brine and was concentrated in vacuo. The residue was purified by flash chromatography (silica, 4% methanol/ethyl acetate) to give the title compound as yellow solid (0.442 g, 49% yield): HPLC (method A) $t_R$ 4.1 min; MS (ESI, pos. ion spectrum) m/z 598 (M+H).

EXAMPLE 2

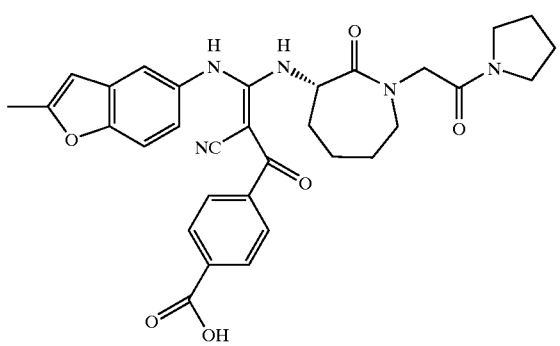

4-[2-Cyano-3-[[(3S)-hexahydro-2-oxo-1-[2-oxo-2-(1-pyrrolidinyl)ethyl]-1H-azepin-3-yl]amino]-3-[(2-methyl-5-benzofuranyl)amino]-1-oxo-2-propenyl]benzoic Acid The compound of Example 1 (0.442g, 0.740 mmol) was dissolved in 10 mL of 1:1 water:THF and the mixture was cooled to 0° C. To the solution was added LiOH monohydrate (0.31 g, 7.4 mmol). The reaction mixture was allowed to come to room temperature. After stirring for 24 h, the reaction mixture was concentrated by in vacuo and the residue was dissolved in methylene chloride. The mixture was extracted 2×25 mL with water. The combined aqueous layers were neutralized with 1 N HCl to pH 4 and were extracted 2×25 mL with ethyl acetate. The combined ethyl acetate layers were dried over sodium sulfate and concentrated to give the title compound (360 mg, 83%) as yellow solid: MS (ESI, pos. ion) m/z 584 (M+H); HPLC (method B) $t_R$=3.8 min, purity: >96%.

EXAMPLE 3

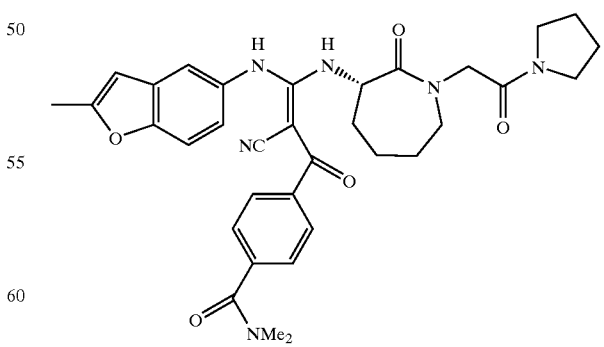

4-[2-Cyano-3-[[(3S)-hexahydro-2-oxo-1-[2-oxo-2-(1-pyrrolidinyl)ethyl]-1H-azepin-3-yl]amino]-3-[(2-methyl-5-benzofuranyl)amino]-1-oxo-2-propenyl]-N,N-dimethylbenzamide The compound of Example 2 (59 mg, 0.10 mmol) was dissolved in 1 mL of acetonitrile. To the solution was added TFFH (26.4 mg, 0.10 mmol) and triethylamine (0.016 mL, 0.11 mmol). The reaction mixture was stirred at room temperature for 30 min and then 2 M dimethyl amine in THF (0.060 mL, 0.12 mmol) was added. The reaction mixture was stirred at room temperature for an additional 2 h. The reaction mixture was loaded onto a SCX cartridge (prewashed with methanol and then acetonitrile). The column was eluted with acetonitrile, 1/1 acetonitrile/methanol and methanol to provide the title compound (44 mg, 72%) as a white solid: MS (ESI, pos. ion spectrum) m/z 611 (M+H); HPLC (method B) $t_R$ 3.7 min, purity 100%.

EXAMPLES 4–19

Using the same methodology described in Examples 1–3, the following compounds were prepared with the following modification: After SCX purification, final compounds were purified by preparative reverse phase chromatography (YMC C-18 column; linear gradient elution).

| Ex. | Structure | Name | Characterization |
|---|---|---|---|
| 4 | 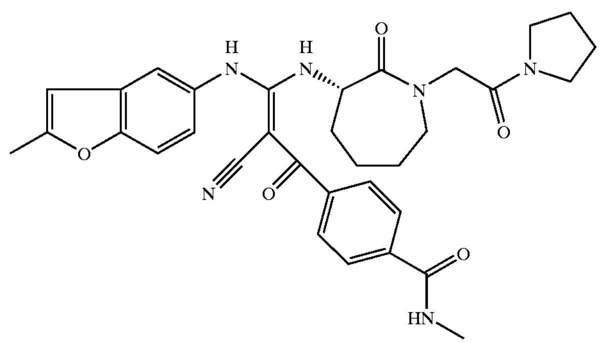 | 4-[2-Cyano-3-[[(3S)-hexahydro-2-oxo-1-[2-oxo-2-(1-pyrrolidinyl)ethyl]-1H-azepin-3-yl]amino]-3-[(2-benzofuranyl)amino]-1-oxo-2-propenyl]-N-methylbenzamide | HPLC (method B) $t_R$ 3.6 min; MS (ESI, pos. ion spectrum) m/z 597 |
| 5 | 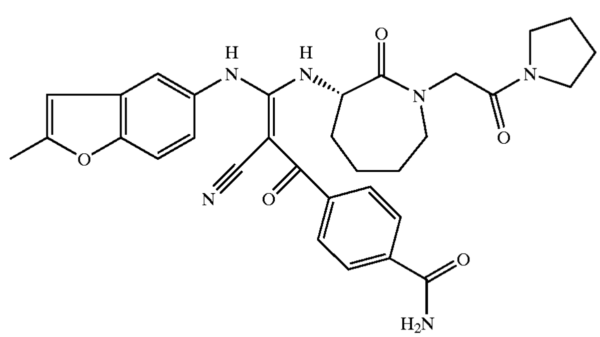 | 4-[2-Cyano-3-[[(3S)-hexahydro-2-oxo-1-[2-oxo-2-(1-pyrrolidinyl)ethyl]-1H-azepin-3-yl]amino]-3-[(2-methyl-5-benzofuranyl)amino]-1-oxo-2-propenyl]benzamide | HPLC (method B) $t_R$ 3.5 min; MS (ESI, pos. ion spectrum) m/z 583 |
| 6 | 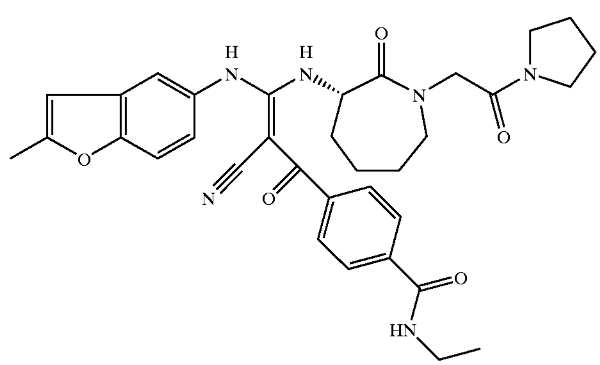 | 4-[2-Cyano-3-[[(3S)-hexahydro-2-oxo-1-[2-oxo-2-(1-pyrrolidinyl)ethyl]-1H-azepin-3-yl]amino]-3-[(2-methyl-5-benzofuranyl)amino]-1-oxo-2-propenyl]-N-ethylbenzamide | HPLC (method B) $t_R$ 3.7 min; MS (ESI, pos. ion spectrum) m/z 611 |

-continued

| Ex. | Structure | Name | Characterization |
|---|---|---|---|
| 7 | 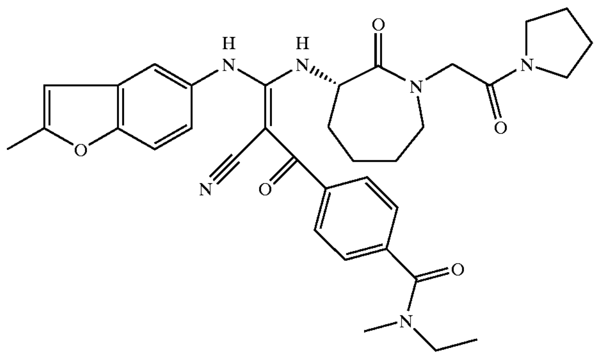 | 4-[2-Cyano-3-[[(3S)-hexahydro-2-oxo-1-[2-oxo-2-(1-pyrrolidinyl)ethyl]-1H-azepin-3-yl]amino]-3-[(2-methyl-5-benzofuranyl)amino]-1-oxo-2-propenyl]-N-ethyl-N-methylbenzamide | HPLC (method B) $t_R$ 3.8 min; MS (ESI, pos. ion spectrum) m/z 625 |
| 8 | 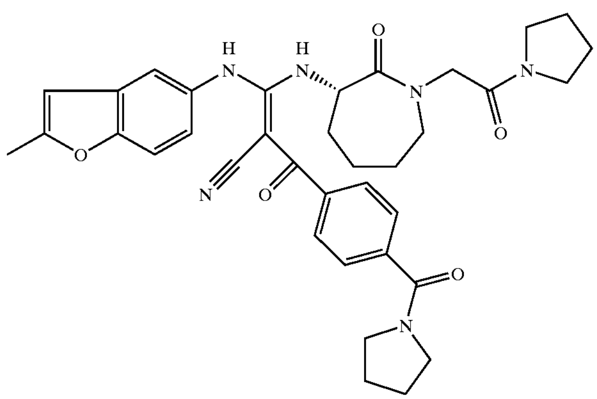 | 1-[[(3S)-3-[[2-Cyan-1-[(2-methyl-5-benzofuranyl)amino]-3-oxo-3-[4-(1-pyrrolidinylcarbonyl)phenyl]-1-propenyl]amino]hexahydro-2-oxo-1H-azepin-1-yl]acetyl]pyrrolidine | HPLC (method B) $t_R$ 3.8 min; MS (ESI, pos. ion spectrum) m/z 637 |
| 9 | 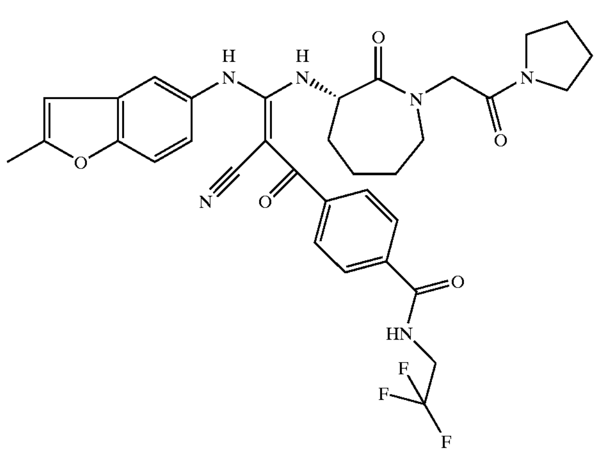 | 4-[2-Cyano-3-[[(3S)-hexahydro-2-oxo-1-[2-oxo-2-(1-pyrrolidinyl)ethyl]-1H-azepin-3-yl]amino]-3-[(2-methyl-5-benzofuranyl)amino]-1-oxo-2-propenyl]-N-(2,2,2-trifluoroethyl)benzamide | HPLC (method B) $t_R$ 3.9 min; MS (ESI, pos. ion spectrum) m/z 665 |

| Ex. | Structure | Name | Characterization |
|---|---|---|---|
| 10 | 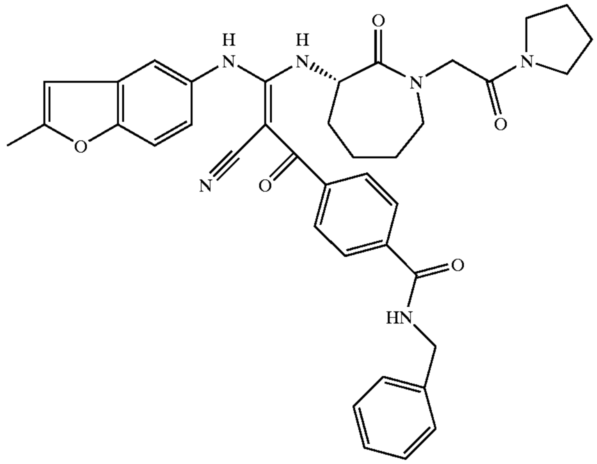 | 4-[2-Cyano-3-[[(3S)-hexahydro-2-oxo-1-[2-oxo-2-(1-pyrrolidinyl)ethyl]-1H-azepin-3-yl]amino]-3-[(2-methyl-5-benzofuranyl)amino]-1-oxo-2-propenyl]-N-(phenylmethyl)benzamide | HPLC (method B) t_R 4.0 min; MS (ESI, pos. ion spectrum) m/z 673 |
| 11 | 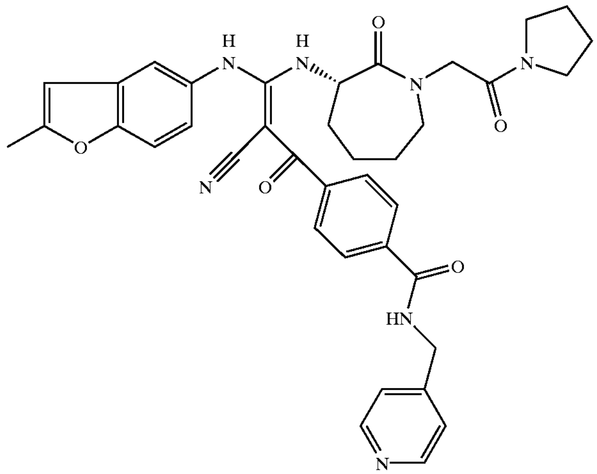 | 4-[2-Cyano-3-[[(3S)-hexahydro-2-oxo-1-[2-oxo-2-(1-pyrrolidinyl)ethyl]-1H-azepin-3-yl]amino]-3-[(2-methyl-5-benzofuranyl)amino]-1-oxo-2-propenyl]-N-(4-pyridinylmethyl) benzamide | HPLC (method B) t_R 3.2 min; MS (ESI, pos. ion spectrum) m/z 674 |
| 12 | 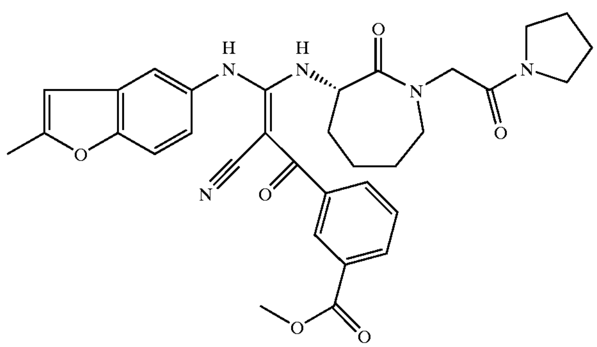 | 3-[2-Cyano-3-[[(3S)-hexahydro-2-oxo-1-[2-oxo-2-(1-pyrrolidinyl)ethyl]-1H-azepin-3-yl]amino]-3-[(2-methyl-5-benzofuranyl)amino]-1-oxo-2-propenyl]benzoic acid methyl ester | HPLC (method B) t_R 4.0 min; MS (ESI, pos. ion spectrum) m/z 598 |

-continued

| Ex. | Structure | Name | Characterization |
|---|---|---|---|
| 13 | 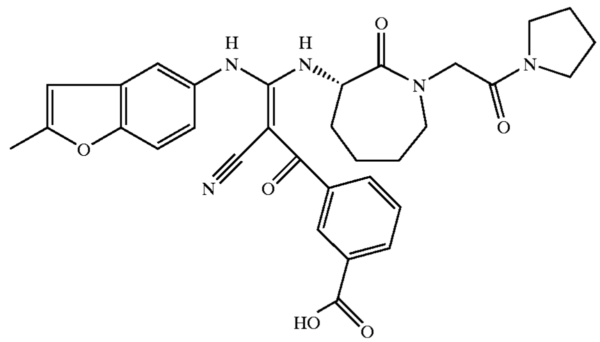 | 3-[2-Cyano-3-[[(3S)-hexahydro-2-oxo-1-[2-oxo-2-(1-pyrrolidinyl)ethyl]-1H-azepin-3-yl]amino]-3-[(2-methyl-5-benzofuranyl)amino]-1-oxo-2-propenyl]benzoic acid | HPLC (method B) t_R min, MS (ESI, pos. ion spectrum) m/z 584 |
| 14 | 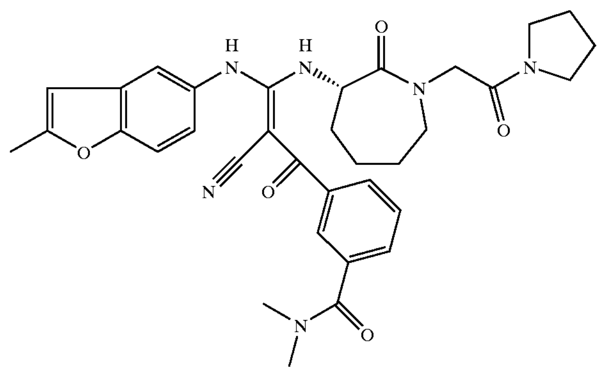 | 3-[2-Cyano-3-[[(3S)-hexahydro-2-oxo-1-[2-oxo-2-(1-pyrrolidinyl)ethyl]-1H-azepin-3-yl]amino]-3-[(2-methyl-5-benzofuranyl)amino]-1-oxo-2-propenyl]-N,N-dimethylbenzamide | HPLC (method B) t_R 3.7 min; MS (ESI, pos. ion spectrum) m/z 611 |
| 15 | 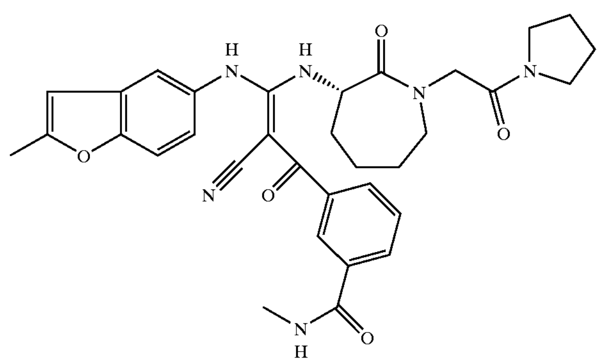 | 3-[2-Cyano-3-[[(3S)-hexahydro-2-oxo-1-[2-oxo-2-(1-pyrrolidinyl)ethyl]-1H-azepin-3-yl]amino]-3-[(2-methyl-5-benzofuranyl)amino]-1-oxo-2-propenyl]-N-methylbenzamide | HPLC (method B) t_R 3.6 min; MS (ESI, pos. ion spectrum) m/z 597 |
| 16 | 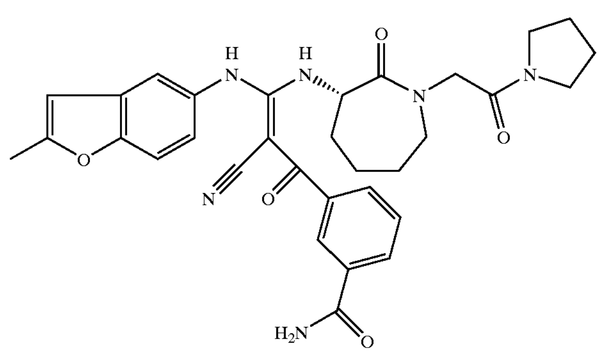 | 3-[2-Cyano-3-[[(3S)-hexahydro-2-oxo-1-[2-oxo-2-(1-pyrrolidinyl)ethyl]-1H-azepin-3-yl]amino]-3-[(2-methyl-5-benzofuranyl)amino]-1-oxo-2-propenyl]benzamide | HPLC (method B) t_R 3.5 min; MS (ESI, pos. ion spectrum) m/z 583 |

| Ex. | Structure | Name | Characterization |
|---|---|---|---|
| 17 | 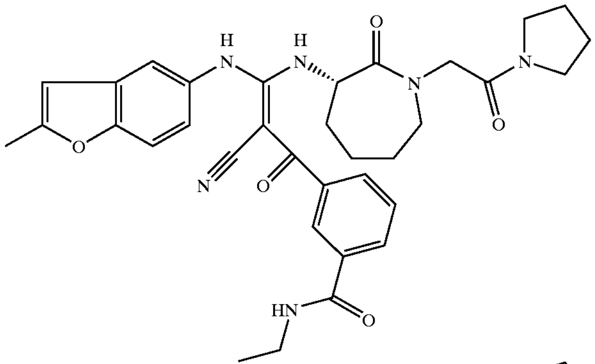 | 3-[2-Cyano-3-[[(3S)-hexahydro-2-oxo-1-[2-oxo-2-(1-pyrrolidinyl)ethyl]-1H-azepin-3-yl]amino]-3-[(2-methyl-5-benzofuranyl)amino]-1-oxo-2-propenyl]-N-ethylbenzamide | HPLC (method B) $t_R$ 3.7 min; MS (ESI, pos. ion spectrum) m/z 611 |
| 18 | 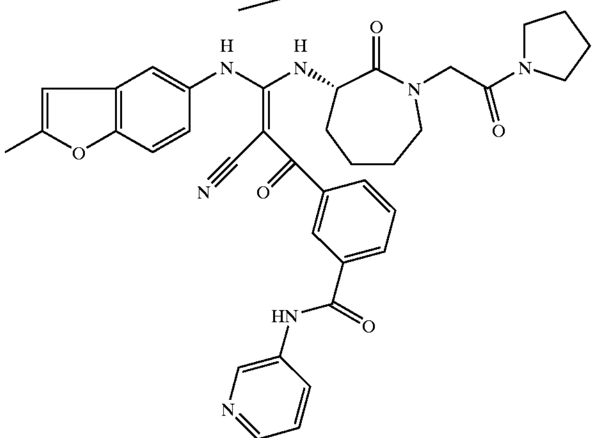 | 3-[2-Cyano-3-[[(3S)-hexahydro-2-oxo-1-[2-oxo-2-(1-pyrrolidinyl)ethyl]-1H-azepin-3-yl]amino]-3-[(2-methyl-5-benzofuranyl)amino]-1-oxo-2-propenyl]-N-(3-pyridinyl)benzamide | HPLC (method B) $t_R$ 3.4 min; MS (ESI, pos. ion spectrum) m/z 660 |
| 19 | 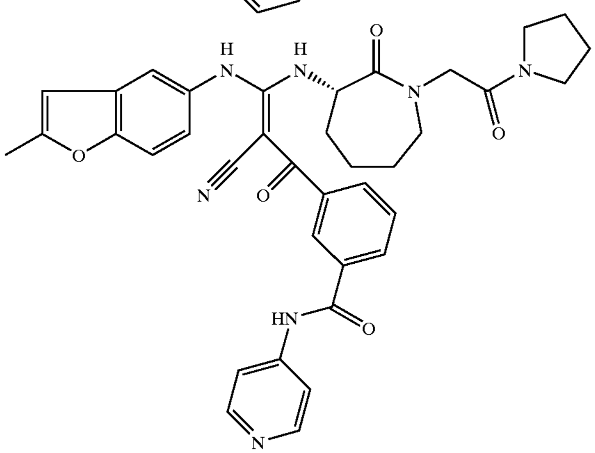 | 3-[2-Cyano-3-[[(3S)-hexahydro-2-oxo-1-[2-oxo-2-(1-pyrrolidinyl)ethyl]-1H-azepin-3-yl]amino]-3-[(2-methyl-5-benzofuranyl)amino]-1-oxo-2-propenyl]-N-(4-pyridinyl)benzamide | HPLC (method B) $t_R$ 3.4 min; MS (ESI, pos. ion spectrum) m/z 660 |

EXAMPLE 20

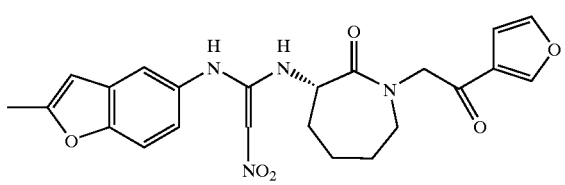

(3S)-Hexahydro-3-[[1-[(2-methyl-5-benzofuranyl)amino]-2-nitroethenyl]amino]-1-[2-oxo-2-(3-furanyl)ethyl]-2H-azepin-2-one A. Preparation of 1,1-dimethylethyl [(3S)-1-[2-(3-furanyl)-2-oxoethyl]hexahydro-2-oxo-1H-azepin-3-yl]carbamate. To a 50 mL flask charged with 1,1-dimethylethyl [(3S)-hexahydro-2-oxo-1H-azepin-3-yl]carbamate (0.57 g, 2.5 mmol) and 10 mL of DMF was added sodium hydride (0.15 g, 5.0 mmol). The reaction mixture was stirred under nitrogen at room temperature for 30 min. A solution of 2-bromo-1-(3-furanyl)ethanone in 2 mL of DMF was added to the reaction mixture slowly. The reaction mixture was stirred at room temperature for an additional hour and was then was concentrated in vacuo. The residue was purified by flash chromatography (silica, 1:1 hexane:ethyl acetate) to provide 1,1-dimethylethyl [(3S)-1-[2-(3-furanyl)-2-oxoethyl] hexahydro-2-oxo-1H-azepin-3-yl]carbamate (0.19 g, 22% yield).

B. Preparation of (3S)-3-amino-1-[(2-(3-furanyl)-2-oxoethyl]hexahydro-2H-azepin-2-one. To a solution of 1,1-dimethylethyl [(3S)-1-[2-(3-furanyl)-2-oxoethyl] hexahydro-2-oxo-1H-azepin-3-yl]carbamate (0.23 g, 1.0 mmol) in methylene chloride (1 mL) was added TFA (1.0 mL, 7.0 mmol). The reaction mixture was stirred at room temperature for 16 h, and was then concentrated in vacuo. The residue was purified by chromatography (AG-50W×2 ion exchange resin (hydrogen form), methanol then 2 N ammonia in methanol) to give (3S)-3-amino-1-[(2-(3-furanyl)-2-oxoethyl]hexahydro-2H-azepin-2-one (0.11 g, 67% yield).

C. Preparation of N-[1-(methylthio)-2-nitroethenyl]-2-methyl-5-benzofuranamine. To a solution of 2-methyl-5-benzofuranamine (1.6 g 11 mmol) dissolved in 50 mL of ethanol was added 1,1 bis(methylthio)-2-nitroethylene (11 mmol). The reaction mixture was refluxed for 4 h and concentrated in vacuo. The residue was triturated with 50 mL of ethyl acetate to provide N-[1-(methylthio)-2-nitroethenyl]-2-methyl-5-benzofuranamine (1.54 g, 54% yield) as a yellow solid.

D. Preparation of title compound. (3S)-3-Amino-1-[(2-(3-furanyl)-2-oxoethyl]hexahydro-2H-azepin-2-one (47.6 mg, 0.20 mmol) and N-[1-(methylthio)-2-nitroethenyl]-2-methyl-5-benzofuranamine (53.2 mg, 0.20 mmol) were dissolved in 1 mL of DMF. The resultant mixture was stirred at 60° C. for 20 h and was then was concentrated in vacuo. The residue was purified by gradient reverse phase HPLC (YMC C-18 column, linear gradient elution) to provide the title compound (8 mg, 9%): MS (ESI, pos. ion spectrum) m/z 453; HPLC (method A) $t_R$ 3.4 min.

EXAMPLE 21

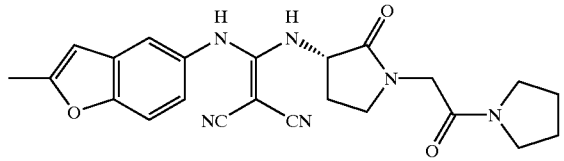

1-[[(3S)-3-[[2,2-Dicyano-1-[(2-methyl-5-benzofuranyl) amino]ethenyl]amino]-2-oxo-1-pyrrolidinyl]acetyl] pyrrolidine A. Preparation of 1,1-dimethylethyl (3S)-[1-[2-oxo-2-(1-pyrrolidinyl)ethyl]-2-oxo-3-pyrrolidinyl]carbamate. Lithium bis(trimethylsilyl)amide (1 N in THF, 10.4 mL, 10.4 mmol) in THF (5 mL) was added dropwise over 20 min to a solution of 1,1-dimethylethyl [(3S)-2-oxo-3-pyrrolidinyl] carbamate (1.0 g, 5.1 mmol) in THF (88 mL) stirring at ambient temperature under argon. After stirring at ambient temperature for 15 min the reaction was cooled to 0° C. A solution of 1-(bromoacetyl)pyrrolidine (1.1 g, 5.7 mmol) in THF (15 mL) was then added over 30 min. After stirring at 0° C. for 3 h, the reaction was quenched with 10% KHSO$_4$ and transferred to a separatory funnel with ethyl acetate. The mixture was washed with 10% KHSO$_4$ and brine and dried over magnesium sulfate. Concentration in vacuo afforded 2.3 g of crude product. Column chromatography (silica, acetonitrile) afforded pure product (0.61 g, 38%): $^1$H-NMR (CDCl$_3$) δ 5.21 (m, 1H), 4.27 (m, 1H), 4.04 (m, 2H), 3.60–3.41 (m, 6H), 2.62 (m, 1H), 2.04–1.83 (m, 5H), 1.48 (s, 9H); $^{13}$C-NMR (CDCl$_3$) δ 172.8, 165.2, 155.7, 79.6, 52.1, 45.8, 45.7, 45.2, 44.9, 28.2, 26.0, 23.9.

B. Preparation of (S)-1-[(3-amino-2-oxo-1-pyrrolidinyl) acetyl]pyrrolidine. To a solution of 1,1-dimethylethyl (3S)-[1-[2-oxo-2-(1-pyrrolidinyl)ethyl]-2-oxo-3-pyrrolidinyl] carbamate (0.61 g, 2.0 mmol) in dichloromethane (13 mL) was added TFA (2.2 g, 20 mmol). The reaction was stirred at ambient temperature for 4.5 h. Concentration in vacuo and sequential co-evaporation with dichloromethane and methanol afforded (S)-1-[(3-amino-2-oxo-1-pyrrolidinyl)acetyl] pyrrolidine as the TFA salt (0.83 g): $^1$H-NMR (CDCl$_3$) δ 4.23 (m, 1H), 4.03 (s, 2 H), 3.42 (m, 6H), 2.55 (m, 1H), 2.29 (m, 1H), 2.05–1.80 (m, 4H).

C. Preparation of title compound. A mixture of 2-methyl-5-benzofuranamine (0.24 mmol) and 1,1-bis(thiomethyl)-2,2-dicyanoethylene (34 mg, 0.20 mmol) in ethanol (0.33 mL) was stirred at 80° C. for 4.5 h. To the mixture was added (S)-1-[(3-amino-2-oxo-1-pyrrolidinyl)acetyl]pyrrolidine (TFA salt, 100 mg, 0.245 mmol) and triethylamine (0.035 mL, 0.25 mmol) and the resultant mixture was stirred at 80° C. for 17 h. The reaction mixture was purified by preparative HPLC (YMC ODS-A 30×250 mm, linear gradient—40% to 95% B over 30 min) followed by column chromatography (silica, 3% methanol/dichloromethane)to afford the title compound (3 mg, 4% yield): MS (ESI, pos. ion spectrum) m/z 433; HPLC (method A): $t_R$ 3.25 min.

EXAMPLE 22

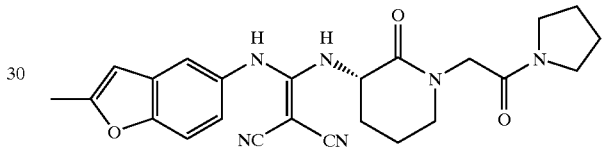

1-[[(3S)-3-[[2,2-Dicyano-1-[(2-methyl-5-benzofuranyl) amino]ethenyl]amino]hexahydro-2-oxo-1-piperidinyl] acetyl]pyrrolidine A. Preparation of 1,1-dimethylethyl [(3S)-1-[2-oxo-2-(1-pyrrolidinyl)ethyl]-2-oxo-3-piperidinyl]carbamate. Lithium bis(trimethylsilyl)amide (1 N in THF, 18.9 mL, 18.9 mmol) in THF (9 mL) was added dropwise over 35 min to a solution of 1,1-dimethylethyl ((3S)-2-oxo-3-piperidinyl)carbamate (2.0 g, 9.3 mmol) in THF (160 mL) stirring at ambient temperature under argon. After stirring at ambient temperature for 15 min the reaction was cooled to 0° C. and a solution of 1-(bromoacetyl)pyrrolidine (2.0 g, 10.4 mmol) in THF (27 mL) was then added over 60 min. After stirring at 0° C. for 2 h, the reaction was quenched with 10% KHSO$_4$ and transferred to a separatory funnel with ethyl acetate. The mixture was washed with 10% KHSO$_4$ and brine, dried over magnesium sulfate and concentrated in vacuo to afford 4.0 g of crude product. Column chromatography (silica, acetonitrile) afforded 1,1-dimethylethyl [(3S)-1-[2-oxo-2-(1-pyrrolidinyl)ethyl]-2-oxo-3-piperidinyl]carbamate (2.0 g, 66%): $^1$H-NMR (CDCl$_3$) δ 5.36 (m, 1H), 4.14 (d, J=14.1 Hz, 1H), 4.00 (m, 1H), 3.71 (d, J=14.1 Hz, 1H), 3.41–3.24 (m, 6H), 2.31 (m, 1H), 1.91–1.70 (m, 6H), 1.61 (m, 1H), 1.42 (s, 9H); $^{13}$C-NMR (CDCl$_3$) δ 170.0, 165.6, 155.6, 79.0, 51.5, 49.3, 48.6, 45.6, 45.5, 28.1, 27.6, 25.9, 23.8, 20.6.

B. Preparation of 1-[[(3S)-3-amino-2-oxo-1-piperidinyl] acetyl]pyrrolidine. To a solution of 1,1-dimethylethyl [(3S)-1-[2-oxo-2-(1-pyrrolidinyl)ethyl]-2-oxo-3-piperidinyl] carbamate (2.0 g, 6.2 mmol) in dichloromethane (40 mL) was added TFA (7.0 g, 62 mmol). The reaction was stirred at ambient temperature for 22 h. Evaporation in vacuo and sequential co-evaporation with dichloromethane and methanol afforded 1-[[(3S)-3-amino-2-oxo-1-piperidinyl]acetyl]

pyrrolidine as the TFA salt (2.9 g). Column chromatography (BIORAD AG-50W×2 (hydrogen form packed in 50% water/methanol), methanol then 2 N ammonia in methanol) afforded 1-[[(3S)-3-amino-2-oxo-1-piperidinyl]acetyl] pyrrolidine (1.07 g).

C. Preparation of title compound. A solution of 2-methyl-5-benzofuranamine (0.24 mmol) and 1,1-bis(methylthio)-2,2-dicyanoethylene (34 mg, 0.20 mmol) in ethanol (0.35 mL) was stirred at 80° C. for 5 h. To the mixture was added 1-[[(3S)-3-amino-2-oxo-1-piperidinyl]acetyl]pyrrolidine (55 mg, 0.24 mmol) and the resulting reaction was stirred at 80° C. overnight. The mixture was purified by column chromatography (silica, 3% methanol/dichloromethane)to afford the title compound (21 mg, 24% yield): MS (ESI, pos. ion spectrum) m/z 447; HPLC (method A) $t_R$ 3.4 min.

EXAMPLE 23

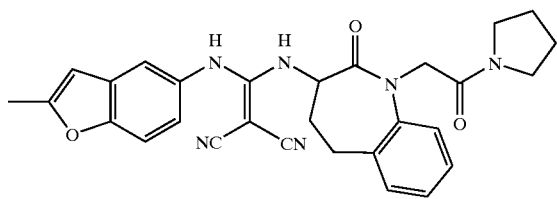

1-[[3-[[2,2-Dicyano-1-[(2-methyl-5-benzofuranyl)amino] ethenyl]amino]-2,3,4,5-tetrahydro-2-oxo-1H-1-benzazepin-1-yl]acetyl]pyrrolidine A. Preparation of 3-iodo-1,3,4,5-tetrahydro-2H-1-benzazepin-2-one. Trimethylsilyl iodide (0.56 mL, 0.4 mmol) was added to a solution of 1,3,4,5-tetrahydro-2H-1-benzazepin-2-one (0.32 g, 2.0 mmol) and TMEDA (0.91 mL, 6.0 mmol) in dichloromethane (10 mL) stirring at −15° C. After stirring at −15° C. for 15 min, iodine (0.76 g, 3.0 mmol) was added. The reaction was allowed to warm to 0° C. and was stirred for 2 h. The reaction mixture was transferred to a separatory funnel and washed with 1/1 10% $Na_2SO_3$/brine, dried with sodium sulfate, and evaporated to afford 0.94 g of crude product. Chromatography (silica, 25% ethyl acetate/hexane) gave 3-iodo-1,3,4,5-tetrahydro-2H-1-benzazepin-2-one (0.55 g, 96% yield): $^1$H-NMR (CDCl$_3$) δ 7.32–7.16 (m, 3H), 6.99 (m, 1H), 4.68 (m, 1H), 2.99 (m, 1H), 2.82–2.65 (m, 3H).

B. Preparation of 3-azido-1,3,4,5-tetrahydro-2H-1-benzazepin-2-one. A mixture of 3-iodo-1,3,4,5-tetrahydro-2H-1-benzazepin-2-one (0.55 g, 1.9 mmol) and sodium azide (0.16 g, 2.5 mmol) in DMF (0.5 mL) was stirred at 75° C. After 1 day, the reaction was transferred to a separatory funnel with water and ether. The mixture was extracted with ether, and the combined organic layers were washed with brine, dried over magnesium sulfate and concentrated in vacuo to provide 3-azido-1,3,4,5-tetrahydro-2H-1-benzazepin-2-one (0.32 g, 83% yield) which was used in the next step without further purification: $^1$H-NMR (CDCl$_3$) δ 7.80 (broad s, 1 H), 7.28 (m, 1H), 7.16 (m, 2H), 6.99 (m, 1H), 3.86 (m, 1H), 2.96 (m, 1H), 2.71 (m, 1H), 2.50 (m, 1H), 2.30 (m, 1H).

C. Preparation of 3-amino-1,3,4,5-tetrahydro-2H-1-benzazepin-2-one. To a solution of tin(II) chloride (0.42 g, 2.2 mmol) in methanol (3 mL) stirring at 0° C. was added, slowly, 3-azido-1,3,4,5-tetrahydro-2H-1-benzazepin-2-one (0.30 g, 1.5 mmol). After stirring at ambient temperature for 1 h, the reaction mixture was purified by column chromatography (BIORAD AG-50W×2 (hydrogen form packed in 50% water/methanol), methanol then 2N ammonia in methanol) to afford 3-amino-1,3,4,5-tetrahydro-2H-1-benzazepin-2-one (0.23 g): $^1$H-NMR (CDCl$_3$) δ 7.31 (m, 2H), 7.21 (m, 1H), 7.06 (m, 1H), 4.60 (broad s, 2H), 3.76 (m, 1H), 2.96 (m, 1H), 2.78 (m, 1H), 2.59 (m, 1H), 2.20 (m, 1H).

D. Preparation of 1,1-dimethylethyl (2,3,4,5-tetrahydro-2-oxo-1H-1-benzazepin-3-yl)carbamate. A solution of bis(1,1-dimethylethyl) dicarbonate (0.37 g, 1.7 mmol) in dichloromethane (2 mL) was slowly added to a solution of 3-amino-1,3,4,5-tetrahydro-2H-1-benzazepin-2-one (0.25 g, 1.4 mmol) and N,N-diisopropylethylamine (0.24 g, 0.33 mmol) in dichloromethane (5.5 mL) stirring under argon at 0° C. After stirring at ambient temperature for 1 day, the reaction was transferred to a separatory funnel with dichloromethane. The mixture was washed with 1N NaOH, 5% KHSO$_4$, and water, dried over magnesium sulfate and concentrated in vacuo to afford 0.87 g of crude product. Column chromatography (silica, 2% methanol/dichloromethane) afforded pure product (0.27 g, 69%): $^1$H-NMR (CDCl$_3$) δ 7.52 (broad s, 1H), 7.21–7.15 (m, 3H), 6.97 (m, 1H), 5.43 (m, 1H), 4.27 (m, 1H), 2.93 (m, 1H), 2.64 (m, 2H), 1.96 (m, 1H), 1.38 (s, 9H).

E. Preparation of 1,1-dimethylethyl [2,3,4,5-tetrahydro-2-oxo-1-[2-oxo-2-(1-pyrrolidinyl)ethyl]-1H-1-benzazepin-3-yl]carbamate. Lithium bis(trimethylsilyl)amide (1 N in THF, 2.0 mL, 2.0 mmol) in THF (1 mL) was added dropwise over 5 min to a solution of 1,1-dimethylethyl (2,3,4,5-tetrahydro-2-oxo-1H-1-benzazepin-3-yl)carbamate (0.27 g, 1.0 mmol) in THF (17 mL) stirring at ambient temperature under argon. After stirring at ambient temperature for 15 min the reaction was cooled to 0° C. and a solution of 1-(bromoacetyl) pyrrolidine (0.21 g, 1.1 mmol) in THF (2.8 mL) was then added over 10 min. After stirring at 0° C. for 2 h, the reaction was quenched with 5% KHSO$_4$ and transferred to a separatory funnel with ethyl acetate. The mixture was washed with 5% KHSO$_4$ and brine and dried over magnesium sulfate. Concentration in vacuo afforded 0.70 g of crude product. Chromatography (silica, 4% methanol/dichloromethane) afforded 1,1-dimethylethyl [2,3,4,5-tetrahydro-2-oxo-1-[2-oxo-2-(1-pyrrolidinyl)ethyl]-1H-1-benzazepin-3-yl]carbamate (0.35 g, 92%): $^1$H-NMR (CDCl$_3$) δ 7.20–7.12 (m, 4H), 5.43 (m, 1H), 4.67 (d, J=16.1 Hz, 1H), 4.33 (d, J=16.1 Hz, 1H), 4.25 (m, 1H), 3.55–3.38 (m, 4H), 2.55 (m, 2H), 2.06–1.80 (m, 5H), 1.65 (m, 1H), 1.35 (s, 9H).

F. Preparation of 1-[(3-amino-2,3,4,5-tetrahydro-2-oxo-1H-1-benzazepin-1-yl)acetyl]pyrrolidine. To a solution of 1,1-dimethylethyl [2,3,4,5-tetrahydro-2-oxo-1-[2-oxo-2-(1-pyrrolidinyl)ethyl]-1H-1-benzazepin-3-yl]carbamate (0.35 g, 0.90 mmol) in dichloromethane (6 mL) was added TFA (1.0 g, 9.0 mmol). The reaction was stirred at ambient temperature for 18 h. Evaporation in vacuo and sequential co-evaporation with dichloromethane and methanol afforded 1-[(3-amino-2,3,4,5-tetrahydro-2-oxo-1H-1-benzazepin-1-yl)acetyl]pyrrolidine as the TFA salt (0.41 g). Column chromatography (BIORAD AG50W×2 (hydrogen form packed in 50% water/methanol), methanol then 2 N ammonia in methanol) afforded 1-[(3-amino-2,3,4,5-tetrahydro-2-oxo-1H-1-benzazepin-1-yl)acetyl]pyrrolidine (0.26 g): $^1$H-NMR (CDCl$_3$) δ 7.15–6.95 (m, 4H), 4.47 (d, J=16.4 Hz, 1H), 4.25 (d, J=16.4 Hz, 1H), 3.42–3.27 (m, 4H), 3.15 (m, 1H), 2.44 (m, 1H), 2.25 (m, 1H), 2.08 (m, 2H), 1.91–1.70 (m, 4H).

G. Preparation of title compound. A solution of 2-methyl-5-benzofuranamine (0.24 mmol), 1,1-bis(methylthio-2,2-dicyanoethylene (34 mg, 0.20 mmol) and triethylamine (0.035 mL, 0.25 mmol) in ethanol (0.35 mL) was stirred at 80° C. for 4 h. To the mixture was added 1-[(3-amino-2,3,4,5-tetrahydro-2-oxo-1H-1-benzazepin-1-yl)acetyl]

pyrrolidine (70 mg, 0.24 mmol) and the resulting reaction was stirred at 80° C. overnight. The reaction mixture was purified by column chromatography (silica, 5% methanol/ethyl acetate) to afford the title compound (3 mg, 3% yield): MS (ESI, pos. ion spectrum) m/z 509; HPLC (method A) $t_R$ 3.80 min.

EXAMPLE 24

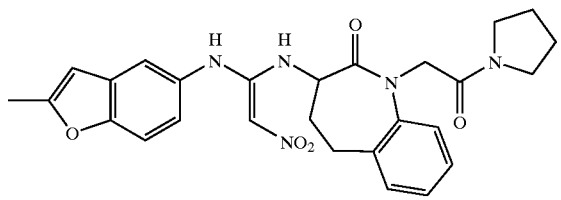

1-[[2,3,4,5-Tetrahydro-3-[[1-[(2-methyl-5-benzofuranyl)amino]-2-nitroethenyl]amino]-2-oxo-1H-1-benzazepin-1-yl]acetyl]pyrrolidine A solution of 2-methyl-5-benzofuranamine (0.24 mmol), 1,1-bis(methylthio)-2-nitroethylene (40 mg, 0.24 mmol) and triethylamine (0.035 mL, 0.25 mmol) in ethanol (0.35 mL) was stirred at 80° C. for 2 h. To the mixture was added 1-[(3-amino-2,3,4,5-tetrahydro-2-oxo-1H-1-benzazepin-1-yl)acetyl]pyrrolidine (70 mg, 0.24 mmol) and the resulting reaction was stirred at 80° C. overnight. The reaction mixture was purified by column chromatography (silica, 3% methanol/ethyl acetate) to provide the title compound (29 mg, 24% yield): MS (ESI, pos. ion spectrum) m/z 504; HPLC (method A) $t_R$ 3.67 min.

EXAMPLE 25

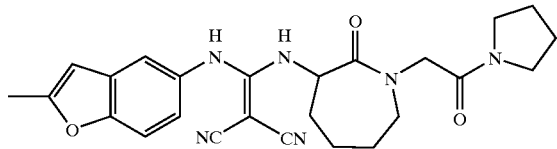

1-[[3-[[2,2-Dicyano-1-[(2-methyl-5-benzofuranyl)amino]ethenyl]amino]octahydro-2-oxo-1H-azocin-1-yl]acetyl]pyrrolidine A. Preparation of hexahydro-3-iodo-2(1H)-azocinone. Trimethylsilyl iodide (2.8 mL, 20 mmol) was added to a solution of hexahydro-2(1H)-azocinone (1.3 g, 10 mmol) and TMEDA (4.5 mL, 30 mmol) in dichloromethane (50 mL) stirring at −15° C. After stirring at −15° C. for 15 min, iodine (3.8 g, 15 mmol) was added. The reaction was allowed to warm to 0° C. and stirred for 2 h. The reaction mixture was transferred to a separatory funnel and washed with 1/1 10% $Na_2SO_3$/brine, dried with sodium sulfate, and evaporated in vacuo to afford 3.9 g of crude product. Chromatography (silica, 10% ethyl acetate/dichloromethane) gave hexahydro-3-iodo-2(1H)-azocinone (1.4 g, 56% yield): $^1$H-NMR (CDCl$_3$) δ 6.03 (broad s, 1H), 4.88 (m, 1H), 3.31 (m, 2H), 2.41–2.12 (m, 2H) , 1.74–1.38 (m, 6H).

B. Preparation of 3-azidohexahydro-2(1H)-azocinone. A solution of hexahydro-3-iodo-2(1H)-azocinone (1.4 g, 5.6 mmol) and sodium azide (0.47 g, 7.2 mmol) in DMF (1.4 mL) was stirred at 75° C. After 1 day, the reaction was transferred to a separatory funnel with water and ether. The mixture was extracted with ether, washed with brine and dried over magnesium sulfate to afford 3-azidohexahydro-2(1H)-azocinone (1.1 g, 86% yield) which was used in the next step without further purification: $^1$H-NMR (CDCl$_3$) δ 6.15 (broad s, 1H), 4.00 (m, 1H), 3.29 (m, 2H), 2.21–1.90 (m, 2H), 1.69–1.38 (m, 6H).

C. Preparation of 3-aminohexahydro-2(1H)-azocinone. To a solution of tin (II) chloride (1.8 g, 9.6 mmol) in methanol (10 mL) stirring at 0° C. was slowly added 3-azidohexahydro-2(1H)-azocinone (1.1 g, 6.4 mmol). After stirring at ambient temperature for 2 h, the reaction mixture was purified by column chromatography (BIOHAD AG-50W×2 (hydrogen form packed in 50% water/methanol), methanol then 2N ammonia in methanol) to afford 3-aminohexahydro-2 (1H)-azocinone (1.0 g): $^1$H-NMR (DMSO-d$_6$) δ 7.61 (broad s, 1H), 3.61 (m, 4H), 3.05 (m, 1H), 1.90–1.75 (m, 2H), 1.47–1.38 (m, 6H).

D. Preparation of 1,1-dimethylethyl (octahydro-2-oxo-3-azocinyl)carbamate. bis(1,1-dimethylethyl) dicarbonate (1.7 g, 7.6 mmol) in dichloromethane (9 mL) was slowly added to a solution of 3-aminohexahydro-2(1H)-azocinone (1.1 g, 6.4 mmol) and N,N-diisopropylethylamine (1.1 g, 8.1 mmol) in dichloromethane (25 mL) stirring under argon at 0° C. After stirring at ambient temperature for 1 day, the reaction was transferred to a separatory funnel with dichloromethane. The mixture was washed with 1N NaOH, 5% $KHSO_4$, and water; dried over magnesium sulfate and concentrated to afford 2.5 g of crude product. Column chromatography (silica, 4% methanol/dichloromethane) afforded 1,1-dimethylethyl (octahydro-2-oxo-3-azocinyl) carbamate (0.70 g, 45%): $^1$H-NMR(CDCl$_3$) δ 5.70 (broad s, 1H), 5.52 (m, 1H), 4.58 (m, 1H), 3.55 (m, 1H), 3.20 (m, 1H), 2.07 (m, 1H), 1,62 (m, 7H), 1.44 (s, 9H).

E. Preparation of 1,1-dimethylethyl [octahydro-1-[2-oxo-2-(1-pyrrolidinyl)ethyl]-2-oxo-3-azocinyl]carbamate. Lithium bis(trimethylsilyl)amide (1 N in THF, 5.8 mL, 5.8 mmol) in THF (2.8 mL) was added dropwise over 10 min to a solution of 1,1-dimethylethyl (octahydro-2-oxo-3-azocinyl) carbamate (0.70 g, 2.9 mmol) in THF (50 mL) stirring at ambient temperature under argon. After stirring at ambient temperature for 15 min the reaction was cooled to 0° C. and a solution of 1-(bromoacetyl)pyrrolidine (0.62 g, 3.2 mmol) in THF (8.3 mL) was then added over 10 min. After stirring at 0° C. for 2 h, the reaction was quenched with 5% $KHSO_4$ and transferred to a separatory funnel with ethyl acetate. The mixture was washed with 5% $KHSO_4$ and brine; dried over magnesium sulfate and concentrated in vacuo to afford 1.5 g of crude product. Column chromatography (silica, 2% methanol/dichloromethane) afforded 1,1-dimethylethyl [octahydro-1-[2-oxo-2-(1-pyrrolidinyl)ethyl]-2-oxo-3-azocinyl]carbamate (0.98 g, 96%).

F. Preparation of 1-[(3-aminohexahydro-2-oxo-1(2H)-azocinyl)acetyl]pyrrolidine. To a solution of 1,1-dimethylethyl [octahydro-1-[2-oxo-2-(1-pyrrolidinyl) ethyl]-2-oxo-3-azocinyl]carbamate (0.98 g, 2.8 mmol) in dichloromethane (18 mL) was added TFA (3.1 g, 28 mmol). After stirring at ambient temperature for 21 h the reaction was evaporated in vacuo and sequentially co-evaporated with dichloromethane and methanol to afford 1-[(3-aminohexahydro-2-oxo-1(2H)-azocinyl)acetyl]pyrrolidine as the TFA salt (1.6 g). Column chromatography (BIORAD AG-50W×2 (hydrogen form packed in 50% water/methanol), methanol then 2 N ammonia in methanol) afforded 1-[(3-aminohexahydro-2-oxo-1(2H)-azocinyl) acetly]pyrrolidine (0.62 g, 88%): $^1$H-NMR (CDCl$_3$) δ 4.29 (d, J=16.1 Hz, 1H), 3.72 (m, 2H), 3.40 (d, J=16.1 Hz, 1H), 3.26–3.10 (m, 5H), 2.17 (broad s, 1H), 3.15 (m, 1H), 1.80–1.55 (m, 4H), 1.33 (m, 8H).

G. Preparation of title compound. A solution of 2-methyl-5-benzofuranamine (0.24 mmol), 1,1-bis(methylthio)-2,2- dicyanoethylene (34 mg, 0.20 mmol) and triethylamine (0.035 mL, 0.25 mmol) in ethanol (0.35 mL) was stirred at 80° C. for 3 h. To the mixture was added 1-[(3-aminohexahydro-2-oxo-1(2H)-azocinyl)acetly]pyrrolidine (62 mg, 0.24 mmol) and the resulting reaction was stirred at 80° C. overnight. The reaction mixture was purified by column chromatography (silica, 2% methanol/dichloromethane) to afford the title compound (14 mg, 12% yield): MS (ESI, pos. ion spectrum) m/z 475; HPLC (method A) $t_R$ 3.69 min.

EXAMPLE 26

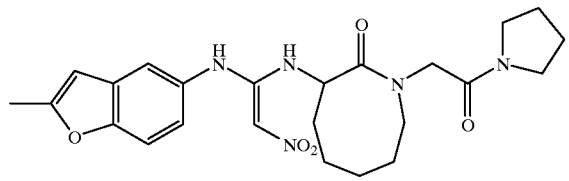

1-[[Octahydro-3-[[1-[(2-methyl-5-benzofuranvl)amino]-2-nitroethenyl]amino]-2-oxo-1H-azocin-1-yl]acetyl] pyrrolidine A solution of 2-methyl-5-benzofuranamine (0.24 mmol), 1,1-bis(methylthio)-2-nitroethylene (40 mg, 0.24 mmol) and triethylamine (0.035 mL, 0.25 mmol) was stirred at 80° C. for 2 h. To the mixture was added 1-[(3-aminohexahydro-2-oxo-1(2H)-azocinyl)acetyl]pyrrolidine (62 mg, 0.24 mmol) and the resulting reaction was stirred at 80° C. overnight. The reaction mixture was purified by column chromatography (silica, 2.5% methanol/dichloromethane) to afford the title compound (36 mg, 32% yield): MS (ESI, pos. ion spectrum) m/z 470; HPLC (method A): $t_R$ 3.47 min.

EXAMPLE 27

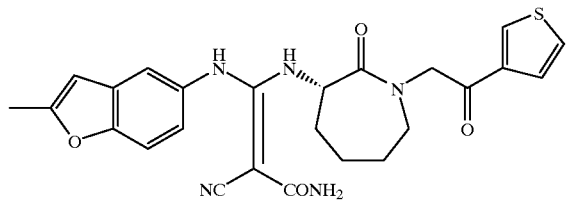

2-Cyano-3-[[(3S)-hexahydro-2-oxo-1-[2-oxo-2-(3-thienyl) ethyl]-1H-azepin-3-yl]amino]-3-[(2-methyl-5-benzofuranyl)amino]propenamide A. Preparation of 1,1-dimethylethyl [(3S)-1-[2-(3-thienyl)-2-oxoethyl]hexahydro-2-oxo-1H-azepin-3-yl]carbamate. Lithium bis(trimethylsilyl)amide (1 N in THF, 8.0 mL, 8.0 mmol) in THF (4 mL) was added dropwise over 10 min to a solution of 1,1-dimethylethyl [(3S)-hexahydro-2-oxo-1H-azepin-3-yl]carbamate (0.92 g, 4.0 mmol) in THF (68 mL) stirring at ambient temperature under argon. A solution of 2-bromo-1-(3-thienyl)ethanone (1.24 g, 6.0 mmol) in THF (12 mL) was then added over 3 min. After stirring at ambient temperature for 2.5 h, the reaction was quenched with 5% $KHSO_4$ and transferred to a separatory funnel with ethyl acetate. The mixture was washed with 5% $KHSO_4$ and brine; dried over magnesium sulfate and concentrated in vacuo to afford 2.1 g of crude product. Chromatography (silica, 25% ethyl acetate/hexane) afforded 1,1-dimethylethyl [(3S)-1-[2-(3-thienyl)-2-oxoethyl]hexahydro-2-oxo-1H-azepin-3-yl]carbamate (0.44 g, 31%): $^1$H-NMR (CDCl$_3$) δ 8.18 (m, 1H), 7.56 (m, 1H), 7.36 (m, 1H), 5.95 (m, 1H), 4.76 (s, 2H), 4.49 (m, 1H), 3.72 (m, 1H), 3.20 (m, 1H), 2.10–1.30 (m, 6H) , 1.44 (s, 9H).

B. Preparation of (3S)-3-amino-1-[(2-(3-thienyl)-2-oxoethyl]hexahydro-2H-azepin-2-one. To a solution of 1,1-dimethylethyl [(3S)-1-[2-(3-thienyl)-2-oxoethyl]hexahydro-2-oxo-1H-azepin-3-yl]carbamate (0.44 g, 1.2 mmol) in dichloromethane (8.2 mL) was added TFA (1.4 g, 12 mmol). The reaction was stirred at ambient temperature for 2 h and was then concentrated in vacuo and sequentially co-evaporated with dichloromethane and methanol to afford (3S)-3-amino-1-[(2-(3-thienyl)-2-oxoethyl]hexahydro-2H-azepin-2-one as the TFA salt (0.33 g). Chromatography (BIORAD AG-50W×2 (hydrogen form packed in 50% water/methanol), methanol then 2 N ammonia in methanol) and flash chromatography (silica, 10% methanol/dichloromethane) afforded (3S)-3-amino-1-[(2-(3-thienyl)-2-oxoethyl]hexahydro-2H-azepin-2-one. (0.24 g, 76%): $^1$H-NMR (CDCl$_3$) δ 8.38 (d, 1 H, J=1.2 Hz), 7.53 (m, 1H), 7.48 (m, 1H), 4.90 (broad s, 2H), 4.88 (s, 2H), 4.35 (d, 1 H, J=10.4 Hz), 3.70 (m, 1H), 3.29 (m, 1H), 2.15–1.60 (m, 6H).

C. Preparation of title compound. A solution of 2-methyl-5-benzofuranamine (32 mg, 0.22 mmol) and 3,3-bis (methylthio)-2-cyanoacrylamide (41 mg, 0.22 mmol) in ethanol (0.35 mL) was heated at 80° C. After stirring for 4 h, (3S)-3-amino-1-[(2-(3-thienyl)-2-oxoethyl]hexahydro-2H-azepin-2-one (74 mg, 0.29 mmol) in ethanol (0.74 mL) was added. After stirring at 80° C. for 2 days, the reaction was purified by column chromatography (silica, 2% methanol/dichloromethane) to afford the title compound (7 mg, 7% yield): MS (ESI, pos. ion spectrum) m/z 492; HPLC (method A) $t_R$ 3.89 min.

EXAMPLE 28

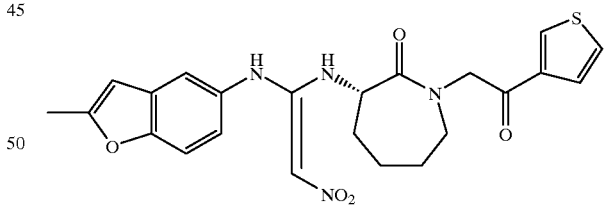

(3S)-Hexahydro-3-[[1-[(2-methyl-5-benzofuranyl)amino]-2-nitroethenyl]amino]-1-[2-oxo-2-(3-thienyl)ethyl]-2H-azein-2-one A mixture of N-[1-(methylthio)-2-nitroethenyl]-2-methyl-5-benzofuranamine (32 mg, 0.22 mmol) and (3S)-3-amino-1-[(2-(3-thienyl)-2-oxoethyl]hexahydro-2H-azepin-2-one (74 mg, 0.29 mmol) in ethanol (1 mL) was stirred at 80° C. for 1 day. The reaction was purified by column chromatography (silica, 3% methanol/dichloromethane) to afford the title compound (32 mg, 30% yield): MS (ESI, pos. ion spectrum) m/z 469; HPLC (method A) $t_R$ 3.75 min.

EXAMPLE 29

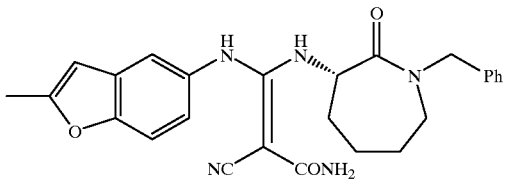

2-Cyano-3-[[(3S)-hexahydro-2-oxo-1-(phenylmethyl)-1H-azepin-3-yl]amino]-3-[(2-methyl-5-benzofuranyl)amino]-propenamide A. Preparation of 1,1-dimethylethyl [(3S)-hexahydro-1-phenylmethyl-2-oxo-1H-azepin-3-yl]carbamate. Lithium bis(trimethylsilyl)amide (1 N in THF, 6.0 mL, 6.0 mmol) in THF (3 mL) was added dropwise over 20 min to a solution of 1,1-dimethylethyl [(3S)-hexahydro-2-oxo-1H-azepin-3-yl]carbamate (0.69 g, 3.0 mmol) in THF (50 mL) stirring at ambient temperature under argon. Benzyl bromide (0.60 g, 0.42 mL, 3.5 mmol) in THF (9 mL) was then added over 5 min. After stirring at ambient temperature overnight, the reaction was quenched with 5% KHSO$_4$ and transferred to a separatory funnel with ethyl acetate. The mixture was washed with 5% KHSO$_4$ and brine; dried over magnesium sulfate and concentrated in vacuo to afford 1.1 g of crude product. Column chromatography (silica, 20% ethyl acetate/hexane) afforded 1,1-dimethylethyl [(3S)-hexahydro-1-phenylmethyl-2-oxo-1H-azepin-3-yl]carbamate (0.50 g, 52%): $^1$H-NMR (CDCl$_3$) δ 7.30–7.20 (m, 5H), 6.04 (m, 1H), 4.80 (d, 1H, J=14.6 Hz), 4.41 (m, 1H), 4.40 (d, 1 H, J=14.6 Hz), 3.41 (m, 1H), 3.19 (m, 1H), 2.10–1.20 (m, 6H), 1.44 (s, 9H).

B. Preparation of 3-aminohexahydro-1-phenylmethyl-2H-azepin-2-one. To a solution of 1,1-dimethylethyl [(3S)-hexahydro-1-phenylmethyl-2-oxo-1H-azepin-3-yl]carbamate (0.50 g, 1.6 mmol) in dichloromethane (10 mL) was added TFA (1.8 g, 16 mmol). The mixture was stirred at ambient temperature for 5 h. Evaporation in vacuo and sequential co-evaporation with dichloromethane and methanol afforded the product as the TFA salt (0.66 g). Column chromatography (BIORAD AG-50W×2 (hydrogen form packed in 50% water/methanol), methanol then 2 N ammonia in methanol) afforded 3-aminohexahydro-1-phenylmethyl-2H-azepin-2-one (0.29 g, 62%): $^1$H-NMR (CDCl$_3$) δ 7.30–7.20 (m, 5H), 4.78 (d, 1 H, J=14.5), 4.48 (d, 1 H, J=14.5 Hz), 3.68 (d, 1 H, J=10.7 Hz), 3.40 (m, 1H), 3.20 (m, 1H), 2.00–1.10 (m, 6H); $^{13}$C-NMR (CDCl$_3$) δ 176.9, 138.1, 128.6, 128.2, 127.4, 54.1, 51.7, 47.7, 34.1, 28.1, 27.3.

C. Preparation of title compound. A solution of 2-methyl-5-benzofuranamine (32 mg, 0.22 mmol) and 3,3-bis(methylthio)-2-cyanoacrylamide (41 mg, 0.22 mmol) in ethanol (0.35 mL) was stirred at 80° C. After stirring for 5 h, a solution of 3-aminohexahydro-1-phenylmethyl-2H-azepin-2-one (74 mg, 0.29 mmol) in ethanol (0.74 mL) was added. After stirring at 80° C. for 2 days, the reaction was purified by column chromatography (silica, 1% methanol/dichloromethane) to afford the title compound (37 mg, 37% yield): MS (ESI, pos. ion spectrum) m/z 458; HPLC (method A) t$_R$ 4.13 min.

EXAMPLE 30

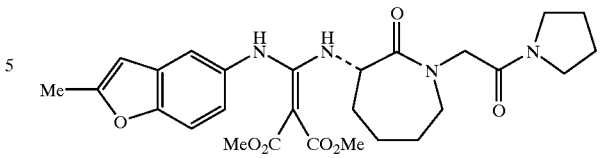

[[[(3S)-Hexahydro-2-oxo-1-[2-oxo-2-(1-pyrrolidinyl)ethyl]-1H-azepin-3-yl]amino][(2-methyl-5-benzofuranyl)amino]methylene]propanedioic Acid Dimethyl Ester Sodium hydride (95%, 11 mg, 0.44 mmol) was added to a solution of dimethyl malonate (40 mg, 0.30 mmol) in DMF (1.5 mL) at 0° C. The resulting mixture was warmed to room temperature, 2-methyl-5-isothiocyanatobenzofuran (56 mg, 0.30 mmol) was then added, and the resulting solution was stirred at at room temperature for 30 minutes. To the solution was then added 1-[[(3S)-3-aminohexahydro-2-oxo-1H-azepin-1-yl]acetyl]pyrrolidine (71 mg, 0.30 mmol) followed by mercury (II) chloride (82 mg, 0.30 mmol). The resulting dark mixture was stirred at room temperature for 2 h, then filtered through CELITE. The filtrate was concentrated, and the residue was purified by flash chromatography (silica, 1 to 5% methanol/dichloromethane) to afford the title compound as a pale yellow solid (63 mg, 40%): MS (ESI, pos. ion spectrum) m/z 527, HPLC (method A): t$_R$ 3.5 min.

EXAMPLE 31

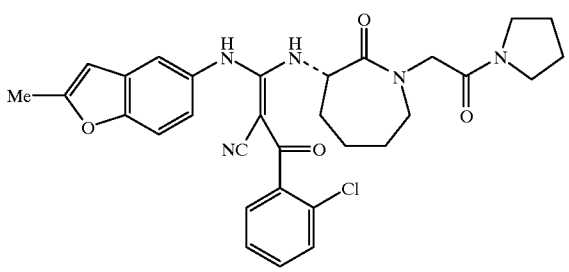

1-[[(3S)-3-[[3-(2-Chlorophenyl)-2-cyano-1-[(2-methyl-5-benzofuranyl)amino]-3-oxo-1-propenyl]amino]hexahydro-2-oxo-1H-azepin-1-yl]acetyl]pyrrolidine Triethylamine (0.04 mL, 0.29 mmol) was added to a suspension of 2-methyl-5-benzofuranamine·HCl (40 mg, 0.22 mmol) and acetonitrile (0.5 mL) at room temperature, which resulted in a clear solution. To the solution was added α-[bis(methylthio)methylene]-2-chloro-β-oxobenzenepropanenitrile(56 mg, 0.20 mmol) and the resulting solution was heated at 50° C. for 1 hour. To this mixture was added 1-[[(3S)-3-aminohexahydro-2-oxo-1H-azepin-1-yl]acetyl]pyrrolidine (47 mg, 0.20 mmol) and the resulting mixture was heated at 70° C. After 4 h, the mixture was concentrated in vacuo. The residue was purified by flash chromatography (silica, 0 to 2% methanol/dichloromethane) to give the title compound as a white solid (44 mg, 39%): MS (ESI, pos. ion spectrum) m/z 574/576 (M+H); HPLC (method A) t$_R$ 4.03 min.

EXAMPLE 32

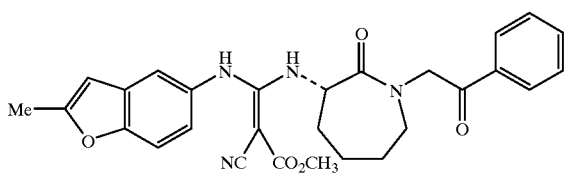

2-Cyano-3-[[(3S)-hexahydro-2-oxo-1-(2-oxo-1-phenylethyl)-1H-azepin-3-yl]amino]-3-[(2-methyl-5-benzofuranyl)amino]propenoic Acid Methyl Ester A solution of 2-methyl-5-benzofuranamine·HCl (35 mg, 0.24 mmol), ethyl 2-cyano-3,3-bis(methylthio)-2-propenoate (47 mg, 0.23 mmol), and ethanol (0.4 mL) was heated at 70° C. for 12 h. To the mixture was added 3-aminohexahydro-1-(2-oxo-2-phenylethyl)-2H-azepin-2-one (56 mg, 0.23 mmol). The resulting mixture was heated at 80° C. for 2 days, and then concentrated in vacuo. The residue was purified by preparative HPLC (column-YMC-PACK ODSA S5, 30×250 mm); flow rate 25 mL/min; gradient time 55 min) to give the title compound as a pale yellow solid (8 mg, 7%): MS (ESI, pos. ion spectrum) m/z 501; HPLC (method A) $t_R$ 4.26 min.

EXAMPLE 33

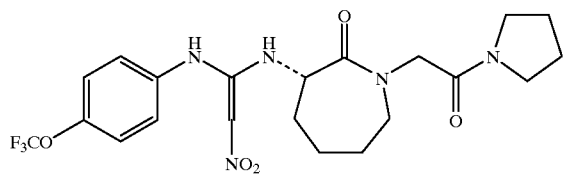

1-[[(3S)-Hexahydro-3-[[2-nitro-1-[[4-(trifluoromethoxy)phenyl]amino]ethenyl]amino]-2-oxo-1H-azepin-1-yl]acetyl]pyrrolidine A mixture of 4-(trifluoromethoxy)aniline (20 mg, 0.11 mmol) and 1,1-bis(methylthio)-2-nitroethylene (19 mg, 0.12 mmol) in ethanol (0.25 mL) was heated at 80° C. for 5 h. To the mixture was added 1-[[(3S)-3-aminohexahydro-2-oxo-1H-azepin-1-yl]acetyl]pyrrolidine (27 mg, 0.11 mmol). The resulting solution was stirred at 80° C. for 14 h, and the mixture was then concentrated in vacuo. The residue was purified by preparative HPLC (YMC-PACK ODSA S5 (30× 250 mm); flow rate 25 mL/min; gradient time 55 min) to furnish the title compound as a white solid (30 mg, 55%): MS (ESI, pos. ion spectrum) m/z 486; HPLC (method A) $t_R$ 3.59 min.

EXAMPLES 34–35

Using the methodology described for the title compound in Example 33, the following compounds were prepared.

| Ex. | Structure | Name | Character-ization |
|---|---|---|---|
| 34 | 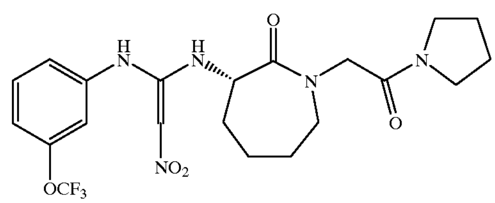 | 1-[[(3S)-Hexahydro-3-[[2-nitro-1-[[3-(trifluoromethoxy)phenyl]amino]ethenyl]amino]-2-oxo-1H-azepin-1-yl]acetyl]pyrrolidine | MS (ESI, pos. ion spectrum) m/z 486; HPLC (method A) $t_R$ 3.60 min |
| 35 | 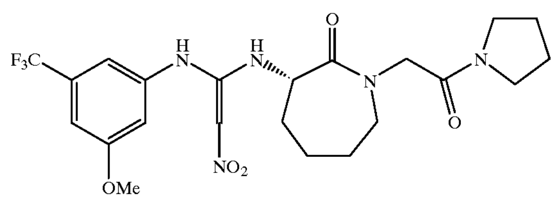 | 1-[[(3S)-Hexahydro-3-[[1-[[3-methoxy-5-(trifluoromethyl)phenyl]amino]-2-nitroethenyl]amino]-2-oxo-1H-azepin-1-yl]acetyl]pyrrolidine | MS (ESI, pos. ion spectrum) m/z 500; HPLC (method A) $t_R$ 3.72 min |

EXAMPLE 36

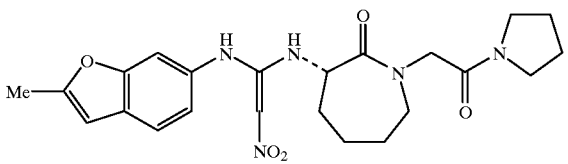

1-[[(3S)-Hexahydro-3-[[1-[(2-methyl-6-benzofuranyl)amino]-2-nitroethenyl]amino]-2-oxo-1H-azepin-1-yl]acetyl]pyrrolidine A. Preparation of 2-methyl-6-benzofuranamine. To a suspension of excess Raney nickel in ethanol (3 mL) was added 2-methyl-6-nitrobenzofuran (300 mg, 1.69 mmol). Hydrazine hydrate (153 mg, 3.06 mmol) was then added and the flask capped at room temperature. Gas evolution occured and the flask was periodically vented to avoid pressurization. After 60 minutes, the reaction mixture was filtered through CELITE. The filtrate was concentrated in vacuo to provide 200 mg (81%) of 2-methyl-6-benzofuranamine as a brown oil: MS (ESI, pos. ion spectrum) m/z 148 (M+H); HPLC (method C) $t_R$ 1.7 min.

B. Preparation of title compound. To 2-methyl-6-benzofuranamine (30 mg, 0.16 mmol) in ethyl acetate (1

ML) was added 1,1-bis(methylthio)-2-nitroethylene (26 mg, 0.16 mmol) and the mixture heated at reflux for 30 minutes. After cooling to room temperature, 1-[[(3S)-3-aminohexahydro-2-oxo-1H-azepin-1-yl]acetyl]pyrrolidine (38 mg, 0.16 mmol) was added and the resultant mixture heated for an additional 2 h. The reaction mixture was placed directly on a silica column and the product was eluted with 2% methanol/chloroform. Product-containing fractions were concentrated in vacuo and the residue was then further purified by elution through a reverse-phase cartridge (Varian C-18 Mega Bond Elut) with a gradient of 100% water to 100% methanol. Concentration of product-containing fractions in vacuo provided the title compound (9 mg, 12%): MS (ESI, pos. ion spectrum) m/z 456 (M+H); HPLC (method C) $t_R$ 3.5 min.

EXAMPLE 27

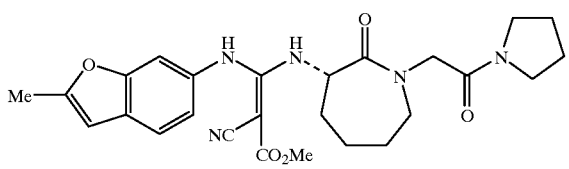

2-Cyano-3-[[(3S)-hexahydro-2-oxo-1-[2-oxo-2-(1-pyrrolidinyl)ethyl]-1H-azepin-3-yl]amino]-3-[(2-methyl-6-benzofuranyl)amino]propenoic Acid Methyl Ester In a procedure similar to that in example 36, the title compound (8 mg, 11%) was synthesized from 2-methyl-6-benzofuranamine (34 mg, 0.23 mmol), methyl 2-cyano-3,3-bis(methylthio)-2-propenoate (47 mg, 0.23 mmol), and 1-[[(3S)-3-aminohexahydro-2-oxo-1H-azepin-1-yl]acetyl]pyrrolidine (102 mg, 0.43 mmol) using acetonitrile as the reaction solvent: MS (ESI, pos, ion) m/z 494 (M+H); HPLC (method C) $t_R$ 3.6 min.

EXAMPLE 38

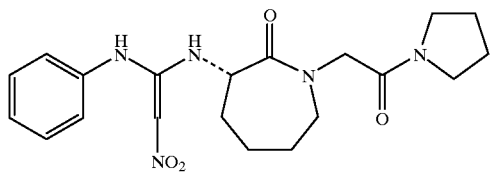

1-[[(3S)-Hexahydro-3-[[2-nitro-1-(phenylamino)ethenyl]amino]-2-oxo-1H-azepin-1-yl]acetyl]pyrrolidine A mixture of 1,1-bis(methylthio)-2-nitroethylene (165.2 mg, 1 mmol) and aniline (93.1 mg, 1 mmol) in ethanol (1 mL) was heated to 80° C. for 3 hr. The reaction was cooled to room temperature and the yellow solid (190 mg, 90% yield) was collected by filtration. A portion of this material (42 mg, 0.2 mmol) and 1-[[(3S)-3-aminohexahydro-2-oxo-1H-azepin-1-yl]acetyl]pyrrolidine (48 mg, 0.2 mmol) in ethanol (1 mL) were heated at 80° C. for 20 h. Preparative HPLC afforded the title compound as a pale yellow solid (43 mg, 53%): MS (ESI, pos. ion spectrum) m/z 402; HPLC (method A) $t_R$ 2.80 min.

EXAMPLES 39–63

Using the methodology described for Example 38, the following compounds were prepared.

| Ex. | Structure | Name | Characterization |
|---|---|---|---|
| 39 | 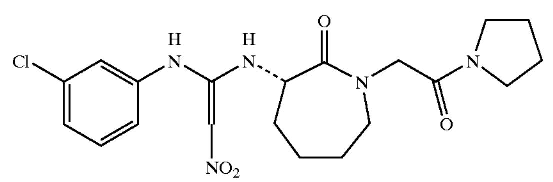 | 1-[[(3S)-3-[[1-[3-Chlorophenyl)amino]-2-nitroethenyl]amino]hexahydro-2-oxo-1H-azepin-1-yl]acetyl]pyrrolidine | HPLC (method A) $t_R$ 3.30 min; MS (ESI, pos. ion spectrum) m/z 436/438 |
| 40 | 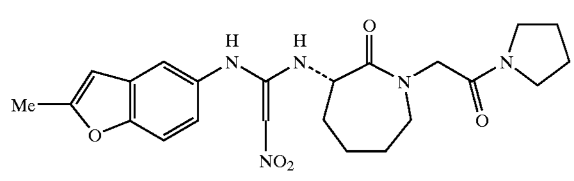 | 1-[[(3S)-Hexahydro-3-[[1-[(2-methyl-5-benzofuranyl)amino]-2-nitroethenyl]amino]-2-oxo-1H-azepin-1-yl]acetyl]pyrrolidine | HPLC (method A) $t_R$ 3.41 min; MS (ESI, pos. ion spectrum) m/z 456 |
| 41 | 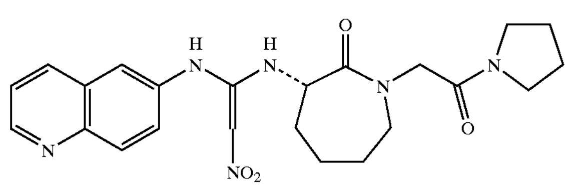 | [1-(3S)-Hexahydro-3-[[2-nitro-1-(6-quinolinylamino)ethenyl]amino]-2-oxo-1H-azepin-1-yl]acetyl]pyrrolidine | HPLC (method A) $t_R$ 2.05 min; MS (ESI, pos. ion spectrum) m/z 453 |

-continued

| Ex. | Structure | Name | Characterization |
|---|---|---|---|
| 42 | 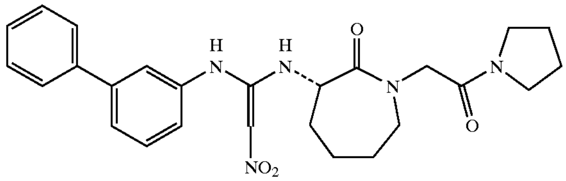 | 1-[[(3S)-3-[[1-([1,1'-Biphenyl]-3-ylamino)-2-nitroethenyl]amino]hexahydro-2-oxo-1H-azepin-1-yl]acetyl]pyrrolidine | HPLC (method A) $t_R$ 3.78 min; MS (ESI, pos. ion spectrum) m/z 478 |
| 43 | 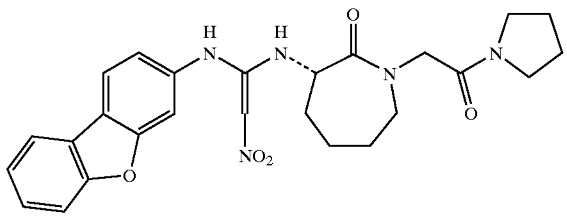 | 1-[[(3S)-3-[[1-(3-Dibenzofuranylamino)-2-nitroethenyl]amino]hexahydro-2-oxo-1H-azepin-1-yl]acetyl]pyrrolidine | HPLC (method A) $t_R$ 3.81 min; MS (ESI, pos. ion spectrum) m/z 492 |
| 44 | 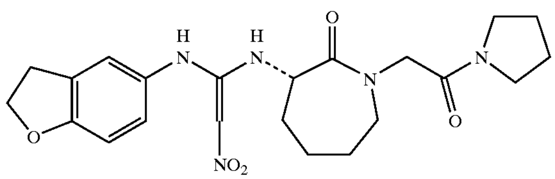 | 1-[[(3S)-3-[[1-[(2,3-Dihydro-5-benzofuranyl)amino]-2-nitroethenyl]amino]hexahydro-2-oxo-1H-azepin-1-yl]acetyl]pyrrolidine | HPLC (method A) $t_R$ 2.92 min; MS (ESI, pos. ion spectrum) m/z 444 |
| 45 | 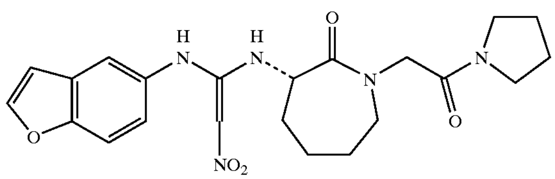 | 1-[[(3S)-3-[[1-(5-Benzofuranylamino)-2-nitroethenyl]amino]hexahydro-2-oxo-1H-azepin-1-yl]acetyl]pyrrolidine | HPLC (method A) $t_R$ 3.09 min; MS (ESI, pos. ion spectrum) m/z 442 |
| 46 | 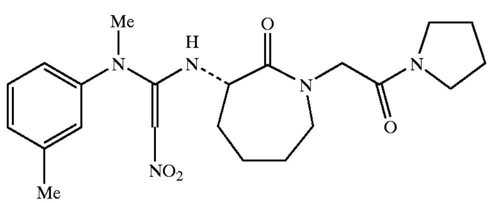 | 1-[[(3S)-Hexahydro-3-[[1-[methyl(3-methylphenyl)amino]-2-nitroethenyl]amino]-2-oxo-1H-azepin-1-yl]acetyl]pyrrolidine | HPLC (method A) $t_R$ 2.88 min; MS (ESI, pos. ion spectrum) m/z 430 |
| 47 | 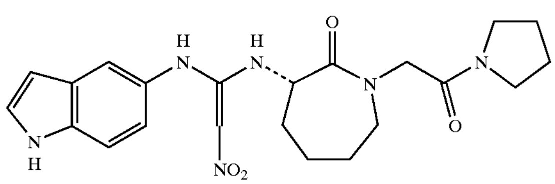 | 1-[[(3S)-Hexahydro-3-[[1-(1H-indol-5-ylamino)-2-nitroethenyl]amino]-2-oxo-1H-azepin-1-yl]acetyl]pyrrolidine | HPLC (method A) $t_R$ 2.80 min; MS (ESI, pos. ion spectrum) m/z 441 |
| 48 | 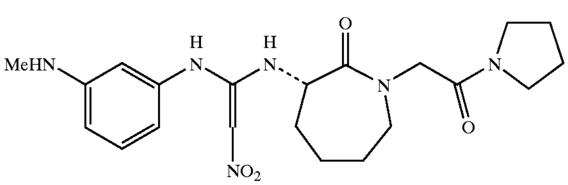 | 1-[[(3S)-Hexahydro-3-[[1-[[3-(methylamino)phenyl]amino]-2-nitroethenyl]amino]-2-oxo-1H-azepin-1-yl]acetyl]pyrrolidine | HPLC (method A) $t_R$ 2.28 min; MS (ESI, pos. ion spectrum) m/z 431 |
| 49 | 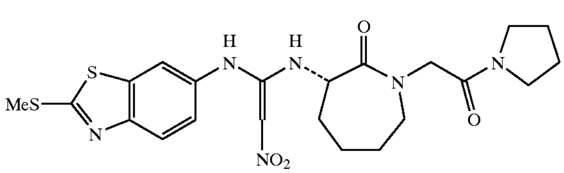 | 1-[[(3S)-Hexahydro-3-[[1-[[2-(methylthio)-6-benzothiazolyl]amino]-2-nitroethenyl]amino]-2-oxo-1H-azepin-1-yl]acetyl]pyrrolidine | HPLC (method A) $t_R$ 3.40 min; MS (ESI, pos. ion spectrum) m/z 505 |

-continued

| Ex. | Structure | Name | Characterization |
|---|---|---|---|
| 50 | 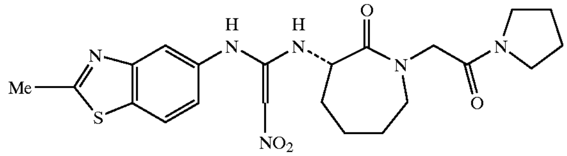 | 1-[[(3S)-Hexahydro-3-[[1-[(2-methyl-5-benzothiazolyl)amino]-2-nitroethenyl]amino]-2-oxo-1H-azepin-1-yl]acetyl]pyrrolidine | HPLC (method A) t_R 3.06 min; MS (ESI, pos. ion spectrum) m/z 473 |
| 51 | 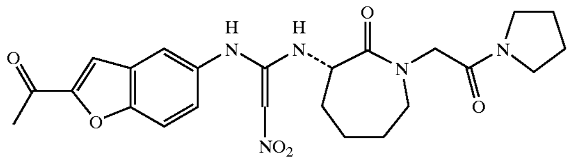 | 1-[[(3S)-3-[[1-[(2-Acetyl-5-benzofuranyl)amino)-2-nitroethenyl]amino]hexahydro-2-oxo-1H-azepin-1-yl]acetyl]pyrrolidine | HPLC (method A) t_R 2.97 min; MS (ESI, pos. ion spectrum) m/z 484 |
| 52 | 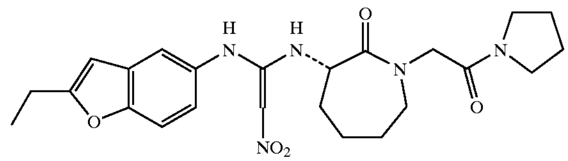 | 1-[[(3S)-3-[[1-[(2-Ethyl-5-benzofuranyl)amino]-2-nitroethenyl]amino]hexahydro-2-oxo-1H-azepin-1-yl]acetyl]pyrrolidine | HPLC (method A) t_R 3.72 min; C MS (ESI, pos. ion spectrum) m/z 470 |
| 53 | 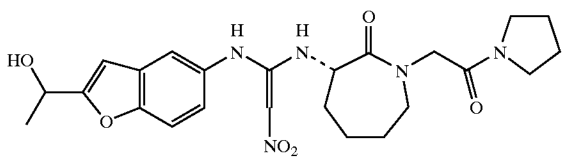 | 1-[[(3S)-Hexahydro-3-[[1-[[2-(1-hydroxyethyl)-5-benzofuranyl]amino]-2-nitroethenyl]amino]-2-oxo-1H-azepin-1-yl]acetyl]pyrrolidine | HPLC (method A) t_R 2.99 min; MS (ESI, pos. ion spectrum) m/z 486 |
| 54 | 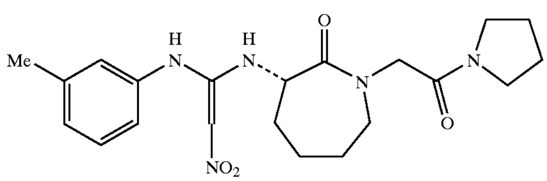 | 1-[[(3S)-Hexahydro-3-[[1-[3-methylphenyl)amino]-2-nitroethenyl]amino]-2-oxo-1H-azepin-1-yl]acetyl]pyrrolidine | HPLC (method A) t_R 3.12 min; MS (ESI, pos. ion spectrum) m/z 416 |
| 55 | 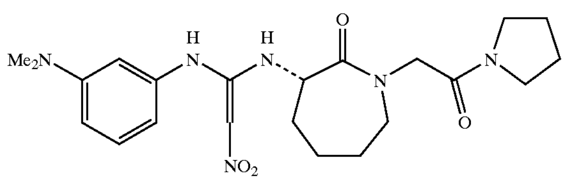 | 1-[[(3S)-3-[[1-[3-(Dimethylamino)phenyl]amino]-2-nitroethenyl]amino]hexahydro-2-oxo-1H-azepin-1-yl]acetyl]pyrrolidine | HPLC (method A) t_R 2.46 min; MS (ESI, pos. ion spectrum) m/z 445 |
| 56 | 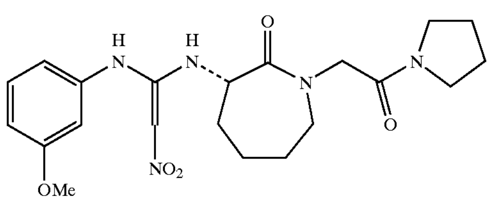 | 1-[[(3S)-Hexahydro-3-[[1-[(3-methoxyphenyl)amino]-2-nitroethenyl]amino]-2-oxo-1H-azepin-1-yl]acetyl]pyrrolidine | HPLC (method A) t_R 2.99 min; MS (ESI, pos. ion spectrum) m/z 432 |
| 57 | 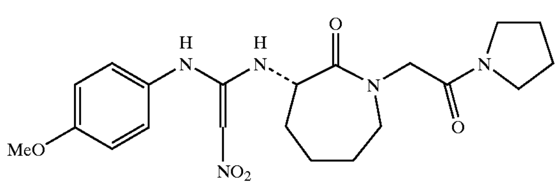 | 1-[[(3S)-Hexahydro-3-[[1-[(4-methoxyphenyl)amino]-2-nitroethenyl]amino]-2-oxo-1H-azepin-1-yl]acetyl]pyrrolidine | HPLC (method A) t_R 2.90 min; MS (ESI, pos. ion spectrum) m/z 432 |

| Ex. | Structure | Name | Characterization |
|---|---|---|---|
| 58 | 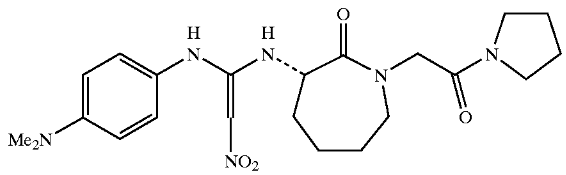 | 1-[[(3S)-3-[[1-[4-(Dimethylamino)phenyl]amino]-2-nitroethenyl]amino]hexahydro-2-oxo-1H-azepin-1-yl]acetyl]pyrrolidine | HPLC (method A) $t_R$ 2.21 min; MS (ESI, pos. ion spectrum) m/z 445 |
| 59 | 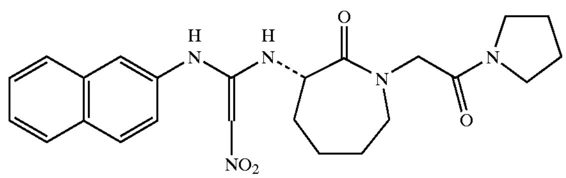 | 1-[[(3S)-Hexahydro-3-[[1-(2-naphthalenylamino)-2-nitroethenyl]amino]-2-oxo-1H-azepin-1-yl]acetyl]pyrrolidine | HPLC (method A) $t_R$ 3.45 min; MS (ESI, pos. ion spectrum) m/z 452 |
| 60 | 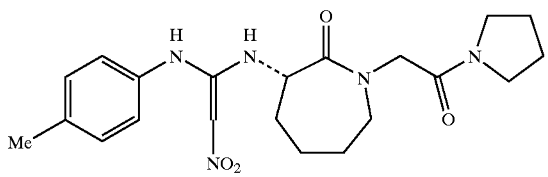 | 1-[[(3S)-Hexahydro-3-[[1-[[4-methylphenyl)amino]-2-nitroethenyl]amino]-2-oxo-1H-azepin-1-yl]acetyl]pyrrolidine | HPLC (method A) $t_R$ 3.13 min; MS (ESI, pos. ion spectrum) m/z 416 |
| 61 | 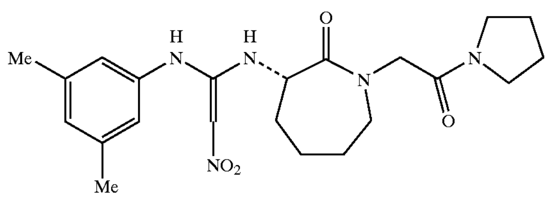 | 1-[[(3S)-3-[[1-[(3,5-Dimethylphenyl)amino]-2-nitroethenyl]amino]hexahydro-2-oxo-1H-azepin-1-yl]acetyl]pyrrolidine | HPLC (method A) $t_R$ 3.41 min; MS (ESI, pos. ion spectrum) m/z 430 |
| 62 | 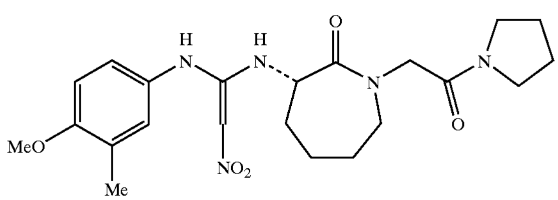 | 1-[[(3S)-Hexahydro-3-[[1-[(4-methoxy-3-methylphenyl)amino]-2-nitroethenyl]amino]-2-oxo-1H-azepin-1-yl]acetyl]pyrrolidine | HPLC (method A) $t_R$ 3.30 min; MS (ESI, pos. ion spectrum) m/z 446 |
| 63 | 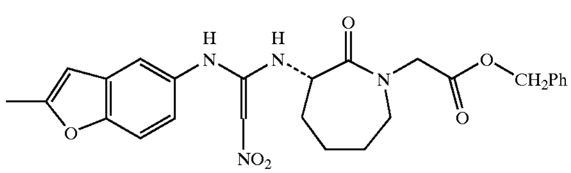 | (3S)-Hexahydro-3-[[1-[(2-methyl-5-benzofuranyl)amino]-2-nitroethenyl]amino]-2-oxo-1H-azepine-1-acetic acid, phenylmethyl ester | HPLC method A) $t_R$ 4.06 min; MS (ESI, pos. ion spectrum) m/z 493 |

EXAMPLE 64

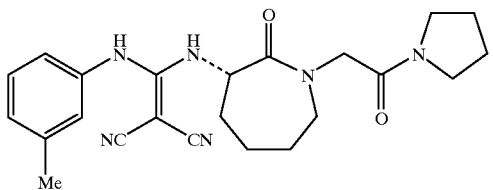

1-[[(3S)-3-[[2,2-Dicyano-1-[(3-methylphenyl)amino]ethenyl]amino]hexahydro-2-oxo-1H-azepin-1-yl]acetyl]pyrrolidine 3-Methylaniline (32.2 mg, 0.250 mmol) and [bis(methylthio)methylene]propanedinitrile (35.5 mg, 0.209 mmol) were dissolved in ethanol(0.3 mL). The reaction mixture was heated at 80° C. for 3 h. To the mixture was added 1-[[(3S)-3-aminohexahydro-2-oxo-1H-azepin-1-yl]acetyl]pyrrolidine (50.0 mg, 0.209 mmol) and the reaction mixture was heated at 80° C. for another 40 h. Purification by preparative RP HPLC provided the title compound as a pale yellow solid (22 mg, 45%): MS (ESI, pos. ion spectrum) m/z 421; HPLC (method A) $t_R$ 3.39 min.

EXAMPLES 65–77

Using the procedure described in Example 64, the following compounds were prepared.

| Ex. | Structure | Name | Characterization |
|---|---|---|---|
| 65 | 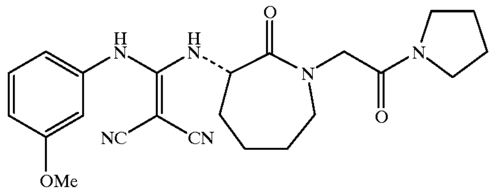 | 1-[[(3S)-3-[[2,2-Dicyano-1-[(3-methoxyphenyl)amino]ethenyl]amino]hexahydro-2-oxo-1H-azepin-1-yl]acetyl]pyrrolidine | HPLC (method A) $t_R$ 3.24 min; MS (ESI, pos. ion spectrum) m/z 437 |
| 66 | 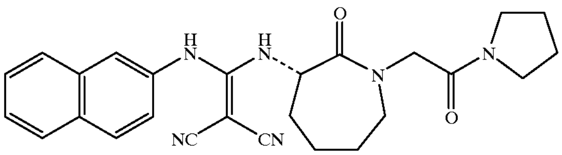 | 1-[[(3S)-3-[[2,2-Dicyano-1-(2-naphthalenylamino)ethenyl]amino]hexahydro-2-oxo-1H-azepin-1-yl]acetyl]pyrrolidine | HPLC (method A) $t_R$ 3.61 min; MS (ESI, pos. ion spectrum) m/z 457 |
| 67 | 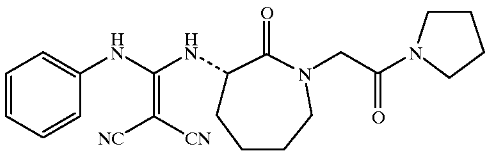 | 1-[[(3S)-3-[[2,2-Dicyano-1-(phenylamino)ethenyl]amino]hexahydro-2-oxo-1H-azepin-1-yl]acetyl]pyrrolidine | HPLC (method A) $t_R$ 3.14 min; MS (ESI, pos. ion spectrum) m/z 407 |
| 68 | 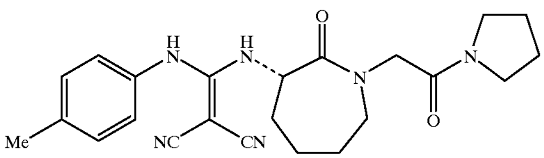 | 1-[[(3S)-3-[[2,2-Dicyano-1-[(4-methylphenyl)amino]ethenyl]amino]hexahydro-2-oxo-1H-azepin-1-yl]acetyl]pyrrolidine | HPLC (method A) $t_R$ 3.41 min; MS (ESI, spectrum) m/z 421 |
| 69 | 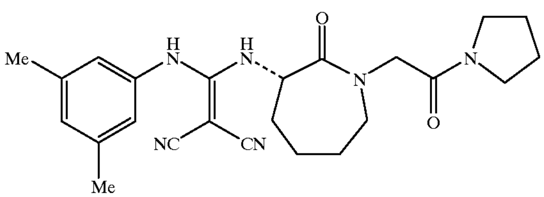 | 1-[[(3S)-3-[[2,2-Dicyano-1-[(3,5-dimethylphenyl)amino]ethenyl]amino]hexahydro-2-oxo-1H-azepin-1-yl]acetyl]pyrrolidine | HPLC (method A) $t_R$ 3.62 min; MS (ESI, pos. ion spectrum) m/z 435 |
| 70 | 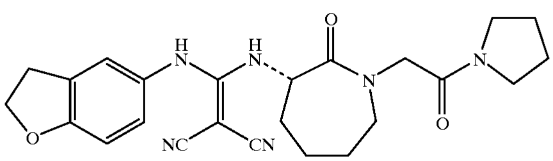 | 1-[[(3S)-3-[[2,2-Dicyano-1-[(2,3-dihydro-5-benzofuranyl)amino]ethenyl]amino]hexahydro-2-oxo-1H-azepin-1-yl]acetyl]pyrrolidine | HPLC (method A) $t_R$ 3.19 min; MS (ESI, pos. ion spectrum) m/z 449 |
| 71 | 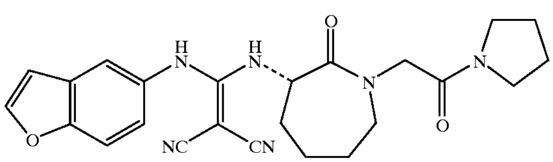 | 1-[[(3S)-3-[[1-(5-Benzofuranylamino)-2,2-dicyanoethenyl]amino]hexahydro-2-oxo-1H-azepin-1-yl]acetyl]pyrrolidine | HPLC (method A) $t_R$ 3.33 min; C MS (ESI, pos. ion spectrum) m/z 447 |
| 72 | 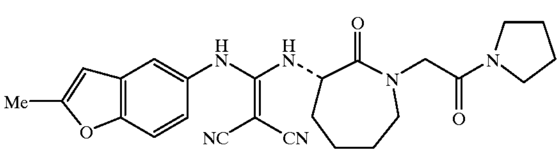 | 1-[[(3S)-3-[[2,2-Dicyano-1-[(2-methyl-5-benzofuranyl)amino]ethenyl]amino]hexahydro-2-oxo-1H-azepin-1-yl]acetyl]pyrrolidine | HPLC (method A) $t_R$ 3.57 min; MS (ESI, pos. ion spectrum) m/z 461 |

| Ex. | Structure | Name | Characterization |
|---|---|---|---|
| 73 | 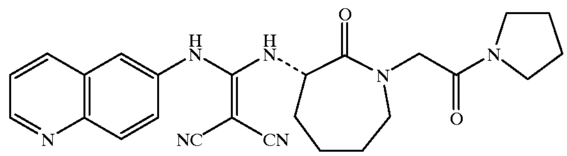 | 1-[[(3S)-3-[[2,2-Dicyano-1-(6-quinolinylamino)ethenyl]amino]hexahydro-2-oxo-1H-azepin-1-yl]acetyl]pyrrolidine | HPLC (method A) $t_R$ 2.20 min; MS (ESI, pos. ion spectrum) m/z 458 |
| 74 | 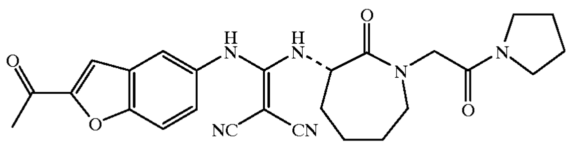 | 1-[[(3S)-3-[[1-[(2-Acetyl-5-benzofuranyl)amino]-2,2-dicyanoethenyl]amino]hexahydro-2-oxo-1H-azepin-1-yl]acetyl]pyrrolidine | HPLC (method A) $t_R$ 3.20 min; MS (ESI, pos. ion spectrum) m/z 489 |
| 75 | 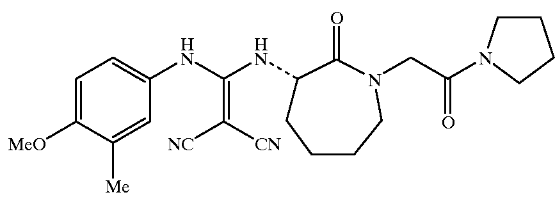 | 1-[[(3S)-3-[[2,2-Dicyano-1-[(4-methoxy-3-methylphenyl)amino]ethenyl]amino]hexahydro-2-oxo-1H-azepin-1-yl]acetyl]pyrrolidine | HPLC (method A) $t_R$ 3.51 min; MS (ESI, pos. ion spectrum) m/z 451 |
| 76 | 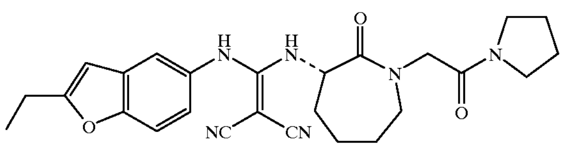 | 1-[[(3S)-3-[[2,2-Dicyano-1-[(2-ethyl-5-benzofuranyl)amino]ethenyl]amino]hexahydro-2-oxo-1H-azepin-1-yl]acetyl]pyrrolidine | HPLC (method A) $t_R$ 3.87 min; MS (ESI, pos. ion spectrum) m/z 475 |
| 77 | 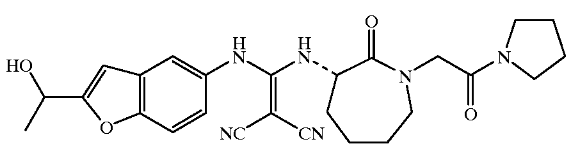 | 1-[[(3S)-3-[[2,2-Dicyano-1-[[2-(1-hydroxyethyl)-5-benzofuranyl]amino]ethenyl]amino]hexahydro-2-oxo-1H-azepin-1-yl]acetyl]pyrrolidine | HPLC (method A) $t_R$ 3.25 min; MS (ESI, pos. ion spectrum) m/z 491 |

EXAMPLE 78

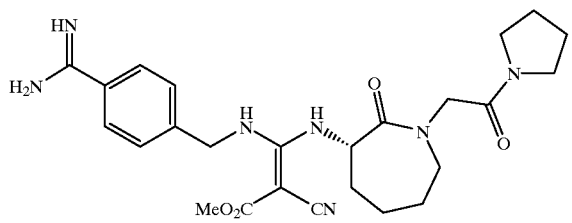

A. Preparation of 1-[[(3S)-hexahydro-3-isothiocyanato-2-oxo-1H-azepin-1-yl]acetyl]pyrrolidine. A solution of 1-[[(3S)-3-aminohexahydro-2-oxo-1H-azepin-1-yl]acetyl]pyrrolidine (1.0 g, 4.2 mmol) and 1,1'-carbonothionybis-2(1H)-pyridone (0.97 g, 4.2 mmol) in chloroform (8.4 mL) was stirred at ambient temperature for 3 h. Flash chromatography (silica, 50 mm dia column, 1% methanol/dichloromethane) afforded 1-[[(3S)-hexahydro-3-isothiocyanato-2-oxo-1H-azepin-1-yl]acetyl]pyrrolidine (1.1 g, 92%): LC-MS (ESI, pos. ion spectrum, method C) m/z, $t_R$ 282 (M+H), 2.1 min.

B. Preparation of 2-Cyano-3-[[(3S)-hexahydro-2-oxo-1-[2-oxo-2-(1-pyrrolidinyl)ethyl]-1H-azepin-3-yl]amino]-3-[[[4-[[[(phenylmethoxy)carbonyl]amino]iminomethyl]phenyl]methyl]amino]propenoic acid methyl ester. Sodium hydride (60% oil dispersion, 56 mg, 1.4 mmol) was added to a stirring solution of methyl cyanoacetate (99 mg, 0.088 mL, 1.0 mmol) in dimethylformamide (4.4 mL). After stirring at ambient temperature for 10 min, 1-[[(3S)-hexahydro-3-isothiocyanato-2-oxo-1H-azepin-1-yl]acetyl]pyrrolidine (0.28 g, 1.0 mmol) in dimethylformamide (1.0 mL) was added. After stirring an additional 30 min, phenylmethyl [[4-(aminomethyl)phenyl]iminomethyl]carbamate (0.39 g, 1.1 mmol), WSC (0.31 g, 1.6 mmol), DMAP (0.01 g, 0.1 mmol), and triethylamine (0.15 mL, 1.1 mmol) were all added and the resultant solution was stirred at 50° C. Mercury (II) chloride (0.27 g) was then added. After stirring at 50° C. for an additional hour, the reaction was transferred to a separatory funnel with ethyl acetate/water. Extraction with ethyl acetate (2×), washing with water and brine, and drying over magnesium sulfate afforded 0.4 g of crude product. Flash chromatography (silica, 25 mm dia column, 2% methanol/dichloromethane) afforded the desired product (90 mg, 14%): LRMS (ESI, pos. ion spectrum) m/z 630 (M+H).

C. Preparation of title compound. A mixture of the part B compound (80 mg, 0.13 mmol) and 10% palladium on carbon (10 mg) in methanol (1 mL) was stirred at ambient temperature under a balloon of hydrogen. After 8 h, the reaction was filtered through CELITE, and the pad was rinsed with methanol. Evaporation of the solvent afforded crude product. Preparative HPLC (Shimadzu VP-ODS 20×100 mm, 20 mL/min.; 0% B to 100% B over 10 min and 100% B for 2 min, the fractions were collected in tubes containing saturated sodium bicarbonate (0.4 mL)), evaporation of the product-containing fractions and then extraction of the residue with dichloromethane afforded the title compound (8 mg, 12% yield): LRMS (ESI, pos. ion spectrum) m/z 496 (M+H); HPLC (Method A) $t_R$ 2.4 min.

EXAMPLE 79

Using the procedure described in Example 78 the following example was prepared.

form (2.0 mL). The resulting solution was stirred at room temperature for 3 h, and then concentrated. The residue was chromatographed (silica, 0 to 10% ethyl acetate/dichloromethane) to afford 3-isothiocyanatobenzothiophene as an off-white solid.

B. Preparation of the title compound. To a solution of methyl cyanoacetate (0.029 mL, 0.33 mnmol) in 1 mL of DMF was added sodium hydride (11.4 mg, 0.48 mmol). The reaction mixture was stirred at room temperature for 30 min. To the reaction was then added 3-isothiocyanatobenzothiophene (57.0 mg, 0.298 mmol). The reaction mixture was stirred at room temperature for 3 h and 1-[[(3S)-3-aminohexahydro-

| Ex # | Structure | Characterization |
|---|---|---|
| 79 | 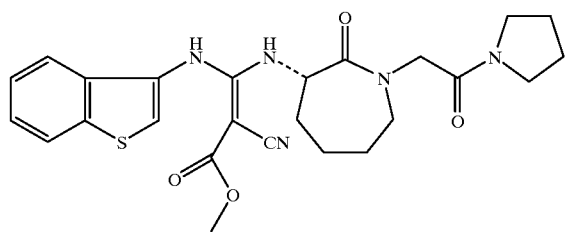 | HPLC (method A) $t_R$ = 2.5 min; LRMS (ESI, pos ion spectrum) m/z 496 (M + H) |

EXAMPLE 80

A. Preparation of 3-isothiocyanatobenzothiophene. 1,1'-carbonothionybis-2(1H)-pyridone (0.6 mmol) was added to a solution of 3-benzothiophenamine (0.6 mmol) in chloro- 2-oxo-1H-azepin-1-yl]acetyl]pyrrolidine (64.1 mg, 0.268 mmol), WSC (91.4 mg, 0.477 mmol) and DMAP (10 mg, 0.09 mmol) were then added. The reaction mixture was stirred at room temperature for 15 h and diluted with 5 mL of ethyl acetate. The organic solution was washed with brine(2×15 mL) and was concentrated in vacuo. The residue was purified by preparative HPLC (YMC ODS 30×250 mm S5 column, 25 mL/min flow, 40 min linear gradient from 0% B to 100% B) to give the title compound as a brown solid (14 mg, 10% yield): LRMS (ESI, pos. ion spectrum) m/z 496 (M+H); HPLC (Method A) $t_R$ 3.5 min.

EXAMPLES 81–82

Using the procedure described in Example 80, the following compounds were prepared.

| Ex. | Structure | Characterization |
|---|---|---|
| 81 | 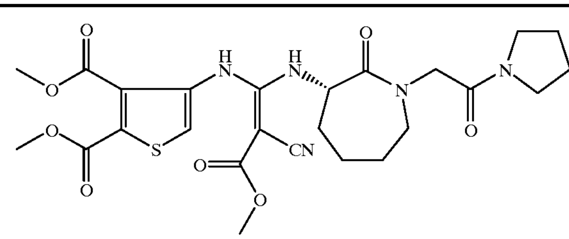 | HPLC (method A) $t_R$ 3.0 min; LRMS (ESI, pos. ion spectrum) m/z 562 (M + H) |
| 82 | 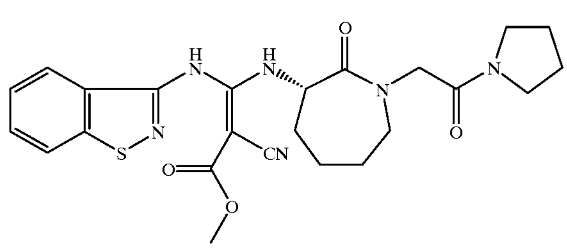 | HPLC (method A) $t_R$ 3.9 min; LRMS (ESI, pos. ion spectrum) m/z 497 (M + H) |

EXAMPLE 83–84

Using the procedure described in Example 30 and Example 80 part A, the following compounds were prepared using methyl cyanoacetate in place of dimethyl malonate.

organic extract was dried with magnesium sulfate, concentrated to an oil, and the residue was purified by flash chromatography (silica, 5% methanol/chloroform) to provide ethyl 2-cyano-3-mercapto-3-[(3-methylphenyl)amino]-2-propenoate (1.19 g, 44%) as an oil.

| Ex. | Structure | Characterization |
|---|---|---|
| 83 | 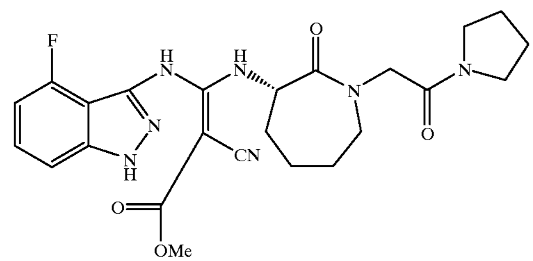 | HPLC (method A) $t_R$ 3.6 min; LRMS (ESI, pos. ion spectrum) m/z 498 (M + H) |
| 84 | 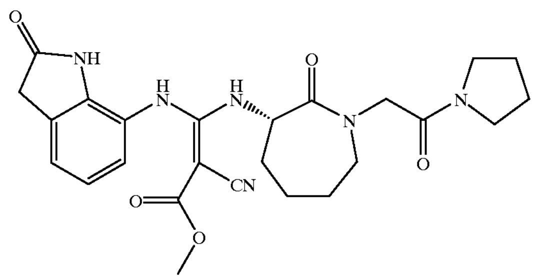 | HPLC (method A) $t_R$ 2.8 min; LRMS (ESI, pos. ion spectrum) m/z 495 (M + H) |

EXAMPLE 85

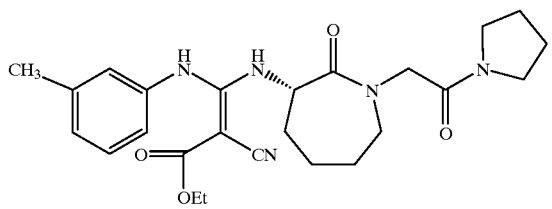

A. Preparation of ethyl 2-cyano-3-mercapto-3-[(3-methylphenyl)amino]-2-propenoate. To a solution of ethyl cyanoacetate (1.2 g, 10.3 mmol) and N,N-diisopropylethylamine (2.1 g, 16. mmol) in DMF (20 mL) was added 3-isothiocyanatotoluene (2.31 g, 15.5 mmol). After stirring for 8 h at room temperature, the mixture was poured into water (100 mL) containing 5% aqueous $KHSO_4$ (20 mL) and extracted with ethyl acetate (100 mL). The B. Peparation of title compound. To a solution of ethyl 2-cyano-3-mercapto-3-[(3-methylphenyl)amino]-2-propenoate (216 mg, 0.82 mmol) in DMF (1 mL) was added WSC (236 mg, 1.23 mmol) and 1-[[(3S)-3-aminohexahydro-2-oxo-1H-azepin-1-yl]acetyl]pyrrolidine (196 mg, 0.82 mmol). After 1 day at room temperature, the DMF was removed in vacuo. The residue was dissolved in chloroform (3 mL), washed with water (1 mL), dried with magnesium sulfate, and then concentrated to an oil. Purification by flash chromatography (silica, 5% methanol/chloroform) provided the title compound as a light yellow foam (194 mg, 51%): LCMS (ESI, positive ion spectrum, method C), m/z 468 (M+H), $t_R$ 3.7 min.

EXAMPLE 86

Using methodology described for example 85, the following compound was prepared from t-butyl cyanoacetate. Purification by flash chromatography (silica gel) was performed with 1% methanol/chloroform.

| Ex. | Structure | characterization |
|---|---|---|
| 86 | 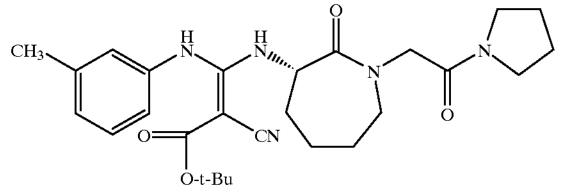 | LCMS (ESI, positive ion spectrum, method C), m/z 496 (M + H), $t_R$ 4.2 min. |

EXAMPLE 87

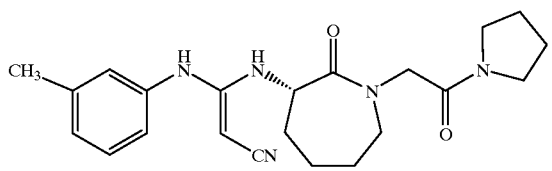

Preparation of the title compound. To a solution of Example 86 compound (64 mg, 0.13 mmol) in dichloromethane (1 mL) was added TFA (1 mL). After 1 hour at room temperature, the volatiles were removed in vacuo. Flash chromatography (silica gel, 5% methanol/chloroform) of the residue provided the title compound as an oil (36 mg, 35%): LCMS (ESI, positive ion spectrum, method C), m/z 396 (M+H), $t_R$ 2.8 min.

EXAMPLE 88

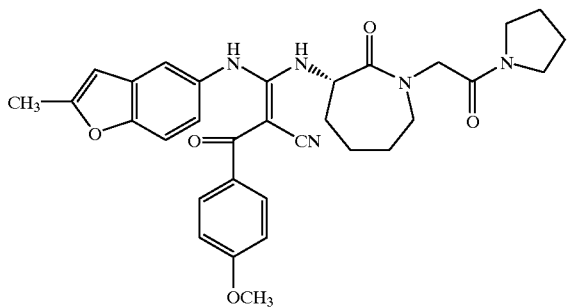

Preparation of the title compound. To a solution of 2-methyl-5-benzofuranamine (23 mg, 0.15 mmol) in acetonitrile (0.5 mL) was added α-[bis(methylthio)methylene]-4-methoxy-β-oxobenzenepropanenitrile (44 mg, 0.15 mmol). This mixture was heated at 85° C. for 16 h in a capped vial. To the reaction mixture was then added 1-[[(3S)-3-aminohexahydro-2-oxo-1H-azepin-1-yl]acetyl]pyrrolidine (36 mg, 0.15 mmol) and the mixture was heated at 85° C. in a capped vial for an additional 21 h. The solvent was removed and the residue passed through a 5-g column of C18-silica eluting with 60% methanol/water. The title compound was isolated as a tan oil (16 mg, 19%): LCMS (ESI, positive ion spectrum, method C), m/z 570 (M+H), $t_R$ 3.9 min.

EXAMPLES 89–93

Using the methodology described for example 88, the following compounds were prepared.

The following modifications in the purification processes were made: for example 89 elution from a column of C18-silica (15 mm dia) with 70% methanol/water was followed by preparative TLC (250 μM plate, 5% methanol/chloroform); for example 90, flash chromatography (silica gel, 1% methanol/chloroform) was followed by elution from a 2-g C18-silica cartridge with 70% methanol/water; for example 91, flash chromatography (silica, 2% methanol/chloroform) was followed by preparative TLC (500 μM plate, 5% methanol/chloroform).

Examples 92 and 93 were produced at 70° C. in acetonitrile. Example 92 was purified by elution from a 2-g C18-silica cartridge with 70% methanol/water followed by flash chromatography (silica, 2% methanol/chloroform). Example 93 was purified by flash chromatography (silica, 5% methanol/chloroform).

| Ex. | Structure | characterization |
|---|---|---|
| 89 | 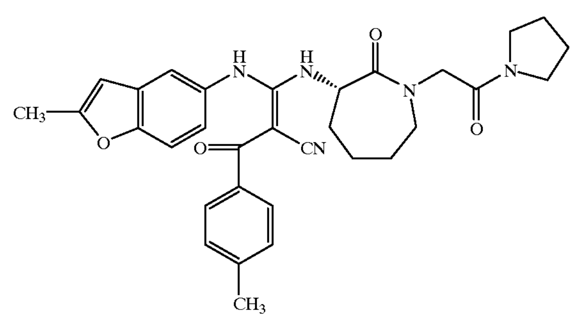 | LCMS (ESI, positive ion spectrum, method C), m/z 554 (M + H), $t_R$ 4.0 min. |
| 90 | 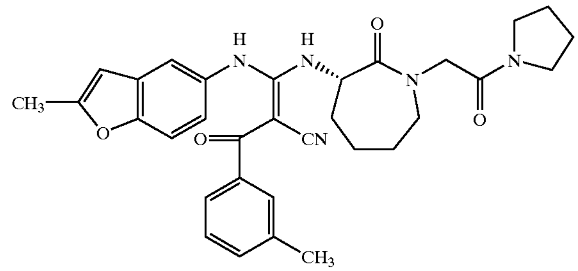 | LCMS (ESI, positive ion spectrum, method C), m/z 554 (M + H), $t_r$ 4.0 min. |

| Ex. | Structure | characterization |
|---|---|---|
| 91 | 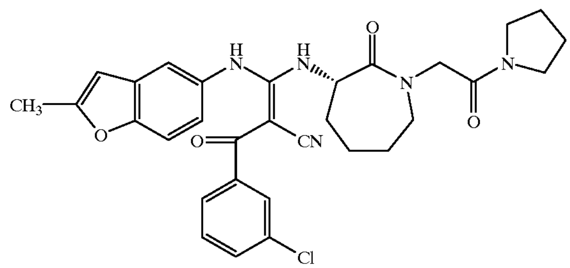 | LCMS (ESI, positive ion spectrum, method C), m/z 574/576 (M + H) $t_R$ 4.1 min. |
| 92 | 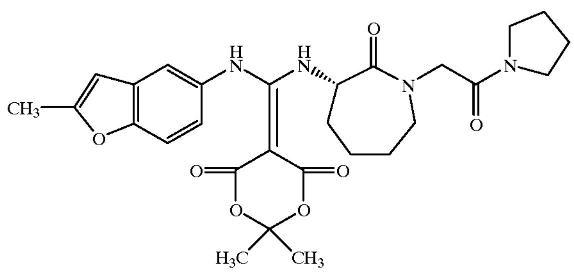 | LCMS (ESI, positive ion spectrum, method C), m/z 539 (M + H), $t_R$ 3.6 min. |
| 93 | 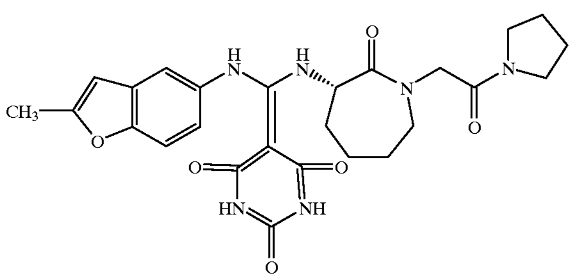 | LCMS (ESI, positive ion spectrum, method C), m/z 523 (M + H), $t_R$ 3.3 min. |

EXAMPLE 94

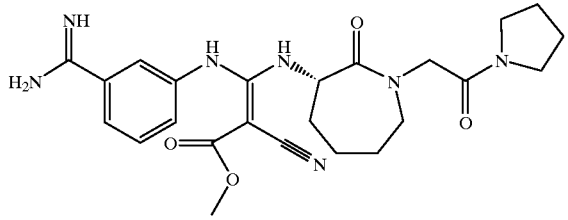

A. Preparation of 1,1-dimethylethyl [imino(3-nitrophenyl)methyl]carbamate. To a solution of 3-nitrobenzenecarboxamidine hydrochloride (5.00 g, 24.8 mmol) in 60 mL of 1:1 mixture of THF:H₂O was added 2 N NaOH aqueous solution (24.8 mL, 49.6 mmol). To the mixture was added bis(1,1-dimethylethyl) dicarbonate (5.40 g, 24.8 mmol). The reaction mixture was stirred at room temperature for 16 h. The reaction mixture was extracted with ethyl acetate(3×100 mL). The combined organic layers were dried over sodium sulfate and concentrated to give 1,1-dimethylethyl [imino(3-nitrophenyl)methyl]carbamate (6.59 g, 100% yield).

B. Preparation of 1,1-dimethylethyl [(3-aminophenyl)iminomethyl]carbamate. To a solution of 1,1-dimethylethyl [imino(3-nitrophenyl)methyl]carbamate (1.32 g, 5.00 mmol) in 25 mL of methanol was added 10% Pd/C (130 mg). Then reaction mixture was stirred under a hydrogen-filled balloon at room temperature for 20 h. The reaction mixture was filtered through CELITE. The filtrate was concentrated to give 1,1-dimethylethyl [(3-aminophenyl)iminomethyl]carbamate (1.20 g, 100% yield).

C. Preparation of the title compound. 1,1-dimethylethyl [(3-aminophenyl)iminomethyl]carbamate ( 118 mg, 0.50 mmol) and ethyl 2-cyano-3,3-bis(methylthio)-2-propenoate (102 mg, 0.50 mmol) were dissolved in DMF (0.5 mL). The reaction mixture was stirred at 64° C. for 20 h. To the reaction mixture were added 1-[[(3S)-3-aminohexahydro-2-oxo-1H-azepin-1-yl]acetyl]pyrrolidine (120 mg, 0.5 mmol) and mercury (II) chloride (136 mg, 0.5 mmol). After 2 h at 64° C., ethyl acetate (25 mL) was added and the mixture washed with brine (20 mL×2), dried with sodium sulfate, and then concentrated. The residue was purified by preparative HPLC (YMC C-18 column; linear gradient elution) to provide the title compound (8.0 mg, 3%): HPLC (method A) $t_R$ 1.8 min; LCMS (ESI, pos. ion spectrum) m/z 482 (M+H).

EXAMPLES 95–96

Using the procedure described in example 94, the following compounds were prepared

| Ex. | structure | characterization |
|---|---|---|
| 95 | 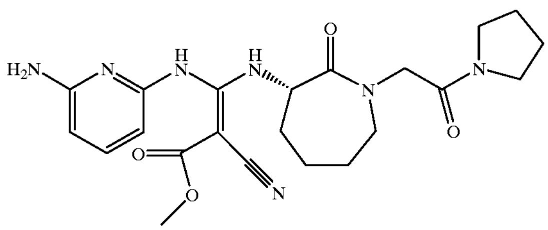 | HPLC (method C) $t_R$ (2.9 min; LCMS (ESI, pos. ion spectrum) m/z 456 (M + H). |
| 96 | 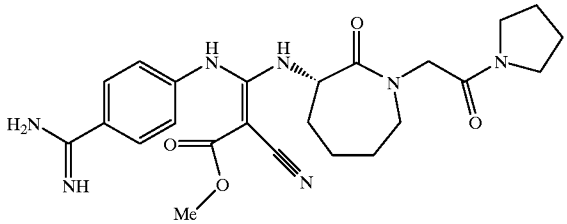 | HPLC (method C) $t_R$ 1.8 min; LCMS (ESI, pos. ion spectrum) m/z 482 (M + H). |

EXAMPLE 97

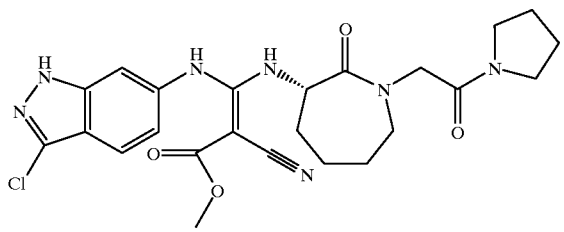

A. Preparation of 3-chloro-6-nitro-1H-indazole. To a solution of 6-nitro-1H-indazole (1.63 g, 10.0 mmol) in 15 mL of THF and 0.15 mL of 0.1N HCl was added 2-chloro-1H-isoindole-1,3(2H)-dione (1.36 g, 10.2 mmol) in portions. The reaction mixture was stirred at room temperature for 20 h. To the reaction mixture was added water (75 mL). A yellow precipitate formed which was collected by filtration, washed with 1/1 water:methanol to provided 3-chloro-6-nitro-1H-indazole (1.76 g, 89% yield).

B. Preparation of 3-chloro-1H-indazole-6-amine. To a solution of 3-chloro-6-nitro-1H-indazole (1.76 g, 8.91 mmol) in 22 mL of methanol was added 10% Pd/C (200 mg). The mixture stirred under a hydrogen-filled balloon at room temperature for 4 h. The reaction mixture was filtered through CELITE. The filtrate was concentrated to give 3-chloro-1H-indazole-6-amine (1.45 g, 97% yield).

C. Preparation of 3-chloro-6-isothiocyanato-1H-indazole. A solution of 3-chloro-1H-indazole-6-amine (1.45 g 8.70 mmol) and 1,1'-carbonothionybis-2(1H)-pyridone (2.01 g, 8.70 mmol) in dichloromethane (40 mL) was stirred at room temperature for 20 h. The reaction was concentrated and purified by flash chromatography (silica, 20% ethyl acetate/hexane) to give 3-chloro-6-isothiocyanato-1H-indazole (982 mg, 54% yield).

D. Preparation of the title compound. To the solution of methyl cyanoacetate (0.030 g, 0.30mmol) in 0.5 mL DMF, 60% sodium hydride (12.0 mg, 0.30 mmol) was added. The reaction mixture was stirred at room temperature for 30 min and then 3-chloro-6-isothiocyanato-1H-indazole (0.063 g, 0.30 mmol) was added. The reaction mixture was stirred at room temperature for 3 h. To the mixture was added 1-[[(3S)-3-aminohexahydro-2-oxo-1H-azepin-1-yl]acetyl]pyrrolidine (0.072, 0.30 mmol) and mercury (II) chloride (0.081 g, 0.030 mmol ). After 30 min, the reaction mixture was diluted with 1.5 mL of methanol and filtered. The filtrate was concentrated and the residue was purified by preparative HPLC (YMC C-18 column; linear gradient elution) to give the title compound (0.013 g, 9% yield ): HPLC (method A), $t_R$ 2.9 min; LCMS (ESI, pos. ion spectrum) m/z 514/516 (M+H).

EXAMPLE 98

Using the procedure described in example 97, the following compound was prepared:

| Ex. | structure | characterization |
|---|---|---|
| 98 | 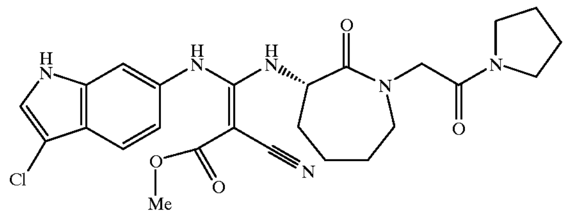 | HPLC (method A) $t_R$ 3.3 min; LCMS (ESI, pos. ion spectrum) m/z 513/515 (M + H). |

EXAMPLE 99

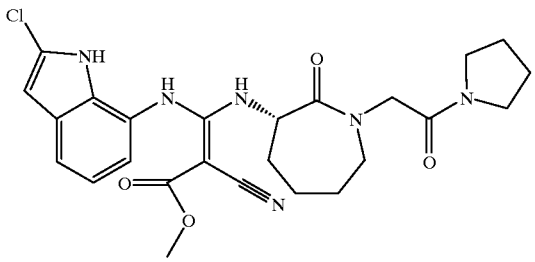

A. Preparation of 2-chloro-1H-indole-7-amine. To a solution of 2-chloro-7-nitro-1H-indole (1.3 g, 6.6 mmol) in 65 mL of methanol was added 1.3 g of 50% Raney Ni and hydrazine monohydrate (0.29 mL, 10 mmnol). The mixture was stirred at room temperature for 1 hour and then filtered through CELITE and concentrated to give 2-chloro-1H-indole-7-amine (1.08 g, 98.0%).

B. Preparation of the title compound. Following the same procedure described in Example 971 from the part A compound the title compound was prepared: HPLC (method A), $t_R$ 3.3 min; LCMS (ESI, pos. ion spectrum) m/z 513/515 (M+H).

EXAMPLE 100

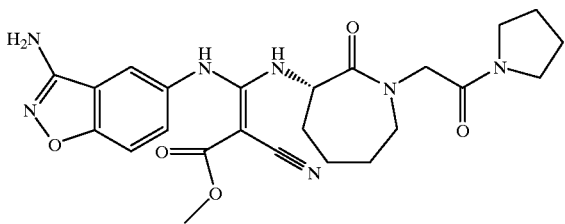

A. Preparation of bis(1,1-dimethylethyl) (5-nitro-1,2-benzisoxazol-3-yl)imidodicarbonate. To a suspension of 5-nitro-1,2-benzisoxazol-3-amine (1.88 g 10.5 mmol) and DMAP (0.25 g 2.0 mmol) in dichloromethane (50 mL)was slowly added a solution of bis(1,1-dimethylethyl) dicarbonate (5.04 g, 21 mmol) in 30 mL of dichloromethane. The mixture was stirred at room temperature for 2 h, washed with brine (50 mL), dried over sodium sulfate and concentrated to give bis(1,1-dimethylethyl) (5-nitro-1,2-benzisoxazol-3-yl)imidodicarbonate (4.0 g, 100%).

B. Preparation of 1,1-dimethylethyl (5-nitro-1,2-benzisoxazol-3-yl)carbamate. To a solution of bis(1,1-dimethylethyl) (5-nitro-1,2-benzisoxazol-3-yl) imidodicarbonate (3.6 g, 9.5 mmol) in 20 mL of dichloromethane was added TFA (1.5 mL, 19 mmol). The mixture was stirred at room temperature for 1 h and diluted with 100 mL of dichloromethane. The organic solution was washed with aqueous $NaHCO_3$ (50 mL) and brine (50 mL); dried over sodium sulfate and concentrated. The residue was purified by flash chromatography (silica, 80 g, hexane/ethyl acetate 6:1) to give 1,1-dimethylethyl (5-nitro-1,2-benzisoxazol-3-yl)carbamate (2.1 g, 75% yield).

C. Preparation of 1,1-dimethylethyl (5-amino-1,2-benzisoxazol-3-yl)carbamate. A solution of 1,1-dimethylethyl (5-nitro-1,2-benzisoxazol-3-yl)carbamate (279 mg, 1.00 mmol) and $SnCl_2 \cdot 2H_2O$ (744 mg, 3.30 mmol) in ethanol (10 mL) was heated at 70–75° C. for 1.5 h. The mixture was cooled to room temperature; neutralized by adding saturated $NaHCO_3$ and filtered through CELITE. The filtrate was extracted with ethyl acetate (3×50 mL). The combined organic layers were dried over sodium sulfate and concentrated to give 1,1-dimethylethyl (5-amino-1,2-benzisoxazol-3-yl)carbamate (224 mg, 90.0% yield).

D. Preparation of 1,1-dimethylethyl (5-isothiocyanato-1,2-benzisoxazol-3-yl)carbamate. To a solution of 1,1-dimethylethyl (5-amino-1,2-benzisoxazol-3-yl)carbamate (1.1 g, 4.4 mmol) in dichloromethane (30 mL) was added 1,1'-carbonothionybis-2(1H)-pyridone (1.0 g, 4.4 mmol). The mixture was stirred at room temperature for 4 h. The reaction was concentrated and purified by flash chromatography (silica, 12% ethyl acetate/hexane) to give 1,1-dimethylethyl (5-isothiocyanato-1,2-benzisoxazol-3-yl) carbamate (0.98 g, 77%).

E. Preparation of title compound. To a solution of methyl cyanoacetate (0.030 g, 0.30 mmol) in 0.5 mL DMF was added 60% sodium hydride (12.0 mg, 0.30 mmol). The mixture was stirred at room temperature for 20 min and 1,1-dimethylethyl (5-isothiocyanato-1,2-benzisoxazol-3-yl) carbamate (0.087 g, 0.30 mmol) was added. The reaction mixture was stirred at room temperature for 2 h. To the mixture was added 1-[[(3S)-3-aminohexahydro-2-oxo-1H-azepin-1-yl]acetyl]pyrrolidine (0.072, 0.30 mmol) and mercury (II) chloride (0.081 g, 0.030 mmol ) and the reaction mixture stirred for an additional 2 h. The reaction mixture was diluted with ethyl acetate (30 mL). The solution was washed with water (10 mL), concentrated, and the residue was dissolved in $CH_3CN$ (1 mL). To this mixture was added TFA (0.027 mL, 0.36 mmol). The mixture was stirred at 60° C. for 8 h. The reaction mixture was diluted with 1 mL of methanol and filtered, and the filtrate was purified by preparative HPLC (YMC C-18 column; linear gradient elution) to give the title compound (0.015 g, 10% yield ): HPLC (method A), $t_R$ 1.4 min; LRMS (ESI, pos. ion spectrum) m/z 496 (M+H).

EXAMPLE 101

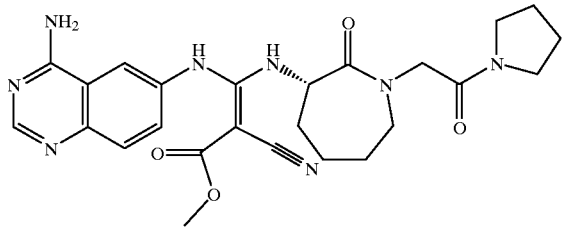

A. Preparation of 1,1-dimethylethyl (6-nitro-4-quinazolinyl) carbamate. A mixture of 6-nitro-4-quinazolinamine (4.80 g, 25.3 mmol) and bis(1,1-dimethylethyl) dicarbonate (6.63 g, 30.3 mmol) in pyridine (10 mL) was heated at 65–70° C. for 6 h. The mixture was diluted with 200 mL of ethyl acetate, washed with aqueous $CuSO_4$ solution (100 mL), brine (100 mL), dried over sodium sulfate and concentrated. The residue was purified by flash chromatography (silica, ethyl acetate/hexane) to give 1,1-dimethylethyl (6-nitro-4-quinazolinyl)carbamate (1.06 g, 14%).

B. Preparation of 1,1-dimethylethyl (6-amino-4-quinazolinyl)carbamate. To a solution of 1,1-dimethylethyl (6-nitro-4-quinazolinyl)carbamate (1.06 g, 3.66 mmol) in 20 mL of methanol was added 10% Pd/C (100 mg). The mixture stirred under a hydrogen-filled balloon at room temperature for 2 h. The reaction mixture was filtered through CELITE and concentrated to give 1,1-dimethylethyl (6-amino-4-quinazolinyl)carbamate (0.83 g 87%).

C. Preparation of the title compound. Following the same procedure described in Example 100, starting from part B compound the title compound was prepared: HPLC (method A) $t_R$ 1.7 min; LRMS (ESI, pos. ion spectrum) m/z 507 (M+H).

EXAMPLE 102

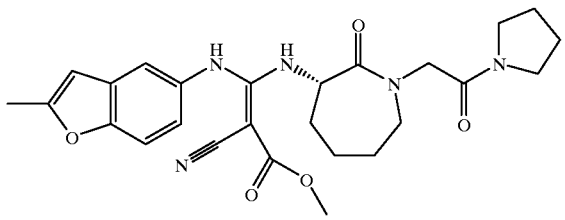

Preparation of the title compound. A solution of 2-methyl-5-benzofuranamine (73.8 mg, 0.502 mmol), methyl 2-cyano-3,3-bis(methylthio)-2-propenoate (85.0 mg, 0.418 mmol) in EtOH (1.0 mL) was heated at 80° C. for 4 hrs. To the mixture was added 1-[[(3S)-3-aminohexahydro-2-oxo-1H-azepin-1-yl]acetyl]pyrrolidine (99.9 mg, 0.418 mmol). The reaction was heated at 80° C. for an additional 40 h. The crude product was purified by flash chromatography (silica, 10% methanol in ethyl acetate) to give a white solid (101 mg, 49%): HPLC (method A) $t_R$ 3.88 min; LRMS (ESI, pos. ion spectrum) m/z 494 (M+H).

EXAMPLES 103–127

Using the procedure described in example 102, the following compounds were prepared. The required bis (methylthio) intermediates were prepared as described in Example 138.

| Ex. | structure | characterization |
|---|---|---|
| 103 | 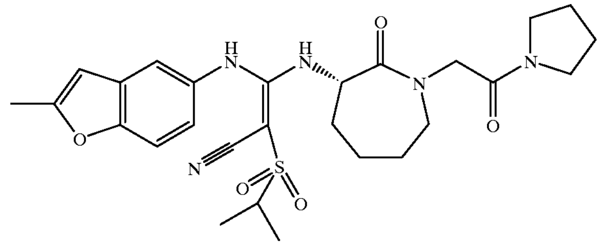 | HPLC (method A) $t_R$ 3.60 min; LRMS (ESI, pos. ion spectrum) m/z 542 (M + H) |
| 104 | 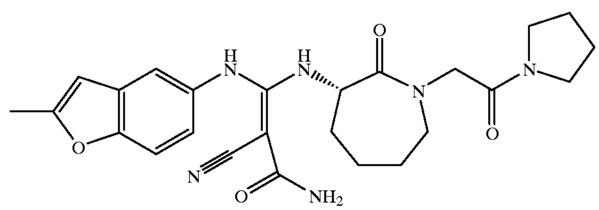 | HPLC (method A) $t_R$ 3.57 min; LRMS (ESI, pos. ion spectrum) m/z 479 (M + H) |
| 105 | 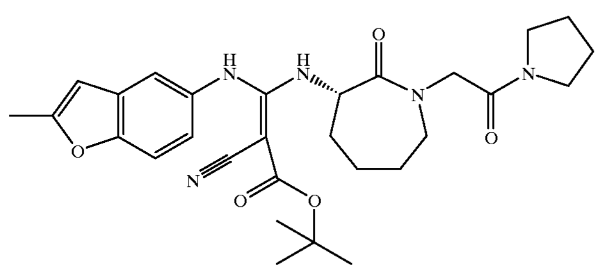 | HPLC (method A) $t_R$ 4.43 min; LRMS (ESI, pos. ion spectrum) m/z 536 (M + H) |
| 106 | 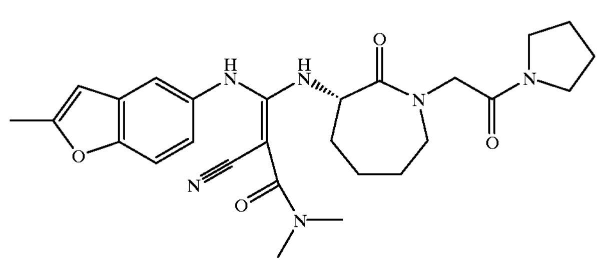 | HPLC (method A) $t_R$ 3.72 min; LRMS (ESI, pos. ion spectrum) m/z 507 (M + H) |

| Ex. | structure | characterization |
|---|---|---|
| 107 | 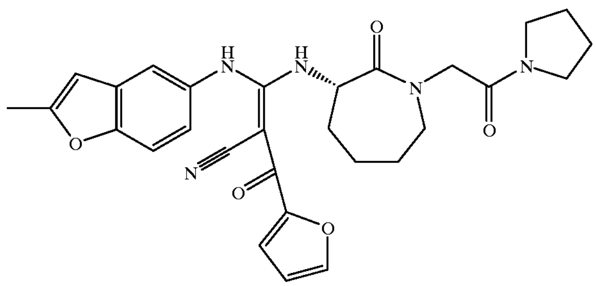 | HPLC (method A) $t_R$ 3.88 min; LRMS (ESI, pos. ion spectrum) m/z 530 (M + H) |
| 108 | 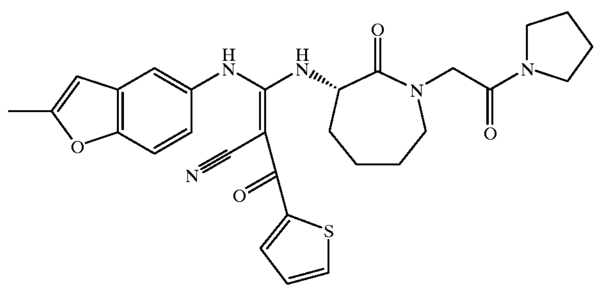 | HPLC (method A) $t_R$ 4.14 min; LRMS (ESI, pos. ion spectrum) m/z 546 (M + H) |
| 109 | 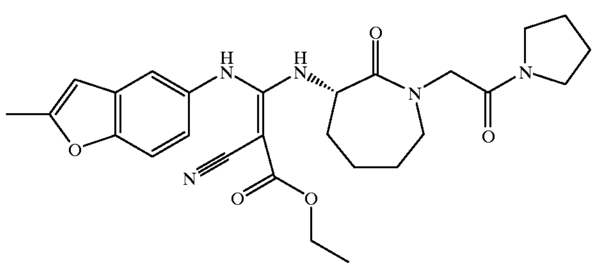 | HPLC (method A) $t_R$ 4.06 min; LRMS (ESI, pos. ion spectrum) m/z 508 (M + H) |
| 110 | 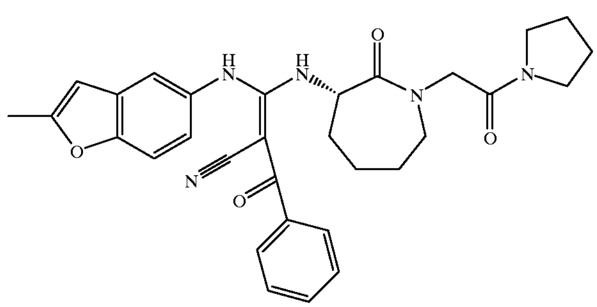 | HPLC (method A) $t_R$ 4.06 min; LRMS (ESI, pos. ion spectrum) m/z 540 (M + H) |
| 111 | 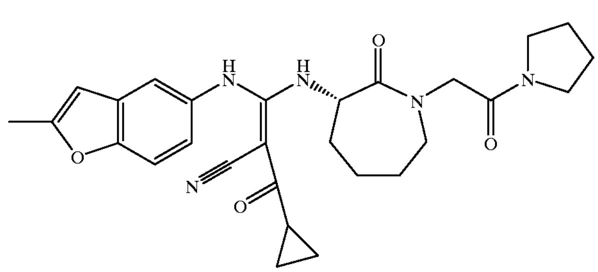 | HPLC (method A) $t_R$ 4.07 min; LRMS (ESI, pos. ion spectrum) m/z 504 (M + H) |

-continued
| Ex. | structure | characterization |
|---|---|---|
| 112 | 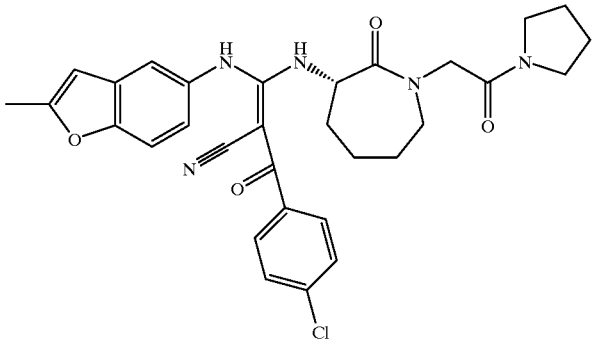 | HPLC (method A) $t_R$ 4.34 min; LRMS (ESI, pos. ion spectrum) m/z 575/577 (M + H) |
| 113 | 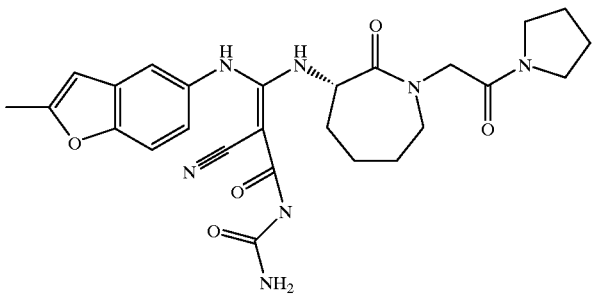 | HPLC (method A) $t_R$ 3.63 min; LRMS (ESI, pos. ion spectrum) m/z 522 (M + H) |
| 114 | 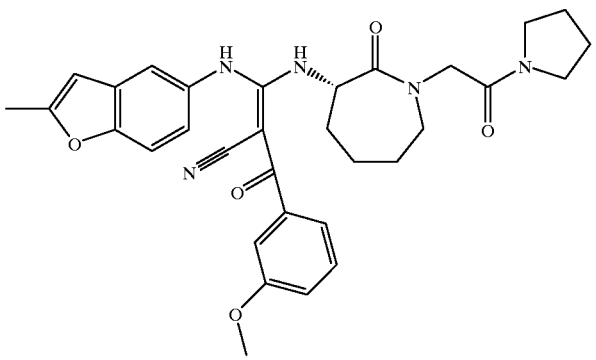 | HPLC (method A) $t_R$ 4.09 min; LRMS (ESI, pos. ion spectrum) m/z 570 (M + H) |
| 115 | 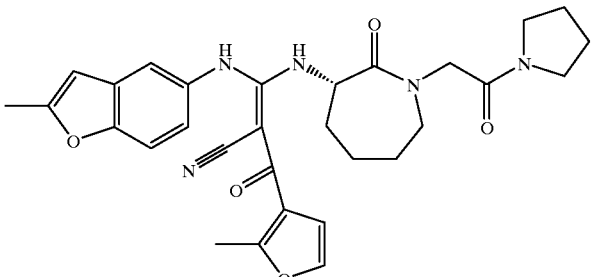 | HPLC (method A) $t_R$ 4.08 min; LRMS (ESI, pos. ion spectrum) m/z 544 (M + H) |

| Ex. | structure | characterization |
|---|---|---|
| 116 | 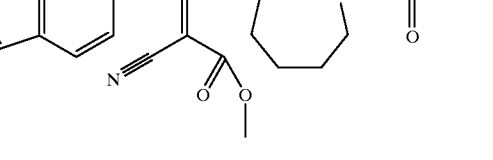 | HPLC (method A) $t_R$ 3.4 min; LRMS (ESI, pos. ion spectrum) m/z 479 (M + H) |
| 117 | 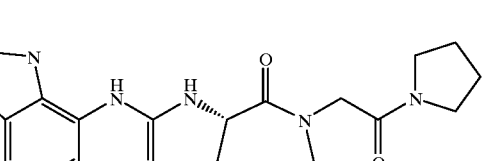 | HPLC (method A) $t_R$ 3.6 min; LRMS (ESI, pos. ion spectrum) m/z 479 (M + H) |
| 118 | 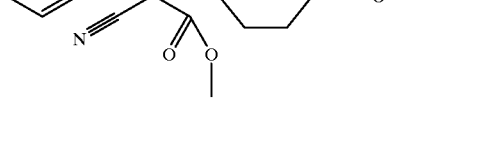 | HPLC (method A) $t_R$ 3.0 min; LRMS (ESI, pos. ion spectrum) m/z 480 (M + H) |
| 119 | 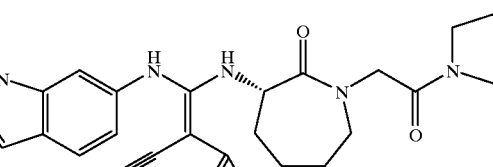 | HPLC (method A) $t_R$ 2.9 min; LRMS (ESI, pos. ion spectrum) m/z 480 (M + H) |
| 120 | 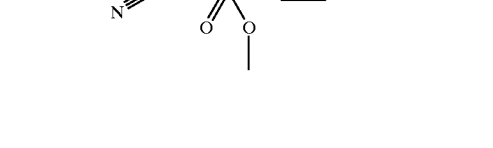 | HPLC (method A) $t_R$ 3.88 min; LRMS (ESI, pos. ion spectrum) m/z 552 (M + H) |

| Ex. | structure | characterization |
|---|---|---|
| 121 | 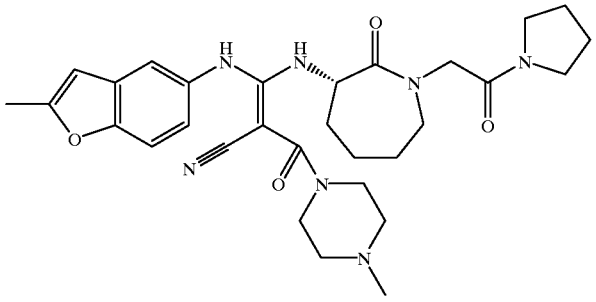 | HPLC (method A) $t_R$ 3.06 min; LRMS (ESI, pos. ion spectrum) m/z 562 (M + H) |
| 122 | 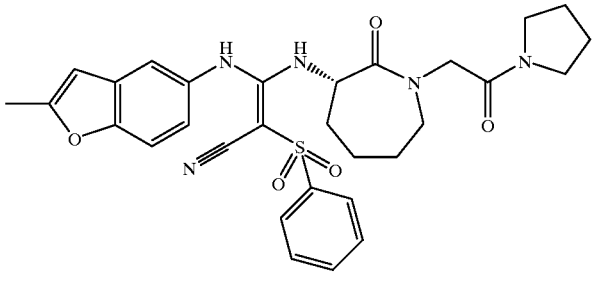 | HPLC (method A) $t_R$ 3.74 min; LRMS (ESI, pos. ion spectrum) m/z 576 (M + H) |
| 123 | 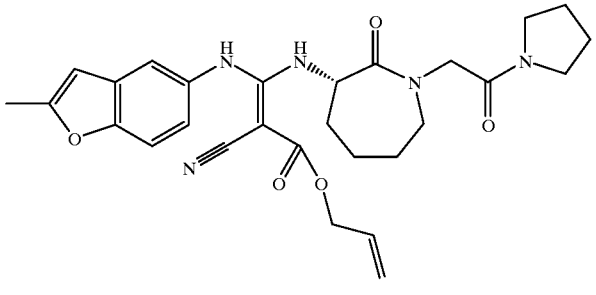 | HPLC (method A) $t_R$ 4.13 min; LRMS (ESI, pos. ion spectrum) m/z 520 (M + H) |
| 124 | 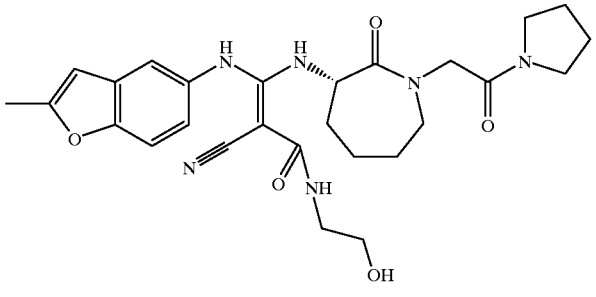 | HPLC (method A) $t_R$ 3.69 min; LRMS (ESI, pos. ion spectrum) m/z 523 (M + H) |
| 125 | 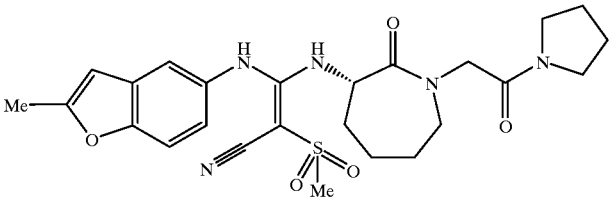 | HPLC (method A) $t_R$ 3.37 min; LRMS (ESI, pos. ion spectrum) m/z 514 (M + H) |

-continued

| Ex. | structure | characterization |
|---|---|---|
| 126 | 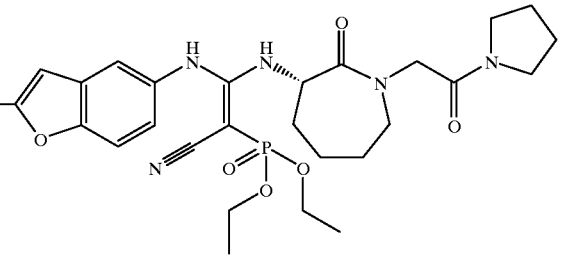 | HPLC (method A) $t_R$ 3.78 min; LRMS (ESI, pos. ion spectrum) m/z 572 (M + H) |
| 127 | 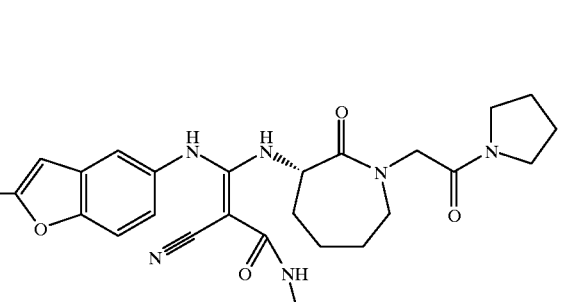 | HPLC (method A) $t_R$ 3.83 min; LRMS (ESI, pos. ion spectrum) m/z 551 (M + H) |

EXAMPLE 128

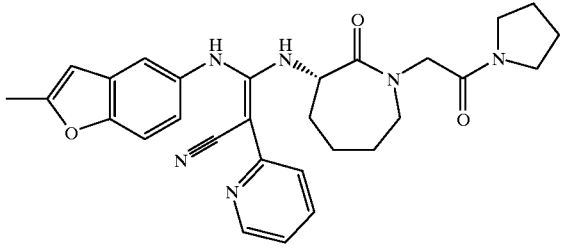

Preparation of the title compound. A solution of 2-methyl-5-benzofuranamine (45.9 mg, 0.312 mmol) and (α-[bis(methylthio)methylene]-2-pyridineacetonitrile (46.4 mg, 0.209 mmol) in EtOH (1.0 mL) was heated at 80° C. for 6 hrs. The reaction mixture was cooled to room temperature, and 1-[[(3S) -3-aminohexahydro-2-oxo-1H-azepin-1-yl]acetyl]pyrrolidine (74.5 mg, 0.312 mmol) was added followed by the addition of mercury (II) acetate (99.2 mg, 0.312 mmol). The mixture was stirred at room temperature for 30 minutes. The reaction mixture was filtered and the crude product was purified by flash chromatography (silica, 10% methanol/ethyl acetate) to give a white solid (47.9 mg, 30%): HPLC (method A) $t_R$ 3.06 min; LRMS (ESI, pos. ion spectrum) m/z 513 (M+H).

EXAMPLES 129–133

Using the procedure described in example 128, the following compounds were prepared. The bismethylthio intermediates were prepared as described in Example 138.

| Ex. | structure | characterization |
|---|---|---|
| 129 | 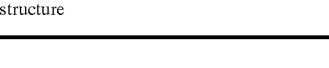 | HPLC (method A) $t_R$ 3.7 min; LRMS (ESI, pos. ion spectrum) m/z 493 (M + H) |

-continued

| Ex. | structure | characterization |
|---|---|---|
| 130 | 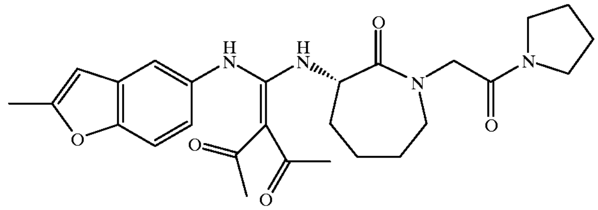 | HPLC (method A) $t_R$ 3.19 min; LRMS (ESI, pos. ion spectrum) m/z 495 (M + H) |
| 131 | 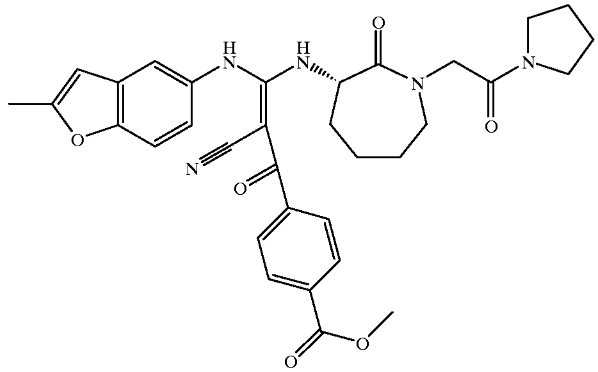 | HPLC (method A) $t_R$ 4.1 min; LRMS (ESI, pos. ion spectrum) m/z 598 (M + H) |
| 132 | 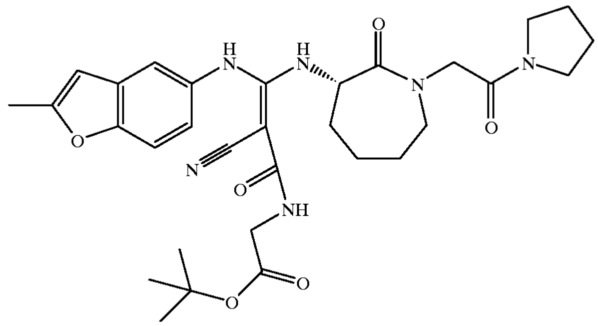 | HPLC (method A) $t_R$ 4.8 min; LRMS (ESI, pos. ion spectrum) m/z 593 (M + H) |
| 133 | 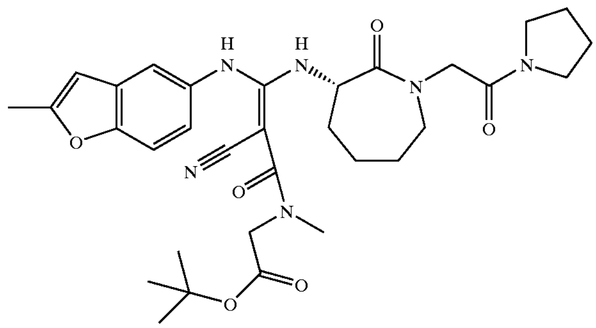 | HPLC (method A) $t_R$ 4.17 min; LRMS (ESI, pos. ion spectrum) m/z 607 (M + H) |

EXAMPLE 134

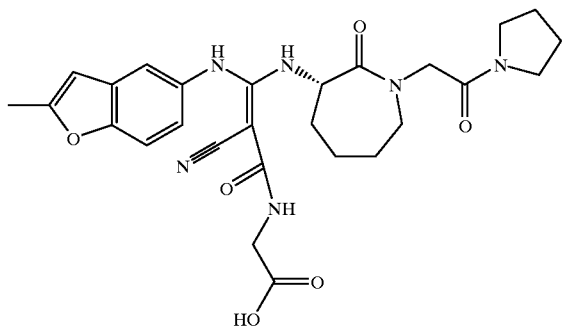

Preparation of the title compound. To a stirring solution of Example 132 compound (0.0245 g, 0.041 mol) in dichloromethane (3 mL) was added TFA (0.064 mL, 0.82 mmol). The reaction was stirred at room temperature for 18 hrs. The solvent was evaporated and toluene was added. The mixture was again concentrated in vacuo. The residue was purified by preparative HPLC to give title compound (0.018 g, 82%): HPLC (method A) $t_R$ 3.61 min; LRMS (ESI, ps. ion spectrum) m/z 537 (M+H).

EXAMPLES 135–137

Using the procedure described in example 134, the following compounds were prepared. Example 135 was prepared from the compound of Example 133. Examples 136 and 137 were obtained from compound of Example 148.

| Ex. | structure | characterization |
|---|---|---|
| 135 | 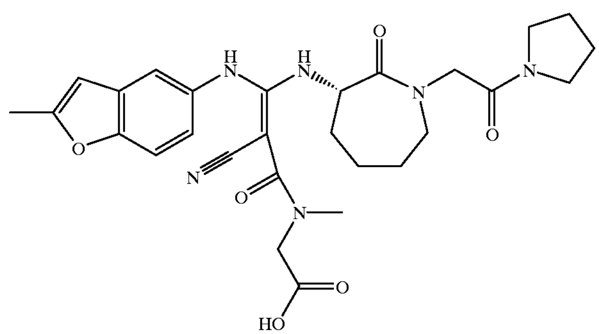 | HPLC (method A) $t_R$ 3.6 min; LRMS (ESI, pos. ion spectrum) m/z 551 (M + H) |
| 136 | 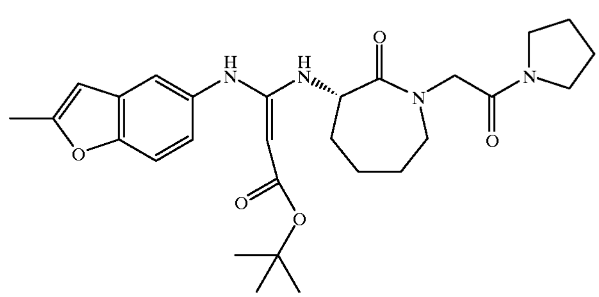 | HPLC (method A) $t_R$ 3.47 min; LRMS (ESI, pos. ion spectrum) m/z 511 (M + H) |
| 137 | 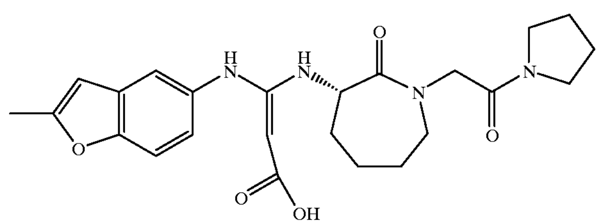 | HPLC (method A) $t_R$ 2.88 min; LRMS (ESI, pos. ion spectrum) m/z 455 (M + H) |

EXAMPLE 138

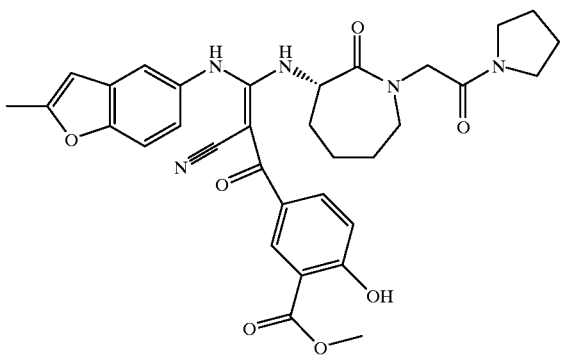

A. Preparation of methyl 5-(cyanoacetyl)-2-hydroxybenzoate. To a stirring solution of methyl 5-acetyl-2-hydroxybenzoate (2.0 g, 0.010 mol) in dichloromethane (10 mL) was slowly added bromine (0.53 mL, 0.010 mol). The reaction was stirred at room temperature for 6 hrs. The solvent was evaporated and 0.5 M LiCN (20 mL, 0.01 mol) in DMF was added. The reaction mixture was stirred at room temperature for 3 h. The solvent was removed and the residue was chromatograped (silica) to give methyl 5-(cyanoacetyl)-2-hydroxybenzoate (0.66 g, 30%): HPLC (method A) $t_R$ 2.70 min; LRMS (ESI, pos. ion spectrum) m/z 220 (M+H).

B. Preparation of methyl 5-(3,3-bis(methylthio)-1-oxo-2-cyano-2-propenyl)-2-hydroxybenzoate. To a mixture of methyl 5-(cyanoacetyl)-2-hydroxybenzoate (0.300 g, 1.37 mmol) and carbon disulfide (0.101 g, 1.37 mmol) in EtOH at 0° C. was slowly added NaOH (0.109 g, 2.74 mmol) in water. After the addition, the reaction mixture was warmed to room temperature and stirred for 1 hr. To the mixture was slowly added dimethyl sulfate (0.345 g, 2.74 mmol). The precipitate was collected by filtration, washed with water and dried to afford the part B compound (0.10 g, 21%): HPLC (method A) $t_R$ 3.43 min; LRMS (ESI, pos. ion spectrum) m/z 324 (M+H).

C. Preparation of the title compound. The title compound was prepared from part B compound using the procedure in Example 128: HPLC (method A) $t_R$ 4.3 min; LRMS (ESI, pos. ion spectrum) 614 (M+H)

EXAMPLES 139–140

Using the procedure described in example 138, the following examples were prepared.

| Ex. | structure | characterization |
|---|---|---|
| 139 | 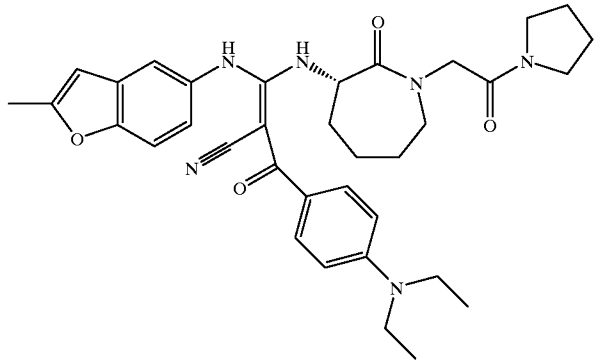 | HPLC (method A) $t_R$ 3.75 min; LRMS (ESI, pos. ion spectrum) m/z 611 (M + H) |
| 140 | 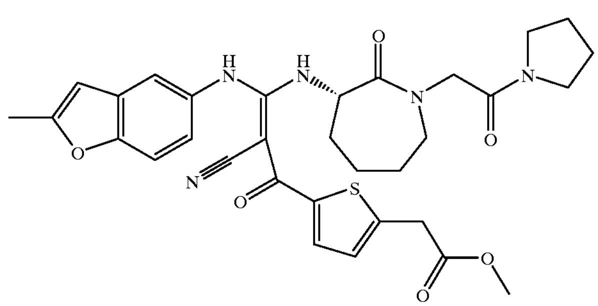 | HPLC (method A) $t_R$ 4.13 min; LRMS (ESI, pos. ion spectrum) m/z 618 (M + H) |

EXAMPLE 141

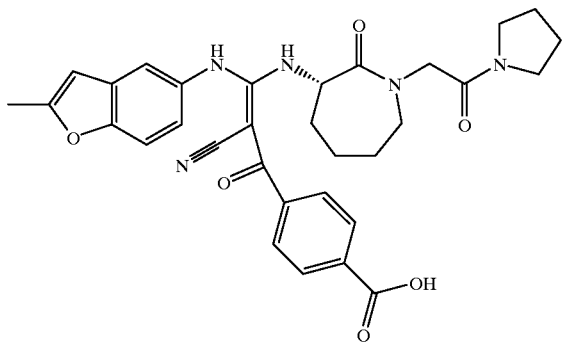

Preparation of the title compound. To a solution of Example 131 compound (0.012 g, 0.02 mmol) in THF/methanol (1/1, 2 mL) at 0° C. was slowly added LiOH (0.008 g, 0.2 mmol) in water (0.2 mL). After the addition, the reaction mixture was stirred at room temperature for 18 h. The reaction mixture was extracted three times with dichloromethane. The pH of the aqueous layer was brought to 3–4 with HCl. The aqueous layer was extracted with dichloromethane three times. The combined organic layers were dried with magnesium sulfate and concentrated in vacuo to afford the title compound (0.011 g, 95%): HPLC (method A) $t_R$ 3.92 min; LRMS (EST, pos. ion spectrum) m/z 584 (M+H).

EXAMPLES 142–145

Using the procedure described in example 141, the following examples were prepared.

| Ex. | structure | characterization |
|---|---|---|
| 142 | 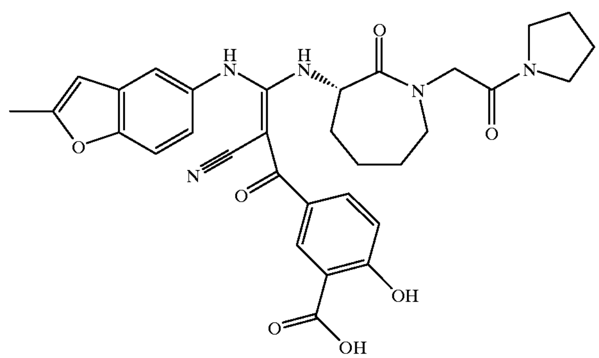 | HPLC (method A) $t_R$ 4.02 min; LRMS (ESI, pos. ion spectrum) m/z 600 (M + H) |
| 143 | 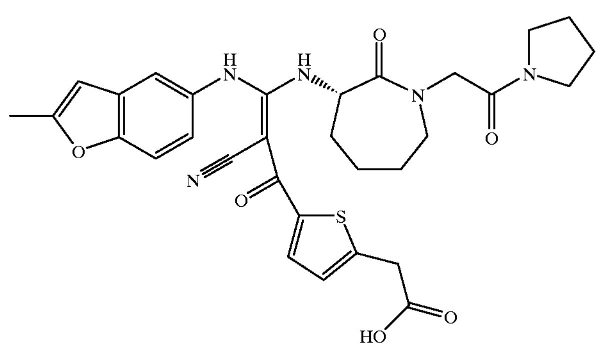 | HPLC (method A) $t_R$ 3.96 min; LRMS (ESI, pos. ion spectrum) m/z 604 (M + H) |
| 144 | 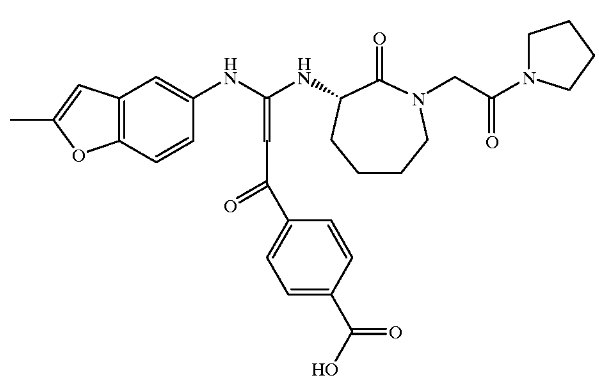 | HPLC (method A) $t_R$ 3.34 min; LRMS (ESI, pos. ion spectrum) m/z 559 (M + H) |

-continued

| Ex. | structure | characterization |
|---|---|---|
| 145 | 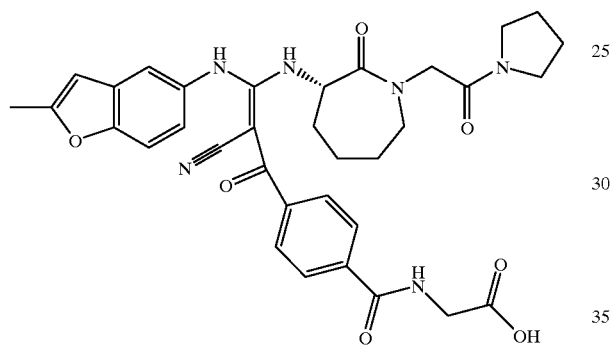 | HPLC (method A) $t_R$ 3.71 min; LRMS (ESI, pos. ion spectrum) m/z 604 (M + H) |

EXAMPLE 146

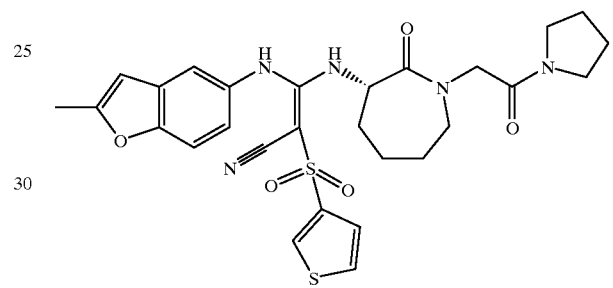

A. Preparation of [4-[2-Cyano-3-[[(3S)-hexahydro-2-oxo-1-[2-oxo-2-(1-pyrrolidinyl)ethyl]-1H-azepin-3-yl]amino]-3-[(2-methyl-5-benzofuranyl)amino]-1-oxo-2-propenyl]benzoyl]glycine, 1,1-dimethylethyl ester. To the compound of Example 142 (4.5 mg, 0.0077 mmol) in dichloromethane (2 mL) was added glycine t-butyl ester (5.2 mg, 0.0309 mmol), WSC (5.93 mg, 0.0309 mmol), and DMAP (cat.) in that order. The resulting solution was stirred at room temperature overnight. Water was added to the reaction and the mixture was extracted with ethyl acetate three times. The combined organic fractions were washed once with brine, dried over magnesium sulfate and evaporated. The residue was purified by flash chromatography (silica, 5 % methanol/ethyl acetate) to gave [4-[2-cyano-3-[[(3S)-hexahydro-2-oxo-1-[2-oxo-2-(1-pyrrolidinyl)ethyl]-1H-azepin-3-yl]amino]-3-[(2-methyl-5-benzofuranyl)amino]-1-oxo-2-propenyl]benzoyl]glycine, 1,1-dimethylethyl ester (5.0 mg, yield: 94 %): HPLC (method A): $t_R$ 4.1 min. LRMS (ESI, pos. ion spectrum) m/z 697 (M+H).

B. Preparation of [4-[2-cyano-3-[[(3S)-hexahydro-2-oxo-1-[2-oxo-2-(1-pyrrolidinyl)ethyl]-1H-azepin-3-yl]amino]-3-[(2-methyl-5-benzofuranyl)amino]-1-oxo-2-propenyl]benzoyl]glycine. The title compound was prepared from [4-[2-cyano-3-[[(3S)-hexahydro-2-oxo-1-[2-oxo-2-(1-pyrrolidinyl)ethyl]-1H-azepin-3-yl]amino]-3-[(2-methyl-5-benzofuranyl)amino]-1-oxo-2-propenyl]benzoyl]glycine, 1,1-dimethylethyl ester using the procedure in Example 134: HPLC (method A) $t_R$ 3.7; LRMS (ESI, pos. ion spectrum) 641.

EXAMPLE 147

Preparation of 1-[[(3S)-3-[[2-[(3-thienyl)sulfonyl]-2-cyano-1-[(2-methyl-5-benzofuranyl)anino]-1-ethenyl]amino]hexahydro-2-oxo-1H-azepin-1-yl]acetyl]pyrrolidine. To a solution of (3-thienylsulphonyl)acetonitrile (59.4 mg, 0.318 mmol) in DMF (1 mL) was added NaH (95%, 8.08 mg, 0.344 mmol). After stirring 5 min at room temperature, 5-isothiocyanato-2-methylbenzofuran (50 mg, 0.265 mmol) was added in one portion. The reaction was heated at 50° C. for 30 min. To the mixture was added 1-[[(3S)-3-aminohexahydro-2-oxo-1H-azepin-1-yl]acetyl]pyrrolidine (76.0 mg, 0.318 =mol), WSC (101.7 mg, 0.53 mmol) and N,N-dimethyl 4-pyridinamine (cat.) in that order. The reaction mixture was stirred at room temperature overnight. Water was added to the reaction and the mixture was extracted with ethyl acetate three times. The combined organic fractions were washed once with brine, dried over magnesium sulfate and evaporated. The residue was chromatographed (silica, 5% methanol/ethyl acetate) to provide 1-[[(3S)-3-[[2-[(3-thienyl)sulfonyl]-2-cyano-1-[(2-methyl-5-benzofuranyl)amino]-1-ethenyl]amino]hexahydro-2-oxo-1H-azepin-1-yl]acetyl]pyrrolidine (63.0 mg, 41%): HPLC (method A) $t_R$ 3.65 min; LRMS (ESI, pos. ion spectrum) m/z 582 (M+H).

EXAMPLES 148–192

A. Preparation of 7-nitro-3-chloro-1H-indole. To a mixture of 7-nitro-1H-indole (2.0 g, 12.3 mmol) in THF (10 mL) and 0.1 N HCl (0.16 mL, 16 mmol) was added 2-chloro-1H-isoindole-1,3(2H)-dione (1.68 g, 12.5 mmol) in one ortion. The reaction was stirred at room temperature for 5 h. Water (53 mL) was added. The resulting precipitate were collected by filtration; washed successively with water, methanol/water (1:1), and isopropyl ether; and was dried to afford the title compound 7-nitro-3-chloro-1H-indole. (1.3 g, 54%)

B. Preparation of 3-chloro-1H-indole-7-amine. 3-chloro-1H-indole-7-amine was prepared from 7-nitro-3-chloro-1H-indole using the procedure described in Example 36, part A.

C. Preparation of 3-chloro-7-isothiocyanato-1H-indole. Using the procedure described in Example 80 part A, 3-chloro-7-isothiocyanato-1H-indole was prepared.

D. Preparation of 7-nitro-1H-indole-3-carboxaldehyde. To DMF (15 mL) at 10–20° C. was added phosphorous oxychloride (5 mL). To the mixture was added, in one portion, a solution of 7-nitro-1H-indole (5.0 g, 30.7 mmol) in DMF (10 mL). The reaction mixture was stirred at 45° C. for 1.5 h and was then poured into ice. To the stirring reaction mixture was added NaOH (4.75 g, 118 mmol) in water (30 mL). The mixture was heated to boiling for 3 min. The resulting solid was collected by filtration, washed with water and dried to give 7-nitro-1H-indole-3-carboxaldehyde.

E. Preparation of 7-amino-1H-indole-3-carboxamide. To a mixture of 7-nitro-1H-indole-3-carboxaldehyde (1.01 g, 5.41 mmol) in EtOH (15 mL) and NaOH at 0° C. was added 30% $H_2O_2$. The reaction was warmed to 15° C. for 2 hrs. Then the reaction mixture was stirred at room temperature overnight. Water (50 mL) was added and the mixture was filtered. The filtrate was concentrated in vacuo to remove ethanol. The residue was extracted twice with ethyl acetate. The combined organic layers were dried with magnesium sulfate and concentrated in vacuo. The resulting yellow solid was dissolved in methanol/THF (1/1, 100 mL). The mixture was stirred under a hydrogen balloon with palladium on carbon for 8 hrs. The reaction was filtered and the filtrate was concentrated in vacuo to provide 7-amino-1H-indole-3-carboxamide.

F. Preparation of 3-methyl-1H-indol-7-amine. To a solution of 7-nitro-1H-indole-3-carboxaldehyde (2.0 g, 11.2 mmol) in 2-propanol (160 mL) was added $NaBH_4$ (4.06 g, 107 mmol) and Pd/C. The reaction mixture was refluxed for 6 hrs. Water (15 mL) was added and the reaction was filtered. The filtrate was extracted with ethyl acetate. The organic layer was dried and the solvent was removed to give 3-methyl-1H-indol-7-amine.

Using the procedure described in Example 147, the following compounds were prepared.

| Ex. | structure | characterization |
|---|---|---|
| 148 | 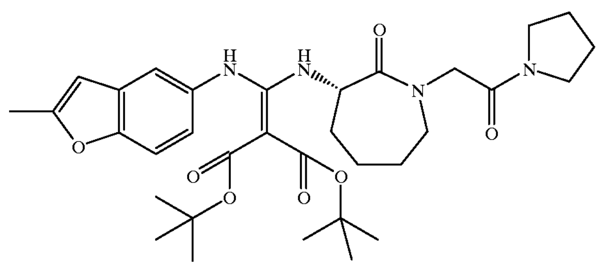 | HPLC (method A) $t_R$ 3.89 min; LRMS (ESI, pos. ion spectrum) m/z 611 (M + H) |
| 149 | 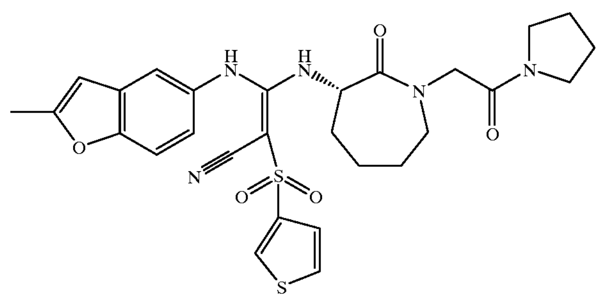 | HPLC (method A) $t_R$ 3.65 min; LRMS (ESI, pos. ion spectrum) m/z 582 (M + H) |
| 150 | 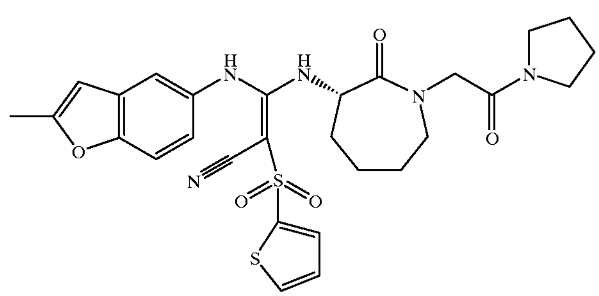 | HPLC (method A) $t_R$ 3.66 min; LRMS (ESI, pos. ion spectrum) m/z 582 (M + H) |

-continued
| Ex. | structure | characterization |
|---|---|---|
| 151 | 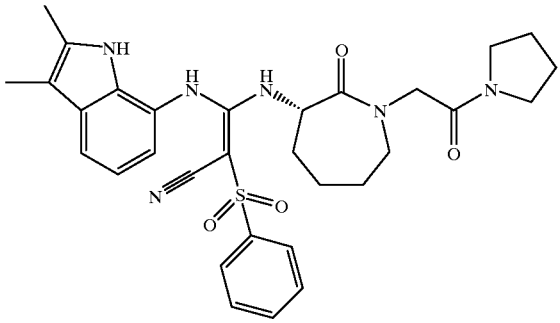 | HPLC (method A) $t_R$ 3.66 min; LRMS (ESI, pos. ion spectrum) m/z 589 (M + H) |
| 152 | 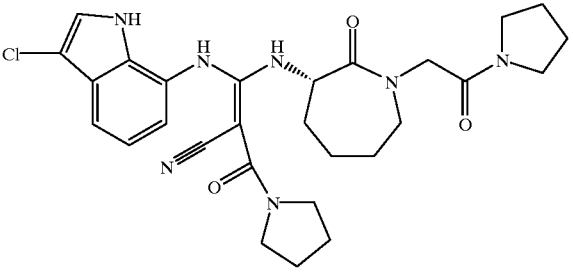 | HPLC (method A) $t_R$ 3.73 min; LRMS (ESI, pos. ion spectrum) m/z 552/554 (M + H) |
| 153 | 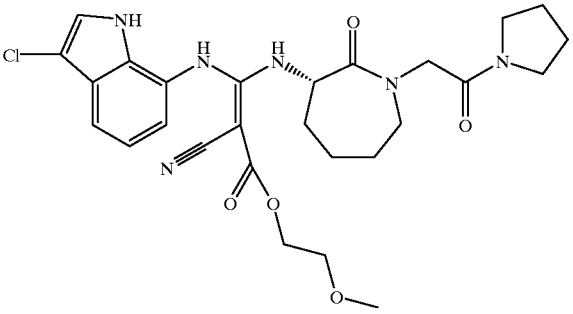 | HPLC (method A) $t_R$ 3.65 min; LRMS (ESI, pos. ion spectrum) m/z 557/559 (M + H) |
| 154 | 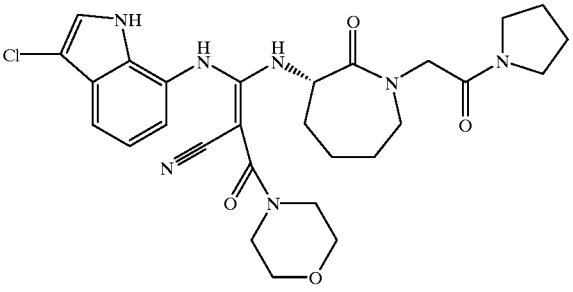 | HPLC (method A) $t_R$ 3.07 min; LRMS (ESI, pos. ion spectrum) m/z 568/570 (M + H) |
| 155 | 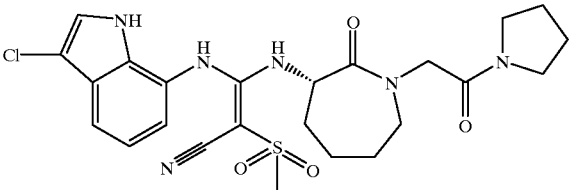 | HPLC (method A) $t_R$ 3.31 min; LRMS (ESI, pos. ion spectrum) m/z 533/535 (M + H) |

| Ex. | structure | characterization |
|---|---|---|
| 156 | 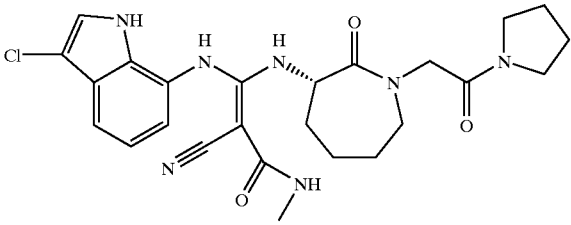 | HPLC (method A) $t_R$ 3.25 min; LRMS (ESI, pos. ion spectrum) m/z 512/514 (M + H) |
| 157 | 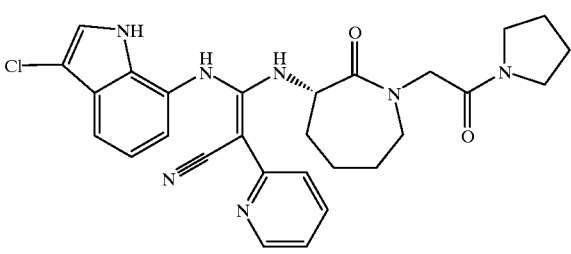 | HPLC (method A) $t_R$ 3.56 min; LRMS (ESI, pos. ion spectrum) m/z 532/534 (M + H) |
| 158 | 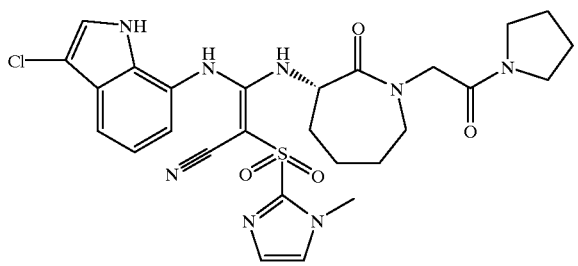 | HPLC (method A) $t_R$ 3.54 min; LRMS (ESI, pos. ion spectrum) m/z 599/601 (M + H) |
| 159 | 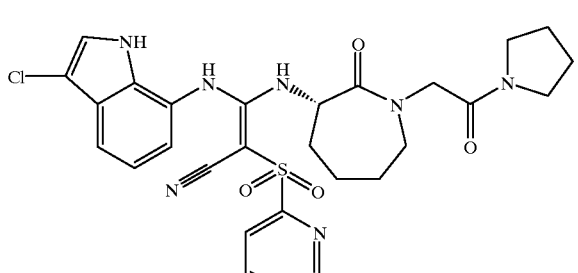 | HPLC (method A) $t_R$ 3.1 min; LRMS (ESI, pos. ion spectrum) m/z 596/598 (M + H) |
| 160 | 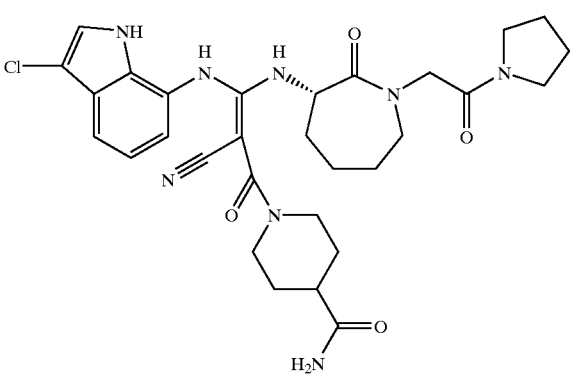 | HPLC (method A) $t_R$ 3.4 min; LRMS (ESI, pos. ion spectrum) m/z 609/611 (M + H) |

-continued

| Ex. | structure | characterization |
|---|---|---|
| 161 | 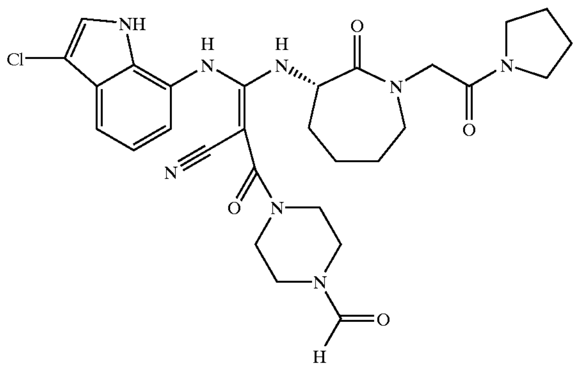 | HPLC (method A) $t_R$ 3.37 min; LRMS (ESI, pos. ion spectrum) m/z 595/597 (M + H) |
| 162 | 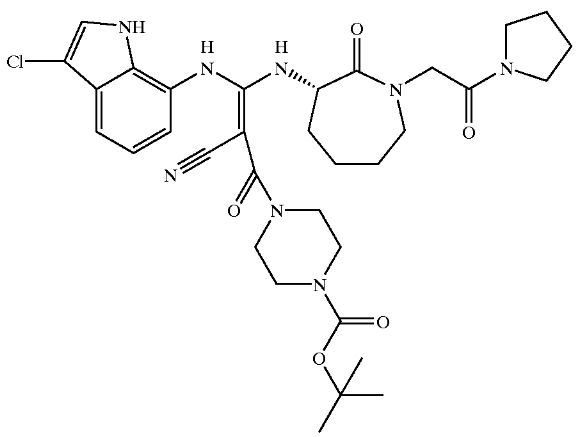 | HPLC (method A) $t_R$ 3.95 min; LRMS (ESI, pos. ion spectrum) m/z 667/669 (M + H) |
| 163 | 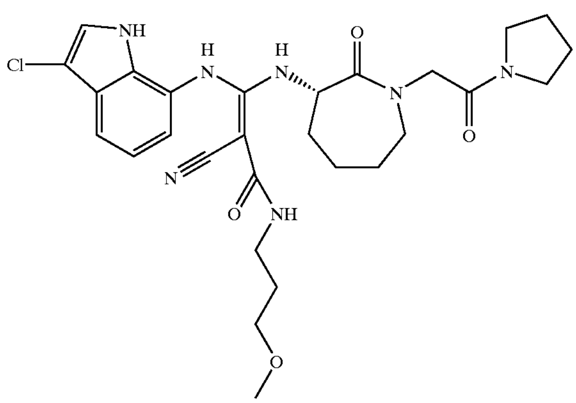 | HPLC (method A) $t_R$ 3.70 min; LRMS (ESI, pos. ion spectrum) m/z 570/572 (M + H) |
| 164 | 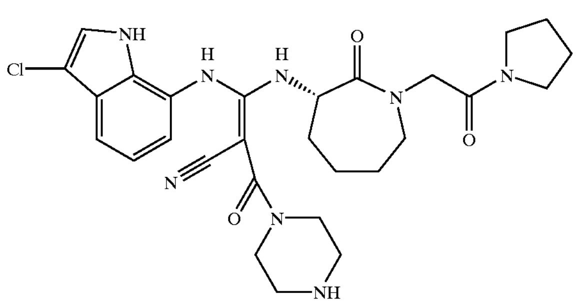 | HPLC (method A) $t_R$ 3.00 min; LRMS (ESI, pos. ion spectrum) m/z 567/569 (M + H) |

-continued

| Ex. | structure | characterization |
|---|---|---|
| 165 | 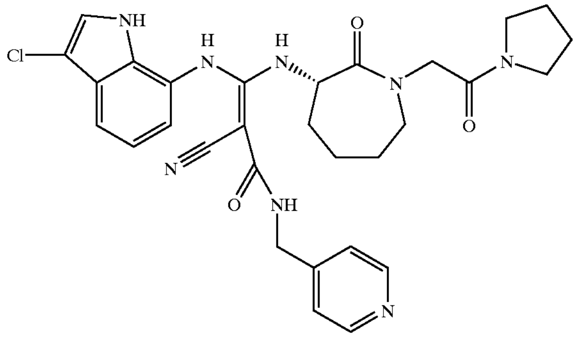 | HPLC (method A) $t_R$ 3.11 min; LRMS (ESI, pos. ion spectrum) m/z 589/591 (M + H) |
| 166 | 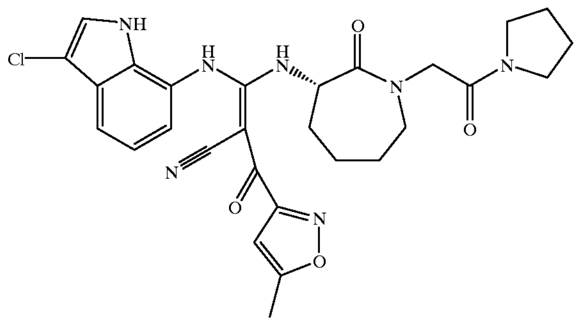 | HPLC (method A) $t_R$ 3.59 min; LRMS (ESI, pos. ion spectrum) m/z 564/566 (M + H) |
| 167 | 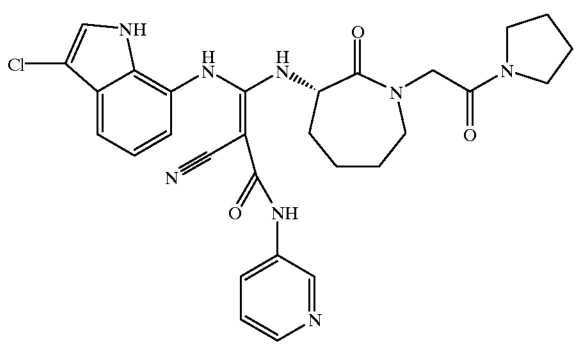 | HPLC (method A) $t_R$ 3.17 min; LRMS (ESI, pos. ion spectrum) m/z 575/577 (M + H) |
| 168 | 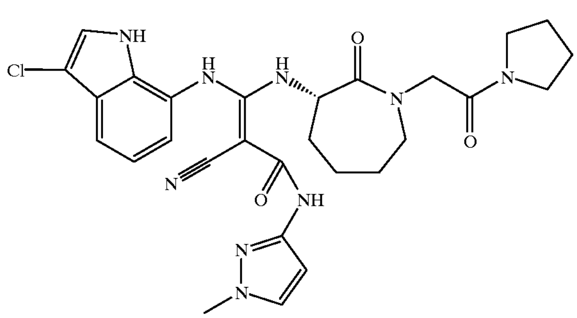 | HPLC (method A) $t_R$ 3.62 min; LRMS (ESI, pos. ion spectrum) m/z 578/580 (M + H) |

-continued
| Ex. | structure | characterization |
|---|---|---|
| 169 | 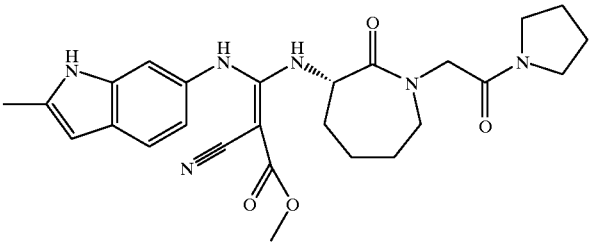 | HPLC (method A) $t_R$ 3.50 min; LRMS (ESI, pos. ion spectrum) m/z 493 (M + H) |
| 170 | 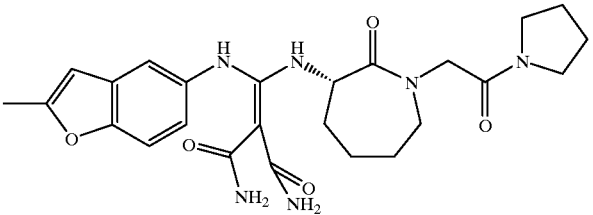 | HPLC (method A) $t_R$ 2.5 min; LRMS (ESI, pos. ion spectrum) m/z 497 (M + H) |
| 171 | 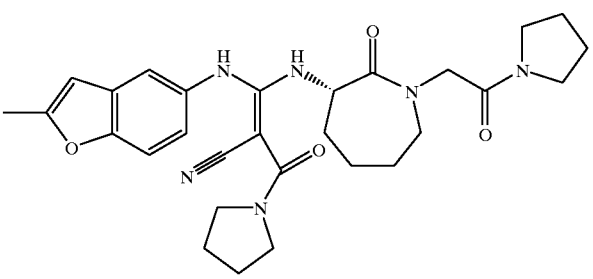 | HPLC (method A) $t_R$ 3.95 min; LRMS (ESI, pos. ion spectrum) m/z 533 (M + H) |
| 172 | 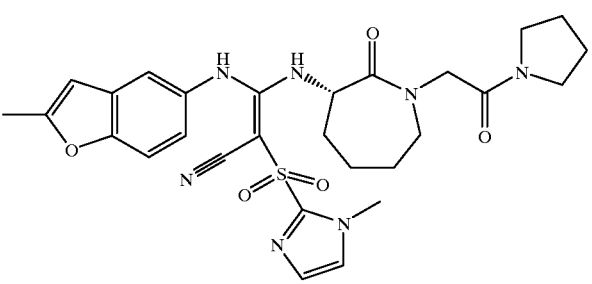 | HPLC (method A) $t_R$ 3.44 min; LRMS (ESI, pos. ion spectrum) m/z 580 (M + H) |
| 173 | 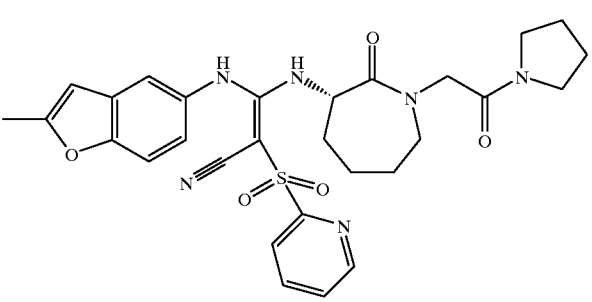 | HPLC (method A) $t_R$ 3.56 min; LRMS (ESI, pos. ion spectrum) m/z 577 (M + H) |

-continued

| Ex. | structure | characterization |
|---|---|---|
| 174 | 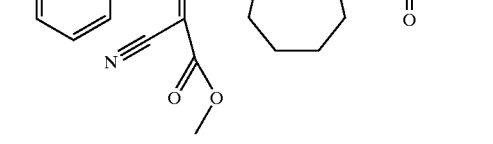 | HPLC (method A) $t_R$ 3.12 min; LRMS (ESI, pos. ion spectrum) m/z 494 (M + H) |
| 175 | 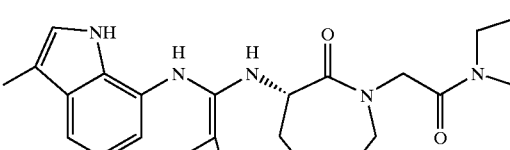 | HPLC (method A) $t_R$ 3.65 min; LRMS (ESI, pos. ion spectrum) m/z 513/515 (M + H) |
| 176 | 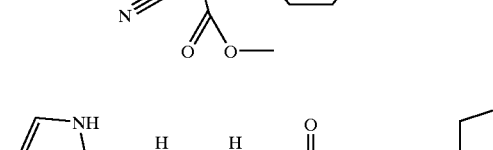 | HPLC (method A) $t_R$ 3.41 min; LRMS (ESI, pos. ion spectrum) m/z 498/500 (M + H) |
| 177 | 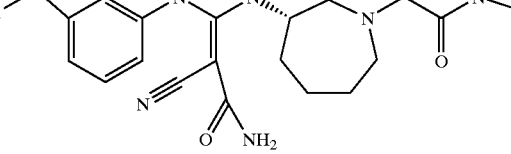 | HPLC (method A) $t_R$ 3.27 min; LRMS (ESI, pos. ion spectrum) m/z 480/482 (M + H) |
| 178 | 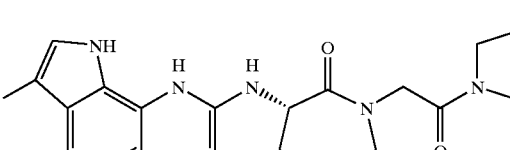 | HPLC (method A) $t_R$ 3.69 min; LRMS (ESI, pos. ion spectrum) m/z 549/551 (M + H) |
| 179 | 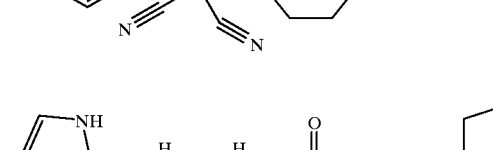 | HPLC (method A) $t_R$ 3.52 min; LRMS (ESI, pos. ion spectrum) m/z 526/528 (M + H) |

-continued

| Ex. | structure | characterization |
|---|---|---|
| 180 | 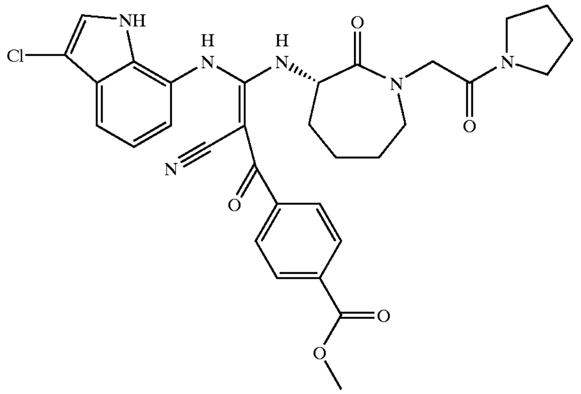 | HPLC (method A) $t_R$ 3.65 min; LRMS (ESI, pos. ion spectrum) m/z 617/619 (M + H) |
| 181 | 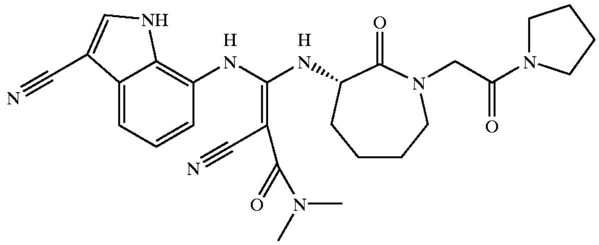 | HPLC (method A) $t_R$ 3.05 min; LRMS (ESI, pos. ion spectrum) m/z 517 (M + H) |
| 182 | 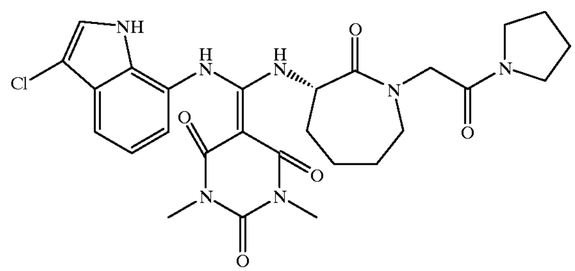 | HPLC (method A) $t_R$ 3.97 min; LRMS (ESI, pos. ion spectrum) m/z 570/572 (M + H) |
| 183 | 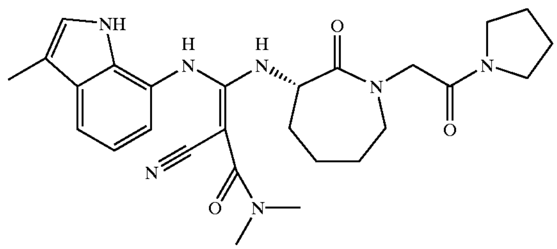 | HPLC (method A) $t_R$ 3.42 min; LRMS (ESI, pos. ion spectrum) m/z 506 (M + H) |
| 184 | 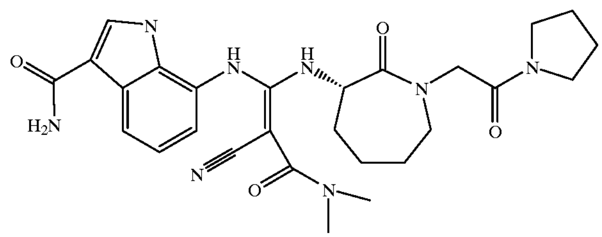 | HPLC (method A) $t_R$ 2.64 min; LRMS (ESI, pos. ion spectrum) m/z 535 (M + H) |

-continued

| Ex. | structure | characterization |
|---|---|---|
| 185 | 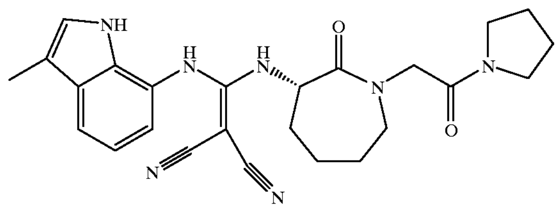 | HPLC (method A) $t_R$ 3.23 min; LRMS (ESI, pos. ion spectrum) m/z 460 (M + H) |
| 186 | 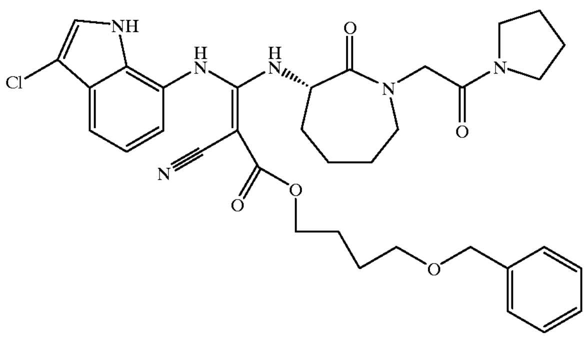 | HPLC (method A) $t_R$ 4.25 min; LRMS (ESI, pos. ion spectrum) m/z 661/663 (M + H) |
| 187 | 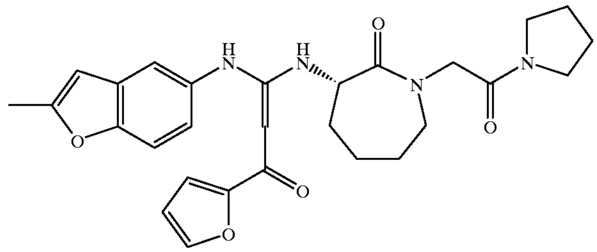 | HPLC (method PS1) $t_R$ 3.1 min; LRMS (ESI, pos. ion spectrum) m/z 505 (M + H) |
| 188 | 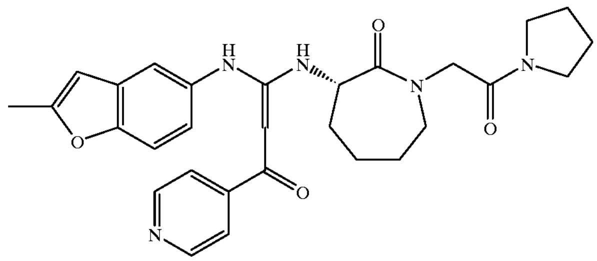 | HPLC (method A) $t_R$ 3.29 min; LRMS (ESI, pos. ion spectrum) m/z 516 (M + H) |
| 189 | 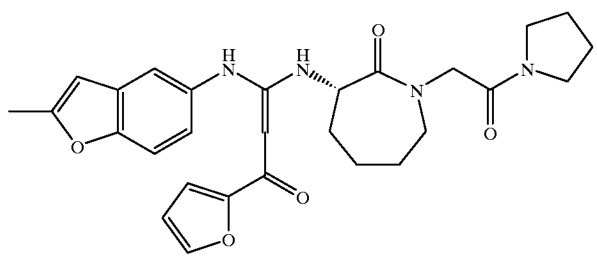 | HPLC (method A) $t_R$ 3.13 min; LRMS (ESI, pos. ion spectrum) m/z 505 (M + H) |

| Ex. | structure | characterization |
|---|---|---|
| 190 | 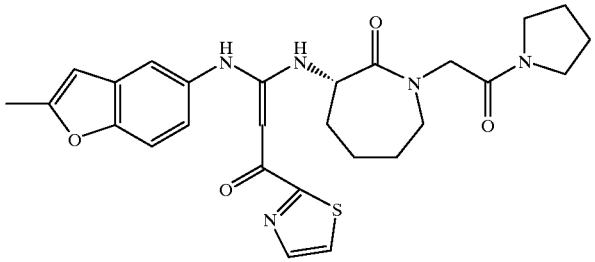 | HPLC (method A) $t_R$ 3.67 min; LRMS (ESI, pos. ion spectrum) m/z 522 (M + H) |
| 191 | 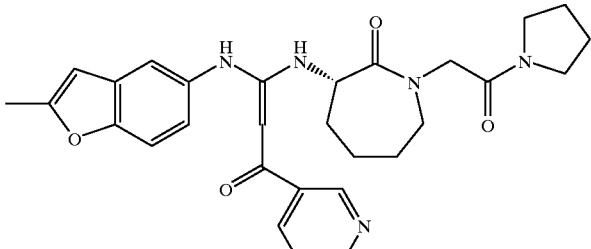 | HPLC (method A) $t_R$ 3.23 min; LRMS (ESI, pos. ion spectrum) m/z 516 (M + H) |
| 192 | 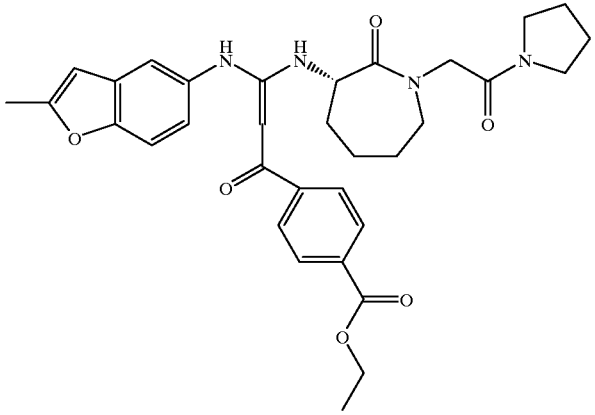 | HPLC (method A) $t_R$ 3.77 min; LRMS (ESI, pos. ion spectrum) m/z 587 (M + H) |

EXAMPLES 193–194

Using the procedure described in example 3 the following examples were prepared.

| Ex. | structure | characterization |
|---|---|---|
| 193 | 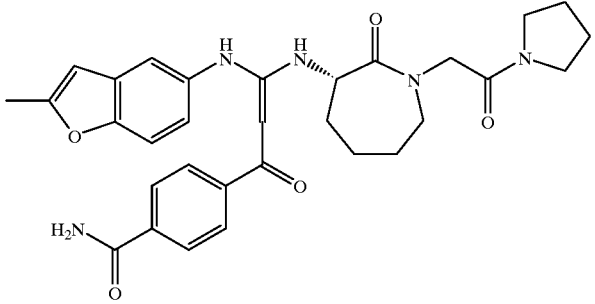 | HPLC (method A) $t_R$ 3.06 min; LRMS (ESI, pos. ion spectrum 558 (M + H) |

| Ex. | structure | characterization |
|---|---|---|
| 194 | 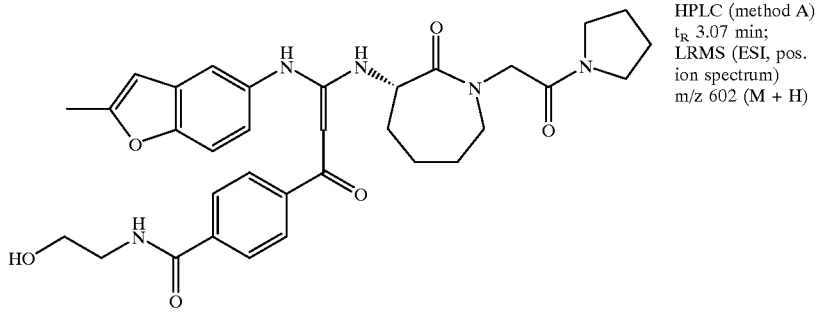 | HPLC (method A) $t_R$ 3.07 min; LRMS (ESI, pos. ion spectrum) m/z 602 (M + H) |

EXAMPLES 195–198

Using the procedure described in Example 20 the following examples were prepared.

| Ex. | structure | characterization |
|---|---|---|
| 195 | 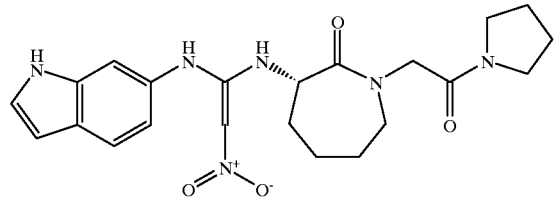 | HPLC (method A) $t_R$ 2.85 min; LRMS (ESI, pos. ion spectrum) m/z 441 (M + H) |
| 196 | 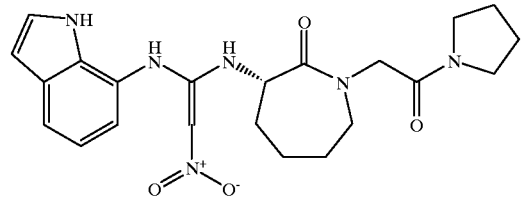 | HPLC (method A) $t_R$ 3.15 min; LRMS (ESI, pos. ion spectrum) m/z 441 (M + H) |
| 197 | 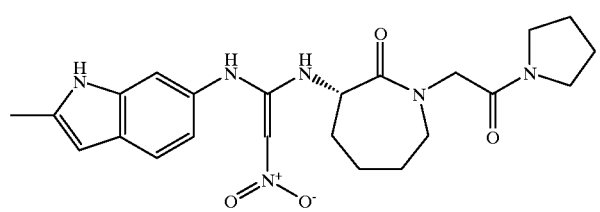 | HPLC (method A) $t_R$ 3.33 min; LRMS (ESI, pos. ion spectrum) m/z 455 (M + H) |
| 198 | 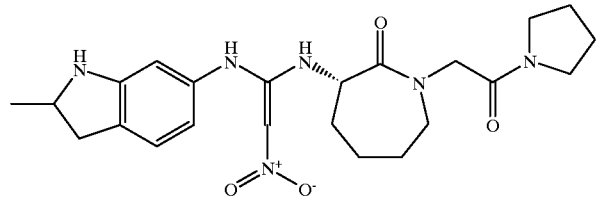 | HPLC (method A) $t_R$ 2.20 min; LRMS (ESI, pos. ion spectrum) m/z 457 (M + H) |

EXAMPLES 199–201

Using the procedure described in Example 21 the following compounds were prepared.

parative HPLC. Product-containing fractions were combined and concentrated to provide the title compound (46 mg, 53% yield): HPLC (method A) $t_R$ 3.61 min; LRMS (ESI, pos. ion spectrum) m/z 571/573 (M+H).

| Ex. | structure | characterization |
|---|---|---|
| 199 | 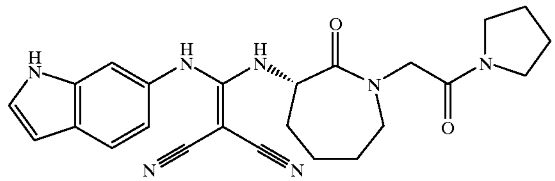 | HPLC (method A) $t_R$ 3.0 min; LRMS (ESI, pos. ion spectrum) m/z 446 (M + H) |
| 200 | 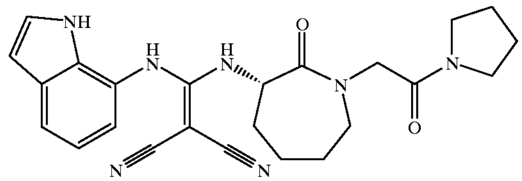 | HPLC (method A) $t_R$ 3.3 min; LRMS (ESI, pos. ion spectrum) m/z 446 (M + H) |
| 201 | 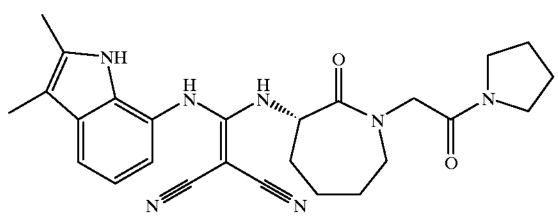 | HPLC (method A) $t_R$ 3.4 min; LRMS (ESI, pos. ion spectrum) m/z 474 (M + H) |

EXAMPLE 202

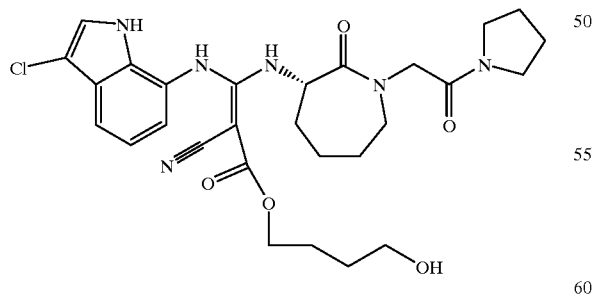

Preparation of title compound. The compound of Example 186 (100 mg, 0.15 mmol) and palladium on active carbon (10% Pd. 0.3 g) in methanol (10 mL) were stirred at room temperature under a hydrogen-filled balloon for 3 h. The mixture was filtered through a pad of CELITE and the filtrate was concentrated. The residue was purified by pre-

EXAMPLE 203

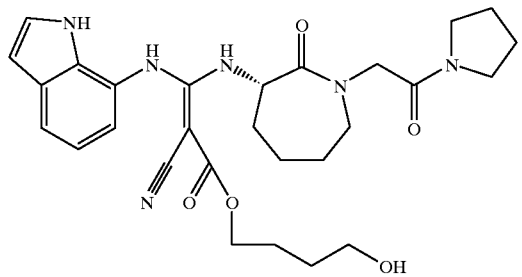

Preparation of the title compound. The title compound was obtained by combining and concentrating the product-containing fractions produced during the purification of Example 202: 32 mg, 39% yield; HPLC (method A) $t_R$ 3.39 min, LRMS (ESI, pos. ion spectrum) m/z 537 (M+H).

We claim:
1. A compound of formula I

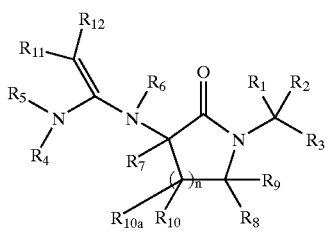

or pharmaceutically acceptable salts, or stereoisomers thereof, wherein n is 3;

$R_1$, $R_2$ and $R_3$ are the same or different and are independently selected from hydrogen, alkyl, alkenyl, alkynyl, aryl, heteroaryl, arylalkyl, arylalkenyl, arylalkynyl, alkoxy, cyano, nitro, heteroarylalkyl, cycloalkyl, cycloalkylalkyl, polycycloalkyl, polycycloalkylalkyl, cycloalkenyl, cycloalkynyl, alkylcarbonyl, arylcarbonyl, heterocyclo, heterocycloalkyl, cycloalkenylalkyl, polycycloalkenyl, polycycloalkenylalkyl, polycycloalkynyl, polycycloalkynylalkyl,

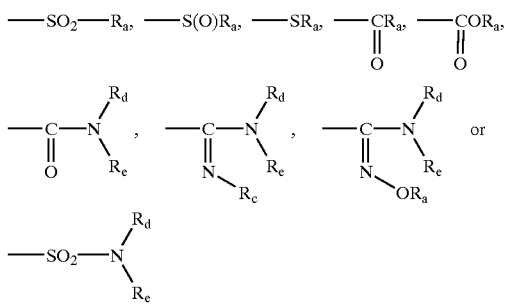

any of which may be optionally substituted through available atoms with 1, 2, 3, 4 or 5 groups selected from $Z_1$, $Z_2$, $Z_3$, $Z_4$, and $Z_5$;

or $R_1$, $R_2$ and $R_3$ can in pairs of two join together to form a saturated carbocylic or heterocylic ring optionally substituted through available atoms with 1, 2, 3, 4 or 5 groups selected from $Z_1$, $Z_2$, $Z_3$, $Z_4$, and $Z_5$;

or $R_1$ and $R_2$ can join together to form an unsaturated carbocylic or heterocyclic ring optionally substituted through available atoms with 1, 2, 3, 4 or 5 groups selected from $Z_1$, $Z_2$, $Z_3$, $Z_4$, and $Z_5$ wherein $R_3$ is optionally a bond participating in the unsaturation of said ring;

$R_4$, $R_6$, $R_8$, $R_9$, $R_a$, $R_b$, are the same or different and are independently selected from hydrogen, alkyl, alkenyl, alkynyl, aryl, heteroaryl, arylalkyl, arylalkenyl, arylalkynyl, heteroarylalkyl, cycloalkyl, cycloalkylalkyl, polycycloalkyl, polycycloalkylalkyl, cycloalkenyl, cycloalkynyl, alkylcarbonyl, arylcarbonyl, heterocyclo, heterocycloalkyl, cycloalkenylalkyl, polycycloalkenyl, polycycloalkenylalkyl, polycycloalkynyl or polycycloalkynylalkyl, any of which may be optionally substituted through available atoms with 1, 2, 3, 4 or 5 groups selected from $Z_1$, $Z_2$, $Z_3$, $Z_4$, and $Z_5$;

$R_5$ is hydrogen, alkyl, alkenyl, alkynyl, aryl, heteroaryl, alkoxyalkyl, arylalkyl, heteroarylalkyl, arylalkenyl, arylalkynyl, cycloalkyl, cycloalkylalkyl, polycycloalkyl, polycycloalkylalkyl, cycloalkenyl, cycloalkynyl, alkylcarbonyl, aminocarbonyl, substituted aminocarbonyl, arylcarbonyl, heterocyclo, heterocycloalkyl, cycloalkenylalkyl, polycycloalkenyl, polycycloalkenylalkyl, polycycloalkynyl, polycycloalkynyl-alkyl, cyano, nitro, hydroxy, amino, —$OR_a$, —$SR_a$, —$S(O)R_a$,

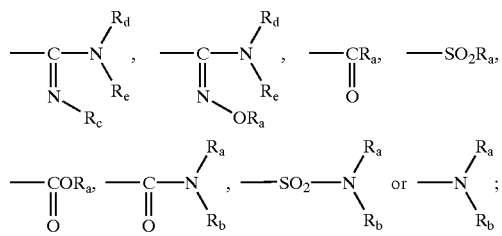

any of which may be optionally substituted through available atoms with 1, 2, 3, 4 or 5 groups selected from $Z_1$, $Z_2$, $Z_3$, $Z_4$, and $Z_5$;

$R_7$ is independently selected from hydrogen, alkyl, alkenyl, alkynyl, aryl, heteroaryl, arylalkyl, arylalkenyl, arylalkynyl, heteroarylalkyl, cycloalkyl, cycloalkylalkyl, polycycloalkyl, polycycloalkylalkyl, cycloalkenyl, cycloalkynyl, alkylcarbonyl, arylcarbonyl, hetreocyclo, heterocycloalkyl, cycloalkenylalkyl, polycycloalkenyl, polycycloalkenylalkyl, polycycloalkynyl, polycycloalkynylalkyl,

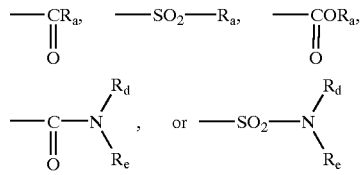

all optionally substituted through available atoms with 1, 2, 3, 4 or 5 groups selected from $Z_1$, $Z_2$, $Z_3$, $Z_4$, and $Z_5$;

$R_{10}$ and $R_{10a}$ are the same or different are independently selected from hydrogen, halogen, alkyl, alkenyl, alkynyl, aryl, heteroaryl, arylalkyl, arylalkenyl, arylalkynyl, heteroarylalkyl, cycloalkyl, cycloalkylalkyl, polycycloalkyl, polycycloalkylalkyl, cycloalkenyl, cycloalkynyl, alkylcarbonyl, arylcarbonyl, heterocyclo, heterocycloalkyl, cycloalkenylalkyl, polycycloalkenyl, polycycloalkenylalkyl, polycycloalkynyl polycycloalkynylalkyl,

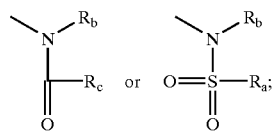

any of which may be optionally substituted through available atoms with 1, 2, 3, 4 or 5 groups selected from $Z_1$, $Z_2$, $Z_3$, $Z_4$, and $Z_5$;

$R_{11}$ and $R_{12}$ are the same or different and are independently selected from hydrogen, alkyl, aryl, cyano, nitro, heteroaryl, sulfonyl, acyl, amido, sufonamido, sulfamoyl, alkoxycarbonyl, carboxy, —C(O)$_z$R$_a$, —S(O)$_z$R$_a$,
—P(O)(OR$_a$)$_z$ where Z is 1 or 2,

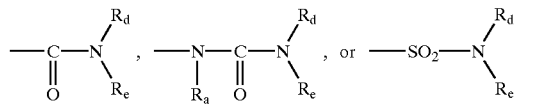

any of which may be optionally substituted through available atoms with 1, 2, 3, 4 or 5 groups selected from $Z_1$, $Z_2$, $Z_3$, $Z_4$, and $Z_5$;

R$_c$ is hydrogen, alkyl, alkenyl, alkynyl, aryl, heteroaryl, arylalkyl, arylalkenyl, arylalkynyl, heteroarylalkyl, cycloalkyl, cycloalkylalkyl, polycycloalkyl, polycycloalkylalkyl, cycloalkenyl, cycloalkynyl, heterocyclo, heterocycloalkyl, cycloalkenylalkyl, polycycloalkenyl, polycycloalkenylalkyl, polycycloalkynyl, polycycloalkynylalkyl,

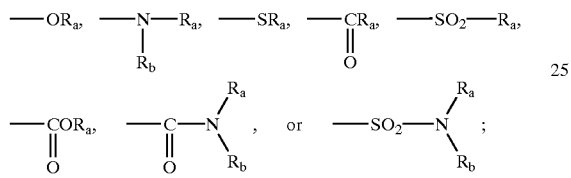

any of which may be optionally substituted through available atoms with 1, 2, 3, 4 or 5 groups selected from $Z_1$, $Z_2$, $Z_3$, $Z_4$, and $Z_5$, R$_d$ and R$_e$ are the same or different and are independently selected from hydrogen, alkyl, alkenyl, alkynyl, aryl, heteroaryl, arylalkyl, alkoxyalkyl, arylalkenyl, arylalkynyl, heteroarylalkyl, cycloalkyl, cycloalkylalkyl, polycycloalkyl, polycycloalkylalkyl, cycloalkenyl, cycloalkynyl, alkylcarbonyl, arylcarbonyl, heterocyclo, heterocycloalkyl, cycloalkenylalkyl, polycycloalkenyl, polycycloalkenylalkyl, polycycloalkynyl, polycycloalkynylalkyl, hydroxyalkyl, alkoxycarbonyl or aminocarbonyl any which may be optionally substituted through available atoms with 1, 2, 3, 4 or 5 groups selected from $Z_1$, $Z_2$, $Z_3$, $Z_4$, and $Z_5$;

or R$_d$ and R$_e$ can be taken together with the nitrogen to which they are attached to form a heterocyclo ring or a heteroaryl ring optionally substituted through available atoms with 1, 2, 3, 4 or 5 groups selected from $Z_1$, $Z_2$, $Z_3$, $Z_4$, and $Z_5$;

$Z_1$, $Z_2$, $Z_3$, $Z_4$ and $Z_5$ are the same or different and are independently selected from hydrogen, halo, alkyl, haloalkyl, polyhaloalkyl, alkoxy, alkoxyalkyl, carboxy, carboxyalkyl, haloalkoxy, polyhaloalkoxy, alkoxycarbonyl, alkoxycarbonylalkyl, alkenyl, alkynyl, cycloalkyl, cycloalkylalkyl, heterocyclo, heterocycloalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, oxo, hydroxyalkyl, nitro, cyano, amino, substituted amino, alkylamino, dialkylamino, thiol, alkylthio, arylthio, heteroarylthio, arylthioalkyl, C(O)H, alkylcarbonyl, arylcarbonyl, amido, arylaminocarbonyl, alkoxycarbonyl, aminocarbonyl, substituted aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, alkoxycarbonylamino, arylsulfinyl, arylsulfinylalkyl, arylsulfonyl, alkylsulfonyl, aminosulfinyl, aminosulfonyl, arylsulfonylamino, heteroarylcarbonylamino, heteroarylsulfinyl, heteroarylsulfonyl, alkylsulfinyl, sulfonamido, sulfonyl, amidino, guanidino,

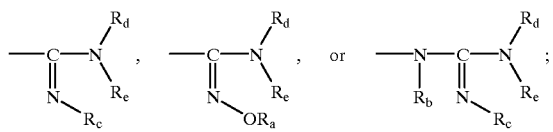

and wherein

R$_4$ and R$_5$ can be taken together with the nitrogen to which they are attached to form a heterocyclo ring or a heteroaryl ring optionally substituted through available atoms with 1, 2, 3, 4 or 5 groups selected from $Z_1$, $Z_2$, $Z_3$, $Z_4$, and $Z_5$;

R$_5$ and R$_{11}$ can be taken together to form a heteroaryl ring optionally substituted through available atoms with 1, 2,3,4 or 5 groups selected from $Z_1$, $Z_2$, $Z_3$, $Z_4$, and $Z_5$;

R$_5$ or R$_4$ or R$_{11}$ or R$_{12}$ can form a ring with R$^6$ which can be a heterocyclo or a heteroaryl ring optionally substituted through available atoms with 1, 2, 3, 4 or 5 groups selected from $Z_1$, $Z_2$, $Z_3$, $Z_4$, and $Z_5$;

or R$_{10a}$ can combine with R$_8$ or R$_9$ on an adjacent carbon atom to form a saturated or unsaturated carbocyclic or heterocyclo ring optionally substituted through available atoms with 1, 2, 3, 4 or 5 groups selected from $Z_1$, $Z_2$, $Z_3$, $Z_4$, and $Z_5$;

R$_{10}$ and R$_{10a}$ groups on adjacent carbon atoms can combine to form a saturated or unsaturated carbocyclic or heterocyclic ring optionally substituted through available atoms with 1, 2, 3, 4 or 5 groups selected from $Z_1$, $Z_2$, $Z_3$, $Z_4$, and $Z_5$;

R$_{11}$ and R$_{12}$ can combine to form a saturated or unsaturated carbocyclic or heterocyclic ring optionally substituted through available atoms with 1, 2, 3, 4 or 5 groups selected from $Z_1$, $Z_2$, $Z_3$, $Z_4$, and $Z_5$.

2. The compound of claim 1 wherein

R$_1$ and R$_2$ are each independently hydrogen, halogen or alkyl;

R$_3$ is selected from optionally subsituted aryl,

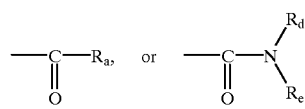

where R$_d$ and R$_e$ taken with the nitrogen to which they are attached form a 3 to 6-membered saturated ring which may be optionally substituted through available atoms with 1 to 5 groups selected from $Z_1$, $Z_2$, $Z_3$, $Z_4$, and $Z_5$;

R$_6$ and R$_7$ are each H;

R$_8$, R$_9$, R$_{10}$ and R$_{10a}$ are each hydrogen; or R$_{10}$ combines with one of R$_8$, or R$_9$ on an adjacent carbon atom, or combines with another R$_{10}$ on an adjacent carbon atom to form an optionally substituted unsaturated carbocylic ring;

$R_4$ is H or alkyl;
$R_5$ is H, alkyl, aryl, arylalkyl, heteroaryl, heterocyclo,

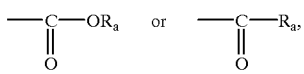

any of which may be optionally substituted through available atoms with 1 to 5 groups selected from $Z_1$, $Z_2$, $Z_3$, $Z_4$, and $Z_5$;

$R_{11}$ and $R_{12}$ are the same or different and are independently selected from hydrogen, carboxy, aryl, cyano, nitro, heteroaryl, $-P(O)(OR_a)_2$, $-S(O)_2R_a$, $-C(O)R_a$, $C(O)OR_a$,

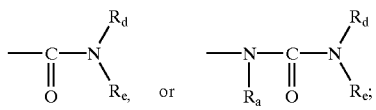

or $R_{11}$ and $R_{12}$ combine to form an optionally substituted saturated or unstaturated carbocyclic or heterocyclic ring;

$R_a$ is hydrogen, aryl, alkyl, heteroaryl or heterocyclo any of which may be optionally substituted through available atoms with 1 to 5 groups selected from $Z_1$, $Z_2$, $Z_3$, $Z_4$, and $Z_5$; and $R_b$ is hydrogen or alkyl.

3. A compound of claim 2 wherein
$R_3$ is selected from
   (a) optionally substituted phenyl;
   (b)

where $R_a$ is phenyl, phenylalkoxy, furyl, or thienyl any of which may be optionally substituted; and
   (c)

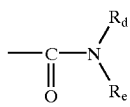

where $R_d$ and $R_e$ taken with the nitrogen to which they are attached form an optionally substituted saturated ring;

$R_5$ is
   (a) aryl, arylalkyl, or heteroaryl any of which may be optionally substituted;
   (b)

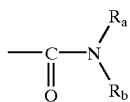

where $R_a$ is hydrogen or alkyl, and $R_b$ is alkyl, aminocarbonyl, alkoxycarbonyl, aminocarbonylalkyl, carboxyalkyl, or hydroxyalkyl; and
   (c) $C(O)R_a$, or $C(O)OR_a$ where $R_a$ is alkyl, alkenyl, hydroxyalkyl, cycloalkyl, cycloheteroalkyl, aryl or heteroaryl, any of which may be optionally substituted);

$R_{11}$ and $R_{12}$ are the same or different and are independently selected from hydrogen, nitro, carboxy, cyano, aryl, heteroaryl, $-CO_2R_{a1}$, $-SO_2R_{a1}$, $-CONR_{d1}R_{e1}$, and $-C(O)R_{a2}$ where
   $R_{a2}$ is alkyl, aryl or heteroaryl any of which may be optionally substituted with one or more alkoxy, alkyl or halogen, and
   $R_{a1}$ $R_{d1}$ and $R_{e1}$ are independently selected from hydrogen, alkyl, alkoxyalkyl, aryl and heteroaryl;
or $R_{11}$ and $R_{12}$ combine to form an optionally substituted ring of formula

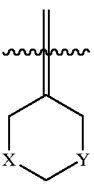

where X and Y are independently selected from $NR_a$ and O.

4. The compound of claim 3 wherein $R_5$ is aryl, arylalkyl, or heteroaryl any of which may be optionally substituted independently substituted with one or more groups selected from halogen, alkyl, haloalkyl, hydroxyalkyl, acyl, alkoxy, haloalkoxy, cyano, amino, aryl, oxo, $-C(NH)NH_2$, or $-C(O)NH_2$).

5. A pharmaceutical composition comprising at least one compound of claim 1 together with a pharmaceutically acceptable vehicle or carrier therefor.

6. The pharmaceutical compostion of claim 5 further comprising at least one additional therapeutic agent selected from anti-arryhthmic agents, anti-hypertensive agents, anti-platelet agents, anti-thrombotic agents, anti-thrombolytic agents, calcium channel blockers, cardiac glycosides, diruetics, mineralocorticoid receptor antagonists, phospodiesterase inhibitors, lipid lowering agents and lipid profile therapies; anti-diabetic agents, anti-depressants, anti-inflammatory agents, anti-osteoporosous agents, hormone replacement therapies, and oral contraceptives.

7. The pharmaceutical composition of claim 6 wherein the additional therapeutic agent is an anti-arryhthmic agent selected from sotalol, dofetilide, amiodarone, azimilide, ibutilide, diltiazem, verapamil and $K^+$ channel openers.

8. The pharmaceutical composition of claim 6 wherein the additional therapeutic agent is an anti-hypertensive agent selected from ACE inhibitors, AT-1 receptor antagonists, ET receptor antagonists, dual ET/AII receptor antagonists, and vasopepsidase inhibitors.

9. The pharmaceutical composition of claim 8 wherein the ACE inhibitor is captopril.

10. The pharmaceutical composition of claim 8 wherein the AT-1 receptor antagonist is irbesartan.

11. The pharmaceutical composition of claim 8 wherein the vasopepsidase inhibitor is omapatrilat or gempatrilat.

12. The pharmaceutical composition of claim 6 wherein the additional therapeutic agent is an antiplatelet agent selected from GPIIb/IIIa blockers, $P2Y_{12}$ antagonists, thromboxane receptor antagonists, and aspirin.

13. The pharmaceutical composition of claim 12 wherein the $P2Y_{12}$ antagonist is clopidigrel.

14. The pharmaceutical composition of claim 12 wherein the thromboxane receptor antagonist is ifetroban.

15. The pharmaceutical composition of claim 6 wherein the additional therapeutic agent is an anti-thrombotic or anti-thrombolytic agent selected from thrombin inhibitors, alpha2-antiplasmin inhibitors, streptokinase, urokinase, and prourokinase.

16. The pharmaceutical composition of claim 6 wherein the additional therapeutic agent is an anti-diabetic agent selected from biguanides, sulfonylureas, biguanide/glyburide combinations, aP2 inhibitors, and DP4 inhibitors.

17. The pharmaceutical composition of claim 6 wherein the additional therapeutic agent is an anti-inflammatory agent selected from cyclooxygenase inhibitors, and aspirin.

18. A method of treating a Factor Xa-associated disorder selected from (a) myocardial infarction, unstable angina, or non-Q Wave MI;

(b) thromboembolic stroke;

(c) venous thrombosis;

(d) pulmonary embolism;

(e) peripheral occlusive arterial disease;

(f) thromboembolic consequences of surgery, interventional cardiology or immobility;

(g) development of thrombosis on artificial surfaces;

(h) thrombotic consequences of atherosclerotic vascular disease, and/or athersclerotic plaque rupture;

(i) coagulopathy;

(j) disseminated intravascular coagulation; and (k) thromboembolic consequences of thrombophilia comprising administering an effective amount of at least one compound of claim 1 to a patient in need thereof.

* * * * *